US009321847B2

(12) United States Patent
Benhar et al.

(10) Patent No.: US 9,321,847 B2
(45) Date of Patent: Apr. 26, 2016

(54) ACTIVATABLE TOXIN COMPLEXES COMPRISING A CLEAVABLE INHIBITORY PEPTIDE

(75) Inventors: Itai Benhar, Rehovot (IL); Assaf Shapira, Petach Tikva (IL); Meital Gal-Tanamy, Rehovot (IL); Dana Greenfeld, Haifa (IL); Limor Nahary, Givataim (IL); Romy Zemel, Tel Aviv (IL); Ran Tur-Kaspa, Mevaseret Zion (IL)

(73) Assignee: RAMOT at Tel Aviv University Ltd., Tel Aviv (IL)

( * ) Notice: Subject to any disclaimer, the term of this patent is extended or adjusted under 35 U.S.C. 154(b) by 82 days.

(21) Appl. No.: 13/823,735

(22) PCT Filed: Aug. 22, 2011

(86) PCT No.: PCT/IL2011/000680
§ 371 (c)(1),
(2), (4) Date: Mar. 15, 2013

(87) PCT Pub. No.: WO2012/038950
PCT Pub. Date: Mar. 29, 2012

(65) Prior Publication Data
US 2013/0202598 A1    Aug. 8, 2013

Related U.S. Application Data

(60) Provisional application No. 61/384,342, filed on Sep. 20, 2010.

(51) Int. Cl.
*A61K 39/00*    (2006.01)
*A61K 39/29*    (2006.01)
(Continued)

(52) U.S. Cl.
CPC .............. *C07K 16/46* (2013.01); *C07K 14/195* (2013.01); *C07K 14/21* (2013.01); *C07K 14/32* (2013.01);
(Continued)

(58) Field of Classification Search
None
See application file for complete search history.

(56) References Cited

U.S. PATENT DOCUMENTS 5,593,866 A * 1/1997 Hancock et al. ............. 435/69.7
6,942,981 B1 * 9/2005 Lu et al. ........................ 435/7.1

(Continued)

FOREIGN PATENT DOCUMENTS

EP          0541335        5/1993
WO       WO 9613599      * 5/1996
(Continued)

OTHER PUBLICATIONS

Rich et al., "Human Acidic Ribosomal Phosphoproteins P0, P1, and P2: Analysis of cDNA Clones, In Vitro Synthesis, and Assembly," vol. 7, No. 11: 4065-4074 (1987).*
(Continued)

*Primary Examiner* — Benjamin P Blumel
*Assistant Examiner* — M. Franco Salvoza
(74) *Attorney, Agent, or Firm* — Rodney J. Fuller; Booth Udall Fuller, PLC

(57) ABSTRACT

The present invention relates to activatable toxin complexes which include a cleavable inhibitory peptide. More specifically, the complexes comprise a cell targeting domain, a toxin catalytic domain, a specific protease cleavage site and an inhibitory peptide domain. The inhibitory peptide prevents the catalytic domain from exerting toxic effects until its release from the complex by the action of a protease, such a viral protease, at the protease cleavage site. Further provided are pharmaceutical compositions comprising the complexes and use thereof for treating infections and malignant disease.

5 Claims, 11 Drawing Sheets

(51) Int. Cl.

| | |
|---|---|
| A61K 39/385 | (2006.01) |
| C07K 16/46 | (2006.01) |
| C07K 14/21 | (2006.01) |
| C07K 14/415 | (2006.01) |
| C12N 9/14 | (2006.01) |
| C12N 9/50 | (2006.01) |
| C12N 15/62 | (2006.01) |
| C07K 14/195 | (2006.01) |
| C07K 14/32 | (2006.01) |
| C07K 14/37 | (2006.01) |
| C07K 14/705 | (2006.01) |
| C07K 16/10 | (2006.01) |
| C07K 16/18 | (2006.01) |
| A61K 38/00 | (2006.01) |

(52) U.S. Cl.
CPC ............... *C07K 14/37* (2013.01); *C07K 14/415* (2013.01); *C07K 14/705* (2013.01); *C07K 16/1045* (2013.01); *C07K 16/18* (2013.01); *C12N 9/14* (2013.01); *C12N 9/506* (2013.01); *C12N 15/62* (2013.01); *A61K 38/00* (2013.01)

(56) References Cited

U.S. PATENT DOCUMENTS

| | | | |
|---|---|---|---|
| 7,247,715 | B2 | 7/2007 | Borgford |
| 2002/0094334 | A1 | 7/2002 | Keener |
| 2006/0024331 | A1* | 2/2006 | Fernandez-Salas et al. .......... 424/239.1 |
| 2007/0202117 | A1* | 8/2007 | Groen et al. ................ 424/164.1 |
| 2010/0273702 | A1 | 10/2010 | Chinea Santiago |

FOREIGN PATENT DOCUMENTS

| | | |
|---|---|---|
| WO | WO 9849311 * | 11/1998 |
| WO | 99/29721 | 6/1999 |
| WO | 00/62067 | 10/2000 |
| WO | 02/087500 | 11/2002 |
| WO | 03/064453 | 8/2003 |
| WO | 2004/005473 | 1/2004 |
| WO | 2005/090393 | 9/2005 |
| WO | 2006/109196 | 10/2006 |
| WO | WO 2008011157 A2 * | 1/2008 |
| WO | 2008/052322 | 5/2008 |
| WO | WO 2009001975 A1 * | 12/2008 |
| WO | 2009/022236 | 2/2009 |

OTHER PUBLICATIONS

Robinson et al., "Optimizing the stability of single-chain proteins by linker length and composition mutagenesis," PNAS vol. 95: 5929-5934 (1998).*
Agerberth et al., (2000) The human antimicrobial and chemotactic peptides LL-37 and α -defensins are expressed by specific lymphocyte and monocyte populations. Blood 96: 3086-3093.
Bartenschlager (1999) The NS3/4A proteinase of the hepatitis C virus: unravelling structure and function of an unusual enzyme and a prime target for antiviral therapy. J Viral Hepat 6: 165-81.
Bass et al., (1992) A maize ribosome-inactivating protein is controlled by the transcriptional otivator Opaque-2. Plant Cell 4: 225-34.
Chou at al., (2008) The ribosomal stalk is required for ribosome binding, depurinalion of the rRNA and cytotoxicity of ricin a chain in Saccharomyces cerevisiae, Mol Microbiol 70; 1441-52.
Debinski and Pastan (1994) An immunotoxin with increased activity and homogeneity produced by reducing the number of lysine residues in recombinant *Pseudomonas* exotoxin. Bioconjug Chem 5: 40-5.
Deng and Barbieri (2008) Molecular mechanisms of the cytotoxicity of ADP-ribosylating toxins. Annu Rev Microbiol 62: 271-88.
Edwards et al., (1991) A simple and rapid method for the preparation of plant genomic DNA for PCR analysis. Nucleic Acids Res 19: 1349.

Ericksen et al., (2905) Antibacterial activity and specificity o he six human alpha • defensins. Antimicrob Agents Chemother, 49: 269-275.
Falnes (2040) Design of toxins that can be activated by cell specific proteases and their potential use in targeted cell killing. Int J Med Microbiol. 290(4-5): 471-476.
Falnes et al., (1999) Toxins that are activated by HIV type-9 protease through removal of a signal for degradation by the N-end-rule pathway. Biochem J 343: 199-207.
FitzGerald and Pastan (1991) Redirecting *Pseudomonas* exotoxin. Semin Cell Biol 2: 31-7.
Frelin et al., Low dose and gene gun immunization with a hepatitis C virus nonstructural (NS) 3 DNA-based vaccine containing NS4A inhibit NS3/4A-expressing tumors in vivo, Gene Ther 10: 686-99.
Gal-Tanamy et al., (2005) HCV NS3 serine protease-neutralizing single-chain antibodies isolated by a novel genetic screen. J Mol Biol 347: 991-1003.
Ganz et al., (1985) Defensins. Natural peptide antibiotics of human neutrophils. J Clin Invest 76(4): 1427-1435.
Ganz (2003) Defensins: antimicrobial peptides of innate immunity. Nat. Rev. Immunol 3: 710-720.
Gu et al., (1996) Furin regulates both the activation of *Pseudomonas* exotoxin A and the Quantity of the toxin receptor expressed on target cells. Infect Immun 64: 524-7.
Hwang et al., (1987) Functional domains of *Pseudomonas* exotoxin identified by deletion analysis of the gene expressed in *E. coli*. Cell 48: 129-36.
Iglewski and Kabat (1975) NAD-dependent inhibition of protein synthesis by *Pseudomonas aeruginosa* toxin. Proc Natl Acad Sci U S A 72: 2284-8.
Jackson et al., (1999) The KDEL retrieval system is exploited by *Pseudomonas* exotoxin A, but not by Shiga-like toxin-1, during retrograde transport from the Golgi complex to the endoplasmic reticulum. J Cell Sci 112 ( Pt 4): 467-75.
Johnson et al., (2006) A ribonuclease zymogen activated by the NS3 protease of the hepatitis virus. Febs J 273: 5457-65.
Jorgensen et al., (2005). Exotoxin A-eEF2 complex structure indicates ADP ribosylation by ribosome mimicry. Nature 436: 979-84.
Jucovic et al., (2008) From enzyme to zymogen: engineering Vip2, an ADP-ribosyltransferase from *Bacillus cereus*, for conditional toxicity. Protein Eng Des Sel 21: 631-8.
Kim et al., (2006) Human alpha-defensins neutralize toxins of the mono-ADP-ribosyltransferase family. Biochem J 399: 225-229.
Kim et al., (2005) Human α-defensins neutralize anthrax lethal toxin and protect against its fatal consequences. Proc Nati Acad Sci USA 102(13): 4830-4835.
Law et al., (2010) A switch-on mechanism to activate maize ribosome-inactivating protein for targeting HIV-infected cells Nucleic Adds Res 38(19): 6803-6812.
Lehrer et al., (1993) Defensins: antimicrobial and Cytotoxic peptides of mammalian cells. Annu. Rev. Immunol. 11: 105-128.
Mansfield et al., (1996) Characterization of RFB4-*Pseudomonas* exotoxin A immunotoxins targeted to CD22 on B-cell malignancies. Bioconjug Chem 7: 557-63.
May (1989) Ribosome inactivation by ricin A chain: a sensitive method to assess the activity of wild-type and mutant polypeptides. Embo J 8: 301-8.
McCluskey et al., (2008) The catalytic subunit of shiga-like toxin 1 interacts with ribosomal stalk proteins and is inhibited by their conserved C-terminal domain. J Mol Biol 378: 375-386.
McGivem et al., (2009) Impaired replication of hepatitis C virus containing mutations in a conserved NS5B retinoblastoma protein-binding motif. J Virol 83: 7422-33.
Olsnes (2004) The history of ricin, abrin and related toxins. Toxicon 44: 361-70.
Peumans et al., (2001) Classification of plant lectins in families structurally and evolutionary related proteins. Adv Exp Med Biol 491: 27-54.
Pietschmann et al., (2006) Construction and characterization of infectious intragenotypic and intergenotypic hepatitis C virus chimeras. Proc Natl Acad Sci U S A 103: 7408-13.
Plainkum et al., (2003) Creation of a zymogen. Nat Struct Biol 10: 115-9.

(56) References Cited

OTHER PUBLICATIONS

Potrich et al., (2009) Cytotoxic activity of a tumor protease-activated pore-forming toxin. Bioconjug Chem 16(2): 369-376.

Ratts and Murphy (2004) Diphtheria toxin, diphtheria-related fusion protein toxins, and the molecular mechanism of their action against eukaryotic cells. Topics in Current Genetics 11.

Shaki-Loewenstein et al., (2005) A universal strategy for stable intracellular antibodies. J Immunol Methods 303: 19-39.

Shapira et al., (2011) Engineered toxins "zymoxins" are activated by the HCV NS3 protease by removal an inhibitory protein domain. PLoS One 6(1): e15916.

Steinkuhler et al, (1996) Activity of purified hepatitis C virus protease NS3 on peptide substrates. J Virol 70: 6694-700.

Stirpe and Battelli (2006) Ribosome-inactivating proteins: progress and problems. Cell Mol Life Sci 63: 1850-66.

Suzuki et al., (2007) Hepatitis C viral life cycle. Adv Drug Deliv Rev 59(12): 1200-1212.

Too et al., (2009) The C-terminal fragment of the ribosomal P protein complexed to trichosanthin reveals the interaction between the ribosome-inactivating protein and the ribosome, Nucleic Acids Res 37: 602-10.

Turcotte and Raines (2008) Design and Characterization of an HIV-Specific Ribonuclease Zymogen. AIDS Res Hum Retroviruses 24: 1357-1363.

Varshavsky (1995) The N-end rule. Cold Spring Harb Symp Quant Biol 60: 461-78.

Vater et al., (1995) Ricin A chain can be chemically cross-linked to the mammalian ribosomal proteins L9 and L10e. J Biol Chem 270: 12933-40.

Wakita et al., (2005) Production of infectious, hepatitis C virus in tissue culture from a cloned viral genome. Nat Med 11: 791-6.

Walsh et al., (1991) Characterization and molecular cloning of a proenzyme form of a ribosome-inactivating protein from maize. Novel mechanism of proenzyme activation by proteolytic removal of a 2.8-kilodalton internal peptide segment. J Biol Chem 266: 23422-7.

Yi et al., (2006) Production of infectious genotype 1a hepatitis C virus (Hutchinson strain) in cultured human hepatoma cells. Proc. Natl.Acad.Sci.U.S.A 103: 2310-2315.

Zemel et al., (2004) Inhibition of Hepatitis C Virus NS3-mediated cell transformation recombinant intracellular antibodies. J Hepatal 40: 1000-1007.

* cited by examiner

PE-RTA-CLEAVAGE SITE-STALK PEPTIDE

Figure 4A

PE-RTA-MUTATED CLEAVAGE SITE-STALK PEPTIDE

NS3 TREATMENT

NS3 CLEAVABLE TOXIN { − / + }  ← R FRAGMENT

NON CLEAVABLE TOXIN { − / + }

Toxin conc. (ng/ml)  5000  5000  500  50
Aniline                −     +     +    +

FIG.4D

N'—[PE BINDING DOMAIN][PE TRANSLOCATION DOMAIN][RICIN CATALYTIC DOMAIN (RTA)]— CATALYTIC SITE — Stalk pep. — RIBOSOME BINDING SITE — NS3 PROTEASE

PE-RTA-CLEAVAGE SITE-STALK PEPTIDE

FIG.5A

N'—[PE BINDING DOMAIN][PE TRANSLOCATION DOMAIN][RICIN CATALYTIC DOMAIN (RTA)]— CATALYTIC SITE — Stalk pep. — RIBOSOME BINDING SITE — NS3 PROTEASE

PE-RTA-MUTATED CLEAVAGE SITE-STALK PEPTIDE

SEQUENCE LISTING

```
<160> NUMBER OF SEQ ID NOS: 130

<210> SEQ ID NO 1
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 1

Glu Asp Val Val Cys Cys Ser Met Ser Tyr
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 2

Asp Ser Val Val Cys Cys Ser Met Ser Tyr
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 3

Glu Gly Val Ile Cys Cys Ser Met Ser Tyr
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 4

Asp Ser Val Ile Cys Cys Ser Met Ser Tyr
1               5                   10
```

```
<210> SEQ ID NO 5
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 5

Asp Asp Val Ile Cys Cys Ser Met Ser Tyr
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 6

Gln Ser Val Val Cys Cys Ser Met Ser Tyr
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 7

Asp Leu Glu Val Val Thr Ser Thr Trp Val
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 8

Asp Leu Glu Val Met Thr Ser Thr Trp Val
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 9

Asp Leu Glu Ile Met Thr Ser Thr Trp Val
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 10

Gln Leu Glu Val Val Thr Ser Thr Trp Val
1               5                   10
```

<210> SEQ ID NO 11
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 11

Asp Glu Met Glu Glu Cys Ser Gln His Leu
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 12

Asp Glu Met Glu Glu Cys Ala Ser His Leu
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 13

Asp Glu Met Glu Glu Cys Ala Ser Arg Ala
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 14

Asp Glu Met Glu Glu Cys Ala Ser Lys Ala
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 15

Glu Cys Thr Thr Pro Cys Ser Gly Ser Trp
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 16

Asp Cys Ser Thr Pro Cys Ser Gly Ser Trp
1               5                   10

<210> SEQ ID NO 17

```
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 17

Asp Cys Pro Ile Pro Cys Ser Gly Ser Trp
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 18

Asp Cys Pro Val Pro Cys Ser Gly Ser Trp
1               5                   10

<210> SEQ ID NO 19
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 19

Ser Glu Glu Asp Asp Thr Thr Val Cys Cys Ser Met Ser Tyr Ser Trp
1               5                   10                  15

Thr Gly Ala Leu
            20

<210> SEQ ID NO 20
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 20

Glu Glu Ala Ser Glu Asp Val Val Cys Cys Ser Met Ser Tyr Thr Trp
1               5                   10                  15

Thr Gly Ala Leu
            20

<210> SEQ ID NO 21
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 21

Ser Glu Glu Asp Asp Ser Val Val Cys Cys Ser Met Ser Tyr Ser Trp
1               5                   10                  15

Thr Gly Ala Leu
            20

<210> SEQ ID NO 22
<211> LENGTH: 20
<212> TYPE: PRT
<213> ORGANISM: Artificial Sequence
<220> FEATURE:
<223> OTHER INFORMATION: Synthetic polypeptide
```

```
<400> SEQUENCE: 22

Glu Glu Asp Gly Glu Gly Val Ile Cys Cys Ser Met Ser Tyr Thr Trp
1               5                   10                  15

Thr Gly Ala Leu
            20

<210> SEQ ID NO 23
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 23

Ser Asp Gln Glu Asp Ser Val Ile Cys Cys Ser Met Ser Tyr Ser Trp
1               5                   10                  15

Thr Gly Ala Leu
            20

<210> SEQ ID NO 24
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 24

Gly Glu Ala Ser Asp Asp Val Ile Cys Cys Ser Met Ser Tyr Thr Trp
1               5                   10                  15

Thr Gly Ala Leu
            20

<210> SEQ ID NO 25
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 25

Asp Ser Glu Glu Gln Ser Val Val Cys Cys Ser Met Ser Tyr Ser Trp
1               5                   10                  15

Thr Gly Ala Leu
            20

<210> SEQ ID NO 26
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 26

Gly Ala Asp Thr Glu Asp Val Val Cys Cys Ser Met Ser Tyr Ser Trp
1               5                   10                  15

Thr Gly Ala Leu
            20

<210> SEQ ID NO 27
<211> LENGTH: 20
<212> TYPE: PRT
<213> ORGANISM: Artificial Sequence
<220> FEATURE:
```

<223> OTHER INFORMATION: Synthetic polypeptide

<400> SEQUENCE: 27

Cys Met Ser Ala Asp Leu Glu Val Val Thr Ser Thr Trp Val Leu Val
1               5                   10                  15

Gly Gly Val Leu
            20

<210> SEQ ID NO 28
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 28

Cys Met Gln Ala Asp Leu Glu Val Met Thr Ser Thr Trp Val Leu Ala
1               5                   10                  15

Gly Gly Val Leu
            20

<210> SEQ ID NO 29
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 29

Cys Met Gln Ala Asp Leu Glu Ile Met Thr Ser Thr Trp Val Leu Ala
1               5                   10                  15

Gly Gly Val Leu
            20

<210> SEQ ID NO 30
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 30

Cys Met Ser Ala Gln Leu Glu Val Val Thr Ser Thr Trp Val Leu Val
1               5                   10                  15

Gly Gly Val Leu
            20

<210> SEQ ID NO 31
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 31

Tyr Gln Glu Phe Asp Glu Met Glu Glu Cys Ser Gln His Leu Pro Tyr
1               5                   10                  15

Ile Glu Gln Gly
            20

<210> SEQ ID NO 32
<211> LENGTH: 20
<212> TYPE: PRT
<213> ORGANISM: Artificial Sequence

```
<220> FEATURE:
<223> OTHER INFORMATION: Synthetic polypeptide

<400> SEQUENCE: 32

Tyr Gln Glu Phe Asp Glu Met Glu Glu Cys Ala Ser His Leu Pro Tyr
1               5                   10                  15

Ile Glu Gln Gly
            20

<210> SEQ ID NO 33
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 33

Tyr Glu Ala Phe Asp Glu Met Glu Glu Cys Ala Ser Arg Ala Ala Leu
1               5                   10                  15

Ile Glu Glu Gly
            20

<210> SEQ ID NO 34
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 34

Tyr Gln Ala Phe Asp Glu Met Glu Glu Cys Ala Ser Lys Ala Ala Leu
1               5                   10                  15

Ile Glu Glu Gly
            20

<210> SEQ ID NO 35
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 35

Trp Ile Ser Ser Glu Cys Thr Thr Pro Cys Ser Gly Ser Trp Leu Arg
1               5                   10                  15

Asp Ile Trp Asp
            20

<210> SEQ ID NO 36
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 36

Trp Ile Asn Glu Asp Cys Ser Thr Pro Cys Ser Gly Ser Trp Leu Arg
1               5                   10                  15

Asp Val Trp Asp
            20

<210> SEQ ID NO 37
<211> LENGTH: 20
<212> TYPE: PRT
```

```
<213> ORGANISM: Artificial Sequence
<220> FEATURE:
<223> OTHER INFORMATION: Synthetic polypeptide

<400> SEQUENCE: 37

Trp Ile Thr Glu Asp Cys Pro Ile Pro Cys Ser Gly Ser Trp Leu Arg
1               5                   10                  15

Asp Val Trp Asp
            20

<210> SEQ ID NO 38
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 38

Trp Ile Thr Glu Asp Cys Pro Val Pro Cys Ser Gly Ser Trp Leu Gln
1               5                   10                  15

Asp Ile Trp Asp
            20

<210> SEQ ID NO 39
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 39

Ser Gly Val Val Asn Ala Ser Cys Arg Leu Ala Asn
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 40

Ser Ser Tyr Val Lys Ala Ser Val Ser Pro Glu Asn
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 41

Ser Ala Leu Val Asn Ala Ser Ser Ala His Val Asn
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 42

Ser Thr Tyr Leu Gln Ala Ser Glu Lys Phe Lys Asn
1               5                   10
```

-continued

<210> SEQ ID NO 43
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 43

Val Ser Gln Asn Tyr Pro Ile Val Gln Asn
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 44

Lys Ala Arg Val Leu Ala Glu Ala Met Ser
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 45

Ser Thr Ala Ile Met Met Gln Lys Gly Asn
1               5                   10

<210> SEQ ID NO 46
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 46

Thr Ser Ala Ile Met Met Gln Arg Gly Asn
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 47

Glu Arg Gln Ala Asn Phe Leu Gly Lys Ile
1               5                   10

<210> SEQ ID NO 48
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 48

Arg Pro Gly Asn Phe Leu Gln Ser Arg Pro
1               5                   10

```
<210> SEQ ID NO 49
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 49

Glu Arg Gln Ala Asn Phe Leu Arg Glu Asn
1               5                   10

<210> SEQ ID NO 50
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 50

Glu Asn Leu Ala Phe Gln Gln Gly Glu Ala
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 51

Glu Asp Leu Ala Phe Leu Gln Phe Lys Ala
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 52

Thr Ser Phe Ser Phe Pro Gln Ile Thr Cys
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 53

Val Ser Phe Asn Phe Pro Gln Val Thr Cys
1               5                   10

<210> SEQ ID NO 54
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 54

Cys Thr Leu Asn Phe Pro Ile Ser Pro Ile Gly Ala Glu Thr Phe Tyr
1               5                   10                  15

Val Asp Gly Ala
```

<210> SEQ ID NO 55
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 55

```
Ile Arg Lys Val Leu Phe Leu Asp Gly Ile
1               5                   10
```

<210> SEQ ID NO 56
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 56

```
Pro Asp Cys Ala Trp Leu Glu Ala Gln Glu
1               5                   10
```

<210> SEQ ID NO 57
<211> LENGTH: 30
<212> TYPE: PRT
<213> ORGANISM: Artificial Sequence
<220> FEATURE:
<223> OTHER INFORMATION: Synthetic polypeptide

<400> SEQUENCE: 57

```
Ala Cys Tyr Cys Arg Ile Pro Ala Cys Ile Ala Gly Glu Arg Arg Tyr
1               5                   10                  15
Gly Thr Cys Ile Tyr Gln Gly Arg Leu Trp Ala Phe Cys Cys
            20                  25                  30
```

<210> SEQ ID NO 58
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 58

```
Glu Glu Ser Glu Glu Ser Asp Asp Asp Met Gly Phe Gly Leu Phe Asp
1               5                   10                  15
```

<210> SEQ ID NO 59
<211> LENGTH: 35
<212> TYPE: PRT
<213> ORGANISM: Artificial Sequence
<220> FEATURE:
<223> OTHER INFORMATION: Synthetic polypeptide

<400> SEQUENCE: 59

```
Glu Glu Ser Glu Glu Ser Asp Asp Asp Met Gly Phe Gly Leu Phe Asp
1               5                   10                  15
Thr Gly Gly Glu Glu Ser Glu Glu Ser Asp Asp Asp Met Gly Phe Gly
            20                  25                  30
Leu Phe Asp
        35
```

<210> SEQ ID NO 60
<211> LENGTH: 15

```
<212> TYPE: PRT
<213> ORGANISM: Artificial Sequence
<220> FEATURE:
<223> OTHER INFORMATION: Synthetic polypeptide

<400> SEQUENCE: 60

Gly Gly Gly Gly Ser Gly Gly Gly Ser Gly Ser Gly Gly Ser Gly
1               5                   10                  15

<210> SEQ ID NO 61
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 61

Gly Ser Gly Ser
1

<210> SEQ ID NO 62
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 62

Ser Ser Gly Ser
1

<210> SEQ ID NO 63
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 63

Gly Gly Gly Gly Ser
1               5

<210> SEQ ID NO 64
<211> LENGTH: 695
<212> TYPE: PRT
<213> ORGANISM: Artificial Sequence
<220> FEATURE:
<223> OTHER INFORMATION: Synthetic polypeptide

<400> SEQUENCE: 64

Met Lys Lys Thr Ala Ile Ala Ile Ala Val Ala Leu Ala Gly Phe Ala
1               5                   10                  15

Thr Val Ala Gln Ala Ala Asn Leu Ala Glu Glu Ala Phe Asp Leu Trp
            20                  25                  30

Asn Glu Cys Ala Lys Ala Cys Val Leu Asp Leu Lys Asp Gly Val Arg
        35                  40                  45

Ser Ser Arg Met Ser Val Asp Pro Ala Ile Ala Asp Thr Asn Gly Gln
    50                  55                  60

Gly Val Leu His Tyr Ser Met Val Leu Glu Gly Gly Asn Asp Ala Leu
65                  70                  75                  80

Lys Leu Ala Ile Asp Asn Ala Leu Ser Ile Thr Ser Asp Gly Leu Thr
                85                  90                  95

Ile Arg Leu Glu Gly Gly Val Glu Pro Asn Lys Pro Val Arg Tyr Ser
            100                 105                 110
```

```
Tyr Thr Arg Gln Ala Arg Gly Ser Trp Ser Leu Asn Trp Leu Val Pro
            115                 120                 125
Ile Gly His Glu Lys Pro Ser Asn Ile Lys Val Phe Ile His Glu Leu
        130                 135                 140
Asn Ala Gly Asn Gln Leu Ser His Met Ser Pro Ile Tyr Thr Ile Glu
145                 150                 155                 160
Met Gly Asp Glu Leu Leu Ala Lys Leu Ala Arg Asp Ala Thr Phe Phe
                165                 170                 175
Val Arg Ala His Glu Ser Asn Glu Met Gln Pro Thr Leu Ala Ile Ser
            180                 185                 190
His Ala Gly Val Ser Val Met Ala Gln Thr Gln Pro Arg Arg Glu
        195                 200                 205
Lys Arg Trp Ser Glu Trp Ala Ser Gly Lys Val Leu Cys Leu Leu Asp
        210                 215                 220
Pro Leu Asp Gly Val Tyr Asn Tyr Leu Ala Gln Gln Arg Cys Asn Leu
225                 230                 235                 240
Asp Asp Thr Trp Glu Gly Lys Ile Tyr Arg Val Leu Ala Gly Asn Pro
                245                 250                 255
Ala Lys His Asp Leu Asp Ile Lys Pro Thr Val Ile Ser His Arg Leu
            260                 265                 270
His Phe Pro Glu Gly Gly Ser Leu Ala Ala Leu Thr Ala His Gln Ala
        275                 280                 285
Cys His Leu Pro Leu Glu Thr Phe Thr Arg His Arg Gln Pro Arg Gly
        290                 295                 300
Trp Glu Gln Leu Glu Gln Cys Gly Tyr Pro Val Gln Arg Leu Val Ala
305                 310                 315                 320
Leu Tyr Leu Ala Ala Arg Leu Ser Trp Asn Gln Val Asp Gln Val Ile
                325                 330                 335
Arg Asn Ala Leu Ala Ser Pro Gly Ser Gly Gly Asp Leu Gly Glu Ala
            340                 345                 350
Ile Arg Glu Gln Pro Glu Gln Ala Arg Leu Ala Leu Thr Leu Ala Ala
        355                 360                 365
Ala Glu Ser Glu Arg Phe Val Arg Gln Gly Thr Gly Asn Asp Glu Ala
        370                 375                 380
Gly Ala Ala Asn Ala Asp Val Val Ser Leu Thr Cys Pro Val Ala Ala
385                 390                 395                 400
Gly Glu Cys Ala Gly Pro Ala Asp Ser Gly Asp Ala Leu Leu Glu Arg
                405                 410                 415
Asn Tyr Pro Thr Gly Ala Glu Phe Leu Gly Asp Gly Asp Val Gly
            420                 425                 430
Thr Gly Gly Ala Asp Asp Val Val Asp Ser Ser Lys Ser Phe Val Met
        435                 440                 445
Glu Asn Phe Ser Ser Tyr His Gly Thr Lys Pro Gly Tyr Val Asp Ser
450                 455                 460
Ile Gln Lys Gly Ile Gln Lys Pro Lys Ser Gly Thr Gln Gly Asn Tyr
465                 470                 475                 480
Asp Asp Asp Trp Lys Gly Phe Tyr Ser Thr Asp Asn Lys Tyr Asp Ala
                485                 490                 495
Ala Gly Tyr Ser Val Asp Asn Glu Asn Pro Leu Ser Gly Lys Ala Gly
            500                 505                 510
Gly Val Val Lys Val Thr Tyr Pro Gly Leu Thr Lys Val Leu Ala Leu
        515                 520                 525
```

```
Lys Val Asp Asn Ala Glu Thr Ile Lys Lys Glu Leu Gly Leu Ser Leu
            530                 535                 540

Thr Glu Pro Leu Met Glu Gln Val Gly Thr Glu Phe Ile Lys Arg
545                 550                 555                 560

Phe Gly Asp Gly Ala Ser Arg Val Val Leu Ser Leu Pro Phe Ala Glu
                    565                 570                 575

Gly Ser Ser Ser Val Glu Tyr Ile Asn Asn Trp Glu Gln Ala Lys Ala
                580                 585                 590

Leu Ser Val Glu Leu Glu Ile Asn Phe Glu Thr Arg Gly Lys Arg Gly
            595                 600                 605

Gln Asp Ala Met Tyr Glu Tyr Met Ala Gln Ala Cys Ala Glu Asp Val
        610                 615                 620

Val Cys Cys Ser Met Ser Tyr Ala Ile Gly Leu Gln Gly Gly Gly Gly
625                 630                 635                 640

Ser Gly Gly Gly Ser Gly Ser Gly Ser Gly Ala Cys Tyr Cys Arg
                    645                 650                 655

Ile Pro Ala Cys Ile Ala Gly Glu Arg Arg Tyr Gly Thr Cys Ile Tyr
                660                 665                 670

Gln Gly Arg Leu Trp Ala Phe Cys Cys Gly Ser Gly Ser His His His
            675                 680                 685

His His His Lys Asp Glu Leu
            690                 695

<210> SEQ ID NO 65
<211> LENGTH: 769
<212> TYPE: PRT
<213> ORGANISM: Artificial Sequence
<220> FEATURE:
<223> OTHER INFORMATION: Synthetic polypeptide

<400> SEQUENCE: 65

Met Lys Lys Thr Ala Ile Ala Ile Ala Val Ala Leu Ala Gly Phe Ala
1               5                   10                  15

Thr Val Ala Gln Ala Ala Asn Leu Ala Glu Glu Ala Phe Asp Leu Trp
            20                  25                  30

Asn Glu Cys Ala Lys Ala Cys Val Leu Asp Leu Lys Asp Gly Val Arg
        35                  40                  45

Ser Ser Arg Met Ser Val Asp Pro Ala Ile Ala Asp Thr Asn Gly Gln
50                  55                  60

Gly Val Leu His Tyr Ser Met Val Leu Glu Gly Gly Asn Asp Ala Leu
65                  70                  75                  80

Lys Leu Ala Ile Asp Asn Ala Leu Ser Ile Thr Ser Asp Gly Leu Thr
                85                  90                  95

Ile Arg Leu Glu Gly Gly Val Glu Pro Asn Lys Pro Val Arg Tyr Ser
            100                 105                 110

Tyr Thr Arg Gln Ala Arg Gly Ser Trp Ser Leu Asn Trp Leu Val Pro
        115                 120                 125

Ile Gly His Glu Lys Pro Ser Asn Ile Lys Val Phe Ile His Glu Leu
    130                 135                 140

Asn Ala Gly Asn Gln Leu Ser His Met Ser Pro Ile Tyr Thr Ile Glu
145                 150                 155                 160

Met Gly Asp Glu Leu Leu Ala Lys Leu Ala Arg Asp Ala Thr Phe Phe
                165                 170                 175

Val Arg Ala His Glu Ser Asn Glu Met Gln Pro Thr Leu Ala Ile Ser
            180                 185                 190
```

-continued

```
His Ala Gly Val Ser Val Val Met Ala Gln Thr Gln Pro Arg Arg Glu
            195                 200                 205

Lys Arg Trp Ser Glu Trp Ala Ser Gly Lys Val Leu Cys Leu Leu Asp
210                 215                 220

Pro Leu Asp Gly Val Tyr Asn Tyr Leu Ala Gln Gln Arg Cys Asn Leu
225                 230                 235                 240

Asp Asp Thr Trp Glu Gly Lys Ile Tyr Arg Val Leu Ala Gly Asn Pro
                245                 250                 255

Ala Lys His Asp Leu Asp Ile Lys Pro Thr Val Ile Ser His Arg Leu
            260                 265                 270

His Phe Pro Glu Gly Gly Ser Leu Ala Ala Leu Thr Ala His Gln Ala
        275                 280                 285

Cys His Leu Pro Leu Glu Thr Phe Thr Arg His Arg Gln Pro Arg Gly
    290                 295                 300

Trp Glu Gln Leu Glu Gln Cys Gly Tyr Pro Val Gln Arg Leu Val Ala
305                 310                 315                 320

Leu Tyr Leu Ala Ala Arg Leu Ser Trp Asn Gln Val Asp Gln Val Ile
                325                 330                 335

Arg Asn Ala Leu Ala Ser Pro Gly Ser Gly Gly Asp Leu Gly Glu Ala
            340                 345                 350

Ile Arg Glu Gln Pro Glu Gln Ala Arg Leu Ala Leu Thr Leu Ala Ala
        355                 360                 365

Ala Glu Ser Glu Arg Phe Val Arg Gln Gly Thr Gly Asn Asp Glu Ala
    370                 375                 380

Gly Ala Ala Asn Ala Asp Val Val Ser Leu Thr Cys Pro Val Ala Ala
385                 390                 395                 400

Gly Glu Cys Ala Gly Pro Ala Asp Ser Gly Asp Ala Leu Leu Glu Arg
                405                 410                 415

Asn Tyr Pro Thr Gly Ala Glu Phe Leu Gly Asp Gly Asp Val Ser
            420                 425                 430

Phe Ser Thr Arg Gly Ile Phe Pro Lys Gln Tyr Pro Ile Ile Asn Phe
        435                 440                 445

Thr Thr Ala Gly Ala Thr Val Gln Ser Tyr Thr Asn Phe Ile Arg Ala
    450                 455                 460

Val Arg Gly Arg Leu Thr Thr Gly Ala Asp Val Arg His Glu Ile Pro
465                 470                 475                 480

Val Leu Pro Asn Arg Val Gly Leu Pro Ile Asn Gln Arg Phe Ile Leu
                485                 490                 495

Val Glu Leu Ser Asn His Ala Glu Leu Ser Val Thr Leu Ala Leu Asp
            500                 505                 510

Val Thr Asn Ala Tyr Val Val Gly Tyr Arg Ala Gly Asn Ser Ala Tyr
        515                 520                 525

Phe Phe His Pro Asp Asn Gln Glu Asp Ala Glu Ala Ile Thr His Leu
    530                 535                 540

Phe Thr Asp Val Gln Asn Arg Tyr Thr Phe Ala Phe Gly Gly Asn Tyr
545                 550                 555                 560

Asp Arg Leu Glu Gln Leu Ala Gly Asn Leu Arg Glu Asn Ile Glu Leu
                565                 570                 575

Gly Asn Gly Pro Leu Glu Glu Ala Ile Ser Ala Leu Tyr Tyr Tyr Ser
            580                 585                 590

Thr Gly Gly Thr Gln Leu Pro Thr Leu Ala Arg Ser Phe Ile Ile Cys
        595                 600                 605

Ile Gln Met Ile Ser Glu Ala Ala Arg Phe Gln Tyr Ile Glu Gly Glu
```

```
                  610                 615                 620
Met Arg Thr Arg Ile Arg Tyr Asn Arg Arg Ser Ala Pro Asp Pro Ser
625                 630                 635                 640

Val Ile Thr Leu Glu Asn Ser Trp Gly Arg Leu Ser Thr Ala Ile Gln
                    645                 650                 655

Glu Ser Asn Gln Gly Ala Phe Ala Ser Pro Ile Gln Leu Gln Arg Arg
                660                 665                 670

Asn Gly Ser Lys Phe Ser Val Tyr Asp Val Ser Ile Leu Ile Pro Ile
            675                 680                 685

Ile Ala Leu Met Val Tyr Arg Cys Ala Pro Pro Ser Ser Gly Ser
        690                 695                 700

Glu Asp Val Val Cys Cys Ser Met Ser Tyr Gly Gly Gly Ser Glu
705                 710                 715                 720

Glu Ser Glu Glu Ser Asp Asp Asp Met Gly Phe Gly Leu Phe Asp Thr
                725                 730                 735

Gly Gly Glu Glu Ser Glu Glu Ser Asp Asp Asp Met Gly Phe Gly Leu
            740                 745                 750

Phe Asp Thr Gly Ser Leu Gln His His His His His Lys Asp Glu
        755                 760                 765

Leu

<210> SEQ ID NO 66
<211> LENGTH: 705
<212> TYPE: PRT
<213> ORGANISM: Artificial Sequence
<220> FEATURE:
<223> OTHER INFORMATION: Synthetic polypeptide

<400> SEQUENCE: 66

Met Lys Lys Thr Ala Ile Ala Ile Ala Val Ala Leu Ala Gly Phe Ala
1               5                   10                  15

Thr Val Ala Gln Ala Ala Asn Leu Ala Glu Glu Ala Phe Asp Leu Trp
                20                  25                  30

Asn Glu Cys Ala Lys Ala Cys Val Leu Asp Leu Lys Asp Gly Val Arg
            35                  40                  45

Ser Ser Arg Met Ser Val Asp Pro Ala Ile Ala Asp Thr Asn Gly Gln
        50                  55                  60

Gly Val Leu His Tyr Ser Met Val Leu Glu Gly Asn Asp Ala Leu
65                  70                  75                  80

Lys Leu Ala Ile Asp Asn Ala Leu Ser Ile Thr Ser Asp Gly Leu Thr
                85                  90                  95

Ile Arg Leu Glu Gly Gly Val Glu Pro Asn Lys Pro Val Arg Tyr Ser
            100                 105                 110

Tyr Thr Arg Gln Ala Arg Gly Ser Trp Ser Leu Asn Trp Leu Val Pro
        115                 120                 125

Ile Gly His Glu Lys Pro Ser Asn Ile Lys Val Phe Ile His Glu Leu
    130                 135                 140

Asn Ala Gly Asn Gln Leu Ser His Met Ser Pro Ile Tyr Thr Ile Glu
145                 150                 155                 160

Met Gly Asp Glu Leu Leu Ala Lys Leu Ala Arg Asp Ala Thr Phe Phe
                165                 170                 175

Val Arg Ala His Glu Ser Asn Glu Met Gln Pro Thr Leu Ala Ile Ser
            180                 185                 190

His Ala Gly Val Ser Val Val Met Ala Gln Thr Gln Pro Arg Arg Glu
        195                 200                 205
```

```
Lys Arg Trp Ser Glu Trp Ala Ser Gly Lys Val Leu Cys Leu Leu Asp
    210                 215                 220

Pro Leu Asp Gly Val Tyr Asn Tyr Leu Ala Gln Gln Arg Cys Asn Leu
225                 230                 235                 240

Asp Asp Thr Trp Glu Gly Lys Ile Tyr Arg Val Leu Ala Gly Asn Pro
                245                 250                 255

Ala Lys His Asp Leu Asp Ile Lys Pro Thr Val Ile Ser His Arg Leu
            260                 265                 270

His Phe Pro Glu Gly Gly Ser Leu Ala Ala Leu Thr Ala His Gln Ala
        275                 280                 285

Cys His Leu Pro Leu Glu Thr Phe Thr Arg His Arg Gln Pro Arg Gly
    290                 295                 300

Trp Glu Gln Leu Glu Gln Cys Gly Tyr Pro Val Gln Arg Leu Val Ala
305                 310                 315                 320

Leu Tyr Leu Ala Ala Arg Leu Ser Trp Asn Gln Val Asp Gln Val Ile
                325                 330                 335

Arg Asn Ala Leu Ala Ser Pro Gly Ser Gly Gly Asp Leu Gly Glu Ala
            340                 345                 350

Ile Arg Glu Gln Pro Glu Gln Ala Arg Leu Ala Leu Thr Leu Ala Ala
    355                 360                 365

Ala Glu Ser Glu Arg Phe Val Arg Gln Gly Thr Gly Asn Asp Glu Ala
    370                 375                 380

Gly Ala Ala Asn Ala Asp Val Val Ser Leu Thr Cys Pro Val Ala Ala
385                 390                 395                 400

Gly Glu Cys Ala Gly Pro Ala Asp Ser Gly Asp Ala Leu Leu Glu Arg
                405                 410                 415

Asn Tyr Pro Thr Gly Ala Glu Phe Leu Gly Asp Gly Gly Asp Val Gly
            420                 425                 430

Thr Gly Gly Ala Asp Asp Val Val Asp Ser Ser Lys Ser Phe Val Met
    435                 440                 445

Glu Asn Phe Ser Ser Tyr His Gly Thr Lys Pro Gly Tyr Val Asp Ser
450                 455                 460

Ile Gln Lys Gly Ile Gln Lys Pro Lys Ser Gly Thr Gln Gly Asn Tyr
465                 470                 475                 480

Asp Asp Asp Trp Lys Gly Phe Tyr Ser Thr Asp Asn Lys Tyr Asp Ala
                485                 490                 495

Ala Gly Tyr Ser Val Asp Asn Glu Asn Pro Leu Ser Gly Lys Ala Gly
            500                 505                 510

Gly Val Val Lys Val Thr Tyr Pro Gly Leu Thr Lys Val Leu Ala Leu
        515                 520                 525

Lys Val Asp Asn Ala Glu Thr Ile Lys Lys Glu Leu Gly Leu Ser Leu
530                 535                 540

Thr Glu Pro Leu Met Glu Gln Val Gly Thr Glu Glu Phe Ile Lys Arg
545                 550                 555                 560

Phe Gly Asp Gly Ala Ser Arg Val Val Leu Ser Leu Pro Phe Ala Glu
                565                 570                 575

Gly Ser Ser Ser Val Glu Tyr Ile Asn Asn Trp Glu Gln Ala Lys Ala
            580                 585                 590

Leu Ser Val Glu Leu Glu Ile Asn Phe Glu Thr Arg Gly Lys Arg Gly
        595                 600                 605

Gln Asp Ala Met Tyr Glu Tyr Met Ala Gln Ala Cys Ala Ser Glu Glu
610                 615                 620
```

```
Asp Asp Thr Thr Val Cys Cys Ser Met Ser Tyr Ser Trp Thr Gly Ala
625                 630                 635                 640

Leu Ala Ile Gly Leu Gln Gly Gly Gly Ser Gly Gly Gly Ser Gly
            645                 650                 655

Ser Gly Gly Ser Gly Ala Cys Tyr Cys Arg Ile Pro Ala Cys Ile Ala
            660                 665                 670

Gly Glu Arg Arg Tyr Gly Thr Cys Ile Tyr Gln Gly Arg Leu Trp Ala
        675                 680                 685

Phe Cys Cys Gly Ser Gly Ser His His His His His Lys Asp Glu
    690                 695                 700

Leu
705

<210> SEQ ID NO 67
<211> LENGTH: 778
<212> TYPE: PRT
<213> ORGANISM: Artificial Sequence
<220> FEATURE:
<223> OTHER INFORMATION: Synthetic polypeptide

<400> SEQUENCE: 67

Met Lys Lys Thr Ala Ile Ala Ile Ala Val Ala Leu Ala Gly Phe Ala
1               5                   10                  15

Thr Val Ala Gln Ala Ala Asn Leu Ala Glu Glu Ala Phe Asp Leu Trp
            20                  25                  30

Asn Glu Cys Ala Lys Ala Cys Val Leu Asp Leu Lys Asp Gly Val Arg
        35                  40                  45

Ser Ser Arg Met Ser Val Asp Pro Ala Ile Ala Asp Thr Asn Gly Gln
    50                  55                  60

Gly Val Leu His Tyr Ser Met Val Leu Glu Gly Gly Asn Asp Ala Leu
65                  70                  75                  80

Lys Leu Ala Ile Asp Asn Ala Leu Ser Ile Thr Ser Asp Gly Leu Thr
                85                  90                  95

Ile Arg Leu Glu Gly Gly Val Glu Pro Asn Lys Pro Val Arg Tyr Ser
            100                 105                 110

Tyr Thr Arg Gln Ala Arg Gly Ser Trp Ser Leu Asn Trp Leu Val Pro
        115                 120                 125

Ile Gly His Glu Lys Pro Ser Asn Ile Lys Val Phe Ile His Glu Leu
    130                 135                 140

Asn Ala Gly Asn Gln Leu Ser His Met Ser Pro Ile Tyr Thr Ile Glu
145                 150                 155                 160

Met Gly Asp Glu Leu Leu Ala Lys Leu Ala Arg Asp Ala Thr Phe Phe
                165                 170                 175

Val Arg Ala His Glu Ser Asn Glu Met Gln Pro Thr Leu Ala Ile Ser
            180                 185                 190

His Ala Gly Val Ser Val Val Met Ala Gln Thr Gln Pro Arg Arg Glu
        195                 200                 205

Lys Arg Trp Ser Glu Trp Ala Ser Gly Lys Val Leu Cys Leu Leu Asp
    210                 215                 220

Pro Leu Asp Gly Val Tyr Asn Tyr Leu Ala Gln Gln Arg Cys Asn Leu
225                 230                 235                 240

Asp Asp Thr Trp Glu Gly Lys Ile Tyr Arg Val Leu Ala Gly Asn Pro
                245                 250                 255

Ala Lys His Asp Leu Asp Ile Lys Pro Thr Val Ile Ser His Arg Leu
            260                 265                 270
```

```
His Phe Pro Glu Gly Gly Ser Leu Ala Ala Leu Thr Ala His Gln Ala
            275                 280                 285
Cys His Leu Pro Leu Glu Thr Phe Thr Arg His Arg Gln Pro Arg Gly
290                 295                 300
Trp Glu Gln Leu Glu Gln Cys Gly Tyr Pro Val Gln Arg Leu Val Ala
305                 310                 315                 320
Leu Tyr Leu Ala Ala Arg Leu Ser Trp Asn Gln Val Asp Gln Val Ile
                325                 330                 335
Arg Asn Ala Leu Ala Ser Pro Gly Ser Gly Gly Asp Leu Gly Glu Ala
            340                 345                 350
Ile Arg Glu Gln Pro Glu Gln Ala Arg Leu Ala Leu Thr Leu Ala Ala
        355                 360                 365
Ala Glu Ser Glu Arg Phe Val Arg Gln Gly Thr Gly Asn Asp Glu Ala
    370                 375                 380
Gly Ala Ala Asn Ala Asp Val Val Ser Leu Thr Cys Pro Val Ala Ala
385                 390                 395                 400
Gly Glu Cys Ala Gly Pro Ala Asp Ser Gly Asp Ala Leu Leu Glu Arg
                405                 410                 415
Asn Tyr Pro Thr Gly Ala Glu Phe Leu Gly Asp Gly Gly Asp Val Ser
            420                 425                 430
Phe Ser Thr Arg Gly Ile Phe Pro Lys Gln Tyr Pro Ile Ile Asn Phe
        435                 440                 445
Thr Thr Ala Gly Ala Thr Val Gln Ser Tyr Thr Asn Phe Ile Arg Ala
    450                 455                 460
Val Arg Gly Arg Leu Thr Thr Gly Ala Asp Val Arg His Glu Ile Pro
465                 470                 475                 480
Val Leu Pro Asn Arg Val Gly Leu Pro Ile Asn Gln Arg Phe Ile Leu
                485                 490                 495
Val Glu Leu Ser Asn His Ala Glu Leu Ser Val Thr Leu Ala Leu Asp
            500                 505                 510
Val Thr Asn Ala Tyr Val Val Gly Tyr Arg Ala Gly Asn Ser Ala Tyr
        515                 520                 525
Phe Phe His Pro Asp Asn Gln Glu Asp Ala Glu Ala Ile Thr His Leu
    530                 535                 540
Phe Thr Asp Val Gln Asn Arg Tyr Thr Phe Ala Phe Gly Gly Asn Tyr
545                 550                 555                 560
Asp Arg Leu Glu Gln Leu Ala Gly Asn Leu Arg Glu Asn Ile Glu Leu
                565                 570                 575
Gly Asn Gly Pro Leu Glu Glu Ala Ile Ser Ala Leu Tyr Tyr Tyr Ser
            580                 585                 590
Thr Gly Gly Thr Gln Leu Pro Thr Leu Ala Arg Ser Phe Ile Ile Cys
        595                 600                 605
Ile Gln Met Ile Ser Glu Ala Ala Arg Phe Gln Tyr Ile Glu Gly Glu
    610                 615                 620
Met Arg Thr Arg Ile Arg Tyr Asn Arg Arg Ser Ala Pro Asp Pro Ser
625                 630                 635                 640
Val Ile Thr Leu Glu Asn Ser Trp Gly Arg Leu Ser Thr Ala Ile Gln
                645                 650                 655
Glu Ser Asn Gln Gly Ala Phe Ala Ser Pro Ile Gln Leu Gln Arg Arg
            660                 665                 670
Asn Gly Ser Lys Phe Ser Val Tyr Asp Val Ser Ile Leu Ile Pro Ile
        675                 680                 685
Ile Ala Leu Met Val Tyr Arg Cys Ala Pro Pro Pro Ser Ser Gly Ser
```

```
            690                 695                 700
Glu Glu Asp Asp Thr Thr Val Cys Cys Ser Met Ser Tyr Ser Trp Thr
705                 710                 715                 720

Gly Ala Leu Gly Gly Gly Ser Glu Glu Ser Glu Glu Ser Asp Asp
                725                 730                 735

Asp Met Gly Phe Gly Leu Phe Asp Thr Gly Gly Glu Ser Glu Glu
                740                 745                 750

Ser Asp Asp Met Gly Phe Gly Leu Phe Asp Thr Gly Ser Leu Gln
            755                 760                 765

His His His His His His Lys Asp Glu Leu
            770                 775

<210> SEQ ID NO 68
<211> LENGTH: 712
<212> TYPE: PRT
<213> ORGANISM: Artificial Sequence
<220> FEATURE:
<223> OTHER INFORMATION: Synthetic polypeptide

<400> SEQUENCE: 68

Met Lys Lys Thr Ala Ile Ala Ile Ala Val Ala Leu Ala Gly Phe Ala
1               5                   10                  15

Thr Val Ala Gln Ala Ala Asn Leu Ala Glu Glu Ala Phe Asp Leu Trp
            20                  25                  30

Asn Glu Cys Ala Lys Ala Cys Val Leu Asp Leu Lys Asp Gly Val Arg
        35                  40                  45

Ser Ser Arg Met Ser Val Asp Pro Ala Ile Ala Asp Thr Asn Gly Gln
    50                  55                  60

Gly Val Leu His Tyr Ser Met Val Leu Glu Gly Gly Asn Asp Ala Leu
65                  70                  75                  80

Lys Leu Ala Ile Asp Asn Ala Leu Ser Ile Thr Ser Asp Gly Leu Thr
                85                  90                  95

Ile Arg Leu Glu Gly Gly Val Glu Pro Asn Lys Pro Val Arg Tyr Ser
            100                 105                 110

Tyr Thr Arg Gln Ala Arg Gly Ser Trp Ser Leu Asn Trp Leu Val Pro
        115                 120                 125

Ile Gly His Glu Lys Pro Ser Asn Ile Lys Val Phe Ile His Glu Leu
    130                 135                 140

Asn Ala Gly Asn Gln Leu Ser His Met Ser Pro Ile Tyr Thr Ile Glu
145                 150                 155                 160

Met Gly Asp Glu Leu Leu Ala Lys Leu Ala Arg Asp Ala Thr Phe Phe
                165                 170                 175

Val Arg Ala His Glu Ser Asn Glu Met Gln Pro Thr Leu Ala Ile Ser
            180                 185                 190

His Ala Gly Val Ser Val Val Met Ala Gln Thr Gln Pro Arg Arg Glu
        195                 200                 205

Lys Arg Trp Ser Glu Trp Ala Ser Gly Lys Val Leu Cys Leu Leu Asp
    210                 215                 220

Pro Leu Asp Gly Val Tyr Asn Tyr Leu Ala Gln Gln Arg Cys Asn Leu
225                 230                 235                 240

Asp Asp Thr Trp Glu Gly Lys Ile Tyr Arg Val Leu Ala Gly Asn Pro
                245                 250                 255

Ala Lys His Asp Leu Asp Ile Lys Pro Thr Val Ile Ser His Arg Leu
            260                 265                 270

His Phe Pro Glu Gly Gly Ser Leu Ala Ala Leu Thr Ala His Gln Ala
```

-continued

```
                275                 280                 285
Cys His Leu Pro Leu Glu Thr Phe Thr Arg His Arg Gln Pro Arg Gly
290                 295                 300
Trp Glu Gln Leu Glu Gln Cys Gly Tyr Pro Val Gln Arg Leu Val Ala
305                 310                 315                 320
Leu Tyr Leu Ala Ala Arg Leu Ser Trp Asn Gln Val Asp Gln Val Ile
                325                 330                 335
Arg Asn Ala Leu Ala Ser Pro Gly Ser Gly Gly Asp Leu Gly Glu Ala
                340                 345                 350
Ile Arg Glu Gln Pro Glu Gln Ala Arg Leu Ala Leu Thr Leu Ala Ala
                355                 360                 365
Ala Glu Ser Glu Arg Phe Val Arg Gln Gly Thr Gly Asn Asp Glu Ala
                370                 375                 380
Gly Ala Ala Asn Ala Asp Val Val Ser Leu Thr Cys Pro Val Ala Ala
385                 390                 395                 400
Gly Glu Cys Ala Gly Pro Ala Asp Ser Gly Asp Ala Leu Leu Glu Arg
                405                 410                 415
Asn Tyr Pro Thr Gly Ala Glu Phe Leu Gly Asp Gly Asp Val Ser
                420                 425                 430
Phe Ser Thr Arg Gly Thr Gln Asn Trp Thr Val Glu Arg Leu Leu Gln
                435                 440                 445
Ala His Arg Gln Leu Glu Glu Arg Gly Tyr Val Phe Val Gly Tyr His
                450                 455                 460
Gly Thr Phe Leu Glu Ala Ala Gln Ser Ile Val Phe Gly Gly Val Arg
465                 470                 475                 480
Ala Arg Ser Gln Asp Leu Asp Ala Ile Trp Arg Gly Phe Tyr Ile Ala
                485                 490                 495
Gly Asp Pro Ala Leu Ala Tyr Gly Tyr Ala Gln Asp Gln Glu Pro Asp
                500                 505                 510
Ala Arg Gly Arg Ile Arg Asn Gly Ala Leu Leu Arg Val Tyr Val Pro
                515                 520                 525
Arg Ser Ser Leu Pro Gly Phe Tyr Arg Thr Ser Leu Thr Leu Ala Ala
                530                 535                 540
Pro Glu Ala Ala Gly Glu Val Glu Arg Leu Ile Gly His Pro Leu Pro
545                 550                 555                 560
Leu Arg Leu Asp Ala Ile Thr Gly Pro Glu Glu Glu Gly Gly Arg Leu
                565                 570                 575
Glu Thr Ile Leu Gly Trp Pro Leu Ala Glu Arg Thr Val Val Ile Pro
                580                 585                 590
Ser Ala Ile Pro Thr Asp Pro Arg Asn Val Gly Gly Asp Leu Asp Pro
                595                 600                 605
Ser Ser Ile Pro Asp Gln Glu Gln Ala Ile Ser Ala Leu Pro Asp Tyr
                610                 615                 620
Ala Ser Gln Pro Gly Gln Gly Ala Ala Gln Glu Leu Ala Glu Asp
625                 630                 635                 640
Val Val Cys Cys Ser Met Ser Tyr Ala Ile Gly Leu Gln Gly Gly Gly
                645                 650                 655
Gly Ser Gly Gly Ser Gly Ser Gly Gly Ser Gly Ala Cys Tyr Cys
                660                 665                 670
Arg Ile Pro Ala Cys Ile Ala Gly Glu Arg Arg Tyr Gly Thr Cys Ile
                675                 680                 685
Tyr Gln Gly Arg Leu Trp Ala Phe Cys Cys Gly Ser Gly Ser His His
                690                 695                 700
```

His His His His Lys Asp Glu Leu
705                 710

<210> SEQ ID NO 69
<211> LENGTH: 2088
<212> TYPE: DNA
<213> ORGANISM: Artificial Sequence
<220> FEATURE:
<223> OTHER INFORMATION: Synthetic polynucleotide

<400> SEQUENCE: 69

```
atgaaaaaga cagctatcgc gattgcagtg gcactggctg gtttcgctac cgtagcgcag      60
gccgcgaatt tggccgaaga agctttcgac ctctggaacg aatgcgccaa agcctgcgtg     120
ctcgacctca aggacggcgt gcgttccagc cgcatgagcg tcgacccggc catcgccgac     180
accaacggcc agggcgtgct gcactactcc atggtcctgg agggcggcaa cgacgcgctc     240
aagctggcca tcgacaacgc cctcagcatc accagcgacg gcctgaccat ccgcctcgaa     300
ggcggcgtcg agccgaacaa gccggtgcgc tacagctaca cgcgccaggc gcgcggcagt     360
tggtcgctga actggctggt accgatcggc cacgagaagc cctcgaacat caaggtgttc     420
atccacgaac tgaacgccgg caaccagctc agccacatgt cgccgatcta caccatcgag     480
atgggcgacg agttgctggc gaagctggcg cgcgatgcca ccttcttcgt cagggcgcac     540
gagagcaacg agatgcagcc gacgctcgcc atcagccatg ccggggtcag cgtggtcatg     600
gcccagaccc agccgcgccg ggaaaagcgc tggagcgaat gggccagcgg caaggtgttg     660
tgcctgctcg acccgctgga cggggtctac aactacctcg cccagcaacg ctgcaacctc     720
gacgatacct gggaaggcaa gatctaccgg gtgctcgccg gcaacccggc gaagcatgac     780
ctggacatca aacccacggt catcagtcat cgcctgcact ttcccgaggg cggcagcctg     840
gccgcgctga ccgcgcacca ggcttgccac ctgccgctgg agactttcac ccgtcatcgc     900
cagccgcgcg gctgggaaca actggagcag tgcggctatc cggtgcagcg gctggtcgcc     960
ctctacctgg cggcgcggct gtcgtggaac caggtcgacc aggtgatccg caacgccctg    1020
gccagccccg gcagcggcgg cgacctgggc gaagcgatcc gcgagcagcc ggagcaggcc    1080
cgtctggccc tgaccctggc cgccgccgag agcgagcgct tcgtccggca gggcaccggc    1140
aacgacgagg ccgcgcgggc caacgccgac gtggtgagcc tgacctgccc ggtcgccgcc    1200
ggtgaatgcg cgggcccggc ggacagcggc gacgccctgc tggagcgcaa ctatcccact    1260
ggcgcggagt cctcggcga cggcggcgac gtcggcaccg gtggcgctga tgatgttgtt    1320
gattcttcta aatcttttgt gatggaaaac ttttcttcgt accacgggac taaacctggt    1380
tatgtagatt ccattcaaaa aggtatacaa aagccaaaat ctggtacaca aggaaattat    1440
gacgatgatt ggaaagggtt ttatagtacc gacaataaat acgacgctgc gggatactct    1500
gtagataatg aaaacccgct ctctggaaaa gctggaggcg tggtcaaagt gacgtatcca    1560
ggactgacga aggttctcgc actaaaagtg gataatgccg aaactattaa gaaagagtta    1620
ggttttaagtc tcactgaacc gttgatggag caagtcggaa cggaagagtt tatcaaaagg    1680
ttcggtgatg tgcttcgcg tgtagtgctc agccttccct tcgctgaggg gagttctagc    1740
gttgaatata ttaataactg gaacaggcg aaagcgttaa gcgtagaact tgagattaat    1800
tttgaaaccc gtggaaaacg tggccaagat gcgatgtatg agtatatggc tcaagcctgt    1860
gcagaggatg tcgtgtgctg ctcgatgtcc tacgcaattg gcctgcaggg cggtggcggt    1920
tctggcggcg gctccggtag cggcggctcc ggtgcgtgct actgtcgtat tccggcttgc    1980
```

```
atcgcgggtg aacgtcgtta cggcacttgt atttatcaag gccgcctgtg ggcattctgc    2040
tgtggttctg gttcccatca ccatcaccat cacaaggacg agctgtaa                 2088

<210> SEQ ID NO 70
<211> LENGTH: 2310
<212> TYPE: DNA
<213> ORGANISM: Artificial Sequence
<220> FEATURE:
<223> OTHER INFORMATION: Synthetic polynucleotide

<400> SEQUENCE: 70
atgaaaaaga cagctatcgc gattgcagtg gcactggctg gtttcgctac cgtagcgcag      60
gccgcgaatt tggccgaaga agctttcgac ctctggaacg aatgcgccaa agcctgcgtg     120
ctcgacctca aggacggcgt gcgttccagc cgcatgagcg tcgacccggc catcgccgac     180
accaacggcc agggcgtgct gcactactcc atggtcctgg agggcggcaa cgacgcgctc     240
aagctggcca tcgacaacgc cctcagcatc accagcgacg gcctgaccat ccgcctcgaa     300
ggcggcgtcg agccgaacaa gccggtgcgc tacagctaca cgcgccaggc gcgcggcagt     360
tggtcgctga actggctggt accgatcggc acgagaagcc cctcgaacat caaggtgttc     420
atccacgaac tgaacgccgg caaccagctc agccacatgt cgccgatcta caccatcgag     480
atgggcgacg agttgctggc gaagctggcg cgcgatgcca ccttcttcgt cagggcgcac     540
gagagcaacg agatgcagcc gacgctcgcc atcagccatg ccggggtcag cgtggtcatg     600
gcccagaccc agccgcgccg ggaaaagcgc tggagcgaat gggccagcgg caaggtgttg     660
tgcctgctcg acccgctgga cggggtctac aactacctcg cccagcaacg ctgcaacctc     720
gacgatacct gggaaggcaa gatctaccgg gtgctcgccg gcaacccggc gaagcatgac     780
ctggacatca aacccacggt catcagtcat cgcctgcact ttcccgaggg cggcagcctg     840
gccgcgctga ccgcgcacca ggcttgccac ctgccgctgg agactttcac ccgtcatcgc     900
cagccgcgcg gctgggaaca actggagcag tgcggctatc cggtgcagcg gctggtcgcc     960
ctctacctgg cggcgcggct gtcgtggaac caggtcgacc aggtgatccg caacgccctg    1020
gccagccccg gcagcggcgg cgacctgggc gaagcgatcc gcgagcagcc ggagcaggcc    1080
cgtctggccc tgaccctggc cgccgccgag agcgagcgct tcgtccggca gggcaccggc    1140
aacgacgagg ccggcgcggc caacgccgac gtggtgagcc tgacctgccc ggtcgccgcc    1200
ggtgaatgcg cgggcccggc ggacagcggc gacgccctgc tggagcgcaa ctatcccact    1260
ggcgcggagt tcctcggcga cggcggcgac gtcagcttca gcaccgcgg catattcccc    1320 aaacaatacc caattataaa ctttaccaca gcgggtgcca ctgtgcaaag ctacacaaac    1380
tttatcagag ctgttcgcgg tcgtttaaca actggagctg atgtgagaca tgaaatacca    1440
gtgttgccaa acagagttgg tttgcctata aaccaacggt ttatttagt tgaactctca     1500 aatcatgcag agctttctgt tacattagcc ctggatgtca ccaatgcata tgtggtcggc    1560
taccgtgctg gaaatagcgc atatttcttt catcctgaca atcaggaaga tgcagaagca    1620
atcactcatc ttttcactga tgttcaaaat cgatatacat cgcctttgg tggtaattat    1680 gatagacttg aacaacttgc tggtaatctg agagaaaata tcgagttggg aaatggtcca    1740
ctagaggagg ctatctcagc gctttattat tacagtactg gtggcactca gcttccaact    1800
ctggctcgtt cctttataat ttgcatccaa atgatttcag aagcagcaag attccaatat    1860
attgagggag aaatgcgcac gagaattagg tacaaccgga gatctgcacc agatcctagc    1920
```

```
gtaattacac ttgagaatag ttgggggaga ctttccactg caattcaaga gtctaaccaa   1980
ggagcctttg ctagtccaat tcaactgcaa agacgtaatg gttccaaatt cagtgtgtac   2040
gatgtgagta tattaatccc tatcatagct ctcatggtgt atagatgcgc acctccacca   2100
tcgtcaggat ccgaagatgt ggtgtgttgt agcatgtcgt acggcggtgg cggctcagag   2160
gaatccgaag aatccgatga tgacatgggt tttggtctgt tcgacaccgg tggtgaggag   2220
tccgaggaat ccgacgacga tatgggcttc ggcctgtttg acaccggttc tctgcagcat   2280
caccatcacc atcacaagga cgagctgtaa                                    2310
```

<210> SEQ ID NO 71
<211> LENGTH: 2118
<212> TYPE: DNA
<213> ORGANISM: Artificial Sequence
<220> FEATURE:
<223> OTHER INFORMATION: Synthetic polynucleotide

<400> SEQUENCE: 71

```
atgaaaaaga cagctatcgc gattgcagtg gcactggctg gtttcgctac cgtagcgcag     60
gccgcgaatt tggccgaaga agctttcgac ctctggaacg aatgcgccaa agcctgcgtg    120
ctcgacctca aggacggcgt gcgttccagc cgcatgagcg tcgacccggc catcgccgac    180
accaacggcc agggcgtgct gcactactcc atggtcctgg agggcggcaa cgacgcgctc    240
aagctggcca tcgacaacgc cctcagcatc accagcgacg gcctgaccat ccgcctcgaa    300
ggcggcgtcg agccgaacaa gccggtgcgc tacagctaca cgcgccaggc gcgcggcagt    360
tggtcgctga actggctggt accgatcggc acgagaagc cctcgaacat caaggtgttc    420
atccacgaac tgaacgccgg caaccagctc agccacatgt cgccgatcta caccatcgag    480
atgggcgacg agttgctggc gaagctggcg cgcgatgcca ccttcttcgt cagggcgcac    540
gagagcaacg agatgcagcc gacgctcgcc atcagccatg ccggggtcag cgtggtcatg    600
gcccagaccc agccgcgccg ggaaaagcgc tggagcgaat gggccagcgg caaggtgttg    660
tgcctgctcg acccgctgga cggggtctac aactacctcg cccagcaacg ctgcaacctc    720
gacgatacct gggaaggcaa gatctaccgg gtgctcgccg gcaacccggc gaagcatgac    780
ctggacatca aacccacggt catcagtcat cgcctgcact ttcccgaggg cggcagcctg    840
gccgcgctga ccgcgcacca ggcttgccac ctgccgctgg agactttcac ccgtcatcgc    900
cagccgcgcg gctgggaaca actggagcag tgcggctatc cggtgcagcg gctggtcgcc    960
ctctacctgg cggcgcggct gtcgtggaac caggtcgacc aggtgatccg caacgccctg   1020
gccagccccg gcagcggcgg cgacctgggc gaagcgatcc gcgagcagcc ggagcaggcc   1080
cgtctggccc tgaccctggc cgccgccgag agcgagcgct tcgtccggca gggcaccggc   1140
aacgacgagg ccggcgcggc caacgccgac gtggtgagcc tgacctgccc ggtcgccgcc   1200
ggtgaatgcg cggccccggc ggacagcggc gacgccctgc tggagcgcaa ctatcccact   1260
ggcgcggagt tcctcggcga cggcggcgac gtcggcaccg gtggcgctga tgatgttgtt   1320
gattcttcta aatcttttgt gatggaaaac ttttcttcgt accacgggac taaacctggt   1380
tatgtagatt ccattcaaaa aggtatacaa aagccaaaat ctggtacaca aggaaaattat   1440 gacgatgatt ggaaagggtt ttatagtacc gacaataaat acgacgctgc gggatactct   1500
gtagataatg aaaacccgct ctctggaaaa gctggaggcg tggtcaaagt gacgtatcca   1560
ggactgacga aggttctcgc actaaaagtg ataatgccg aaactattaa gaaagagtta   1620
ggtttaagtc tcactgaacc gttgatggag caagtcggaa cggaagagtt tatcaaaagg   1680
```

```
ttcggtgatg gtgcttcgcg tgtagtgctc agccttccct tcgctgaggg gagttctagc    1740
gttgaatata ttaataactg ggaacaggcg aaagcgttaa gcgtagaact tgagattaat    1800
tttgaaaccc gtggaaaacg tggccaagat gcgatgtatg agtatatggc tcaggcctgt    1860
gcatctgaag aagatgacac gaccgtatgt tgctctatga gctactcctg gactggtgcg    1920
ctggcaattg gcctgcaggg cggtggcggt tctggcggcg ctccggtag cggcggctcc     1980 ggtgcgtgct actgtcgtat tccggcttgc atcgcgggtg aacgtcgtta cggcacttgt    2040
atttatcaag gccgcctgtg ggcattctgc tgtggttctg gttcccatca ccatcaccat    2100
cacaaggacg agctgtaa                                                  2118

<210> SEQ ID NO 72
<211> LENGTH: 2337
<212> TYPE: DNA
<213> ORGANISM: Artificial Sequence
<220> FEATURE:
<223> OTHER INFORMATION: Synthetic polynucleotide

<400> SEQUENCE: 72
atgaaaaaga cagctatcgc gattgcagtg gcactggctg gtttcgctac cgtagcgcag      60
gccgcgaatt tggccgaaga agctttcgac ctctggaacg aatgcgccaa agcctgcgtg     120
ctcgacctca aggacggcgt gcgttccagc cgcatgagcg tcgacccggc catcgccgac     180
accaacggcc agggcgtgct gcactactcc atggtcctgg agggcggcaa cgacgcgctc     240
aagctggcca tcgacaacgc cctcagcatc accagcgacg gcctgaccat ccgcctcgaa     300
ggcggcgtcg agccgaacaa gccggtgcgc tacagctaca cgcgccaggc gcgcggcagt     360
tggtcgctga actggctggt accgatcggc cacgagaagc cctcgaacat caaggtgttc     420
atccacgaac tgaacgccgg caaccagctc agccacatgt cgccgatcta caccatcgag     480
atgggcgacg agttgctggc gaagctggcg cgcgatgcca ccttcttcgt cagggcgcac     540
gagagcaacg agatgcagcc gacgctcgcc atcagccatg ccggggtcag cgtggtcatg     600
gcccagaccc agccgcgccg ggaaaagcgc tggagcgaat gggccagcgg caaggtgttg     660
tgcctgctcg acccgctgga cggggtctac aactacctcg cccagcaacg ctgcaacctc     720
gacgatacct gggaaggcaa gatctaccgg gtgctcgccg gcaacccggc gaagcatgac     780
ctggacatca aacccacggt catcagtcat cgcctgcact ttcccgaggg cggcagcctg     840
gccgcgctga ccgcgcacca ggcttgccac ctgccgctgg agactttcac ccgtcatcgc     900
cagccgcgcg gctgggaaca actggagcag tgcggctatc cggtgcagcg gctggtcgcc     960
ctctacctgg cggcgcggct gtcgtggaac caggtcgacc aggtgatccg caacgccctg    1020 gccagcccg cagcggcgg cgacctgggc gaagcgatcc gcgagcagcc ggagcaggcc    1080
cgtctggccc tgaccctggc cgccgccgag agcgagcgct tcgtccggca gggcaccggc    1140
aacgacgagg ccgcgcgcgg caacgccgac gtggtgagcc tgacctgccc ggtcgccgcc    1200
ggtgaatgcg cgggcccggc ggacagcggc gacgccctgc tggagcgcaa ctatcccact    1260
ggcgcggagt tcctcggcga cggcggcgac gtcagcttca gcaccgcgg catattcccc    1320 aaacaatacc caattataaa ctttaccaca gcgggtgcca ctgtgcaaag ctacacaaac    1380
tttatcagag ctgttcgcgg tcgtttaaca actggagctg atgtgagaca tgaaataccca    1440 gtgttgccaa acagagttgg tttgcctata aaccaacggt ttattttagt tgaactctca    1500
aatcatgcag agctttctgt tacattagcc ctggatgtca ccaatgcata tgtggtcggc    1560
```

```
taccgtgctg gaaatagcgc atatttcttt catcctgaca atcaggaaga tgcagaagca    1620
atcactcatc ttttcactga tgttcaaaat cgatatacat tcgcctttgg tggtaattat    1680
gatagacttg aacaacttgc tggtaatctg agagaaaata tcgagttggg aaatggtcca    1740
ctagaggagg ctatctcagc gctttattat tacagtactg gtggcactca gcttccaact    1800
ctggctcgtt cctttataat ttgcatccaa atgatttcag aagcagcaag attccaatat    1860
attgagggag aaatgcgcac gagaattagg tacaaccgga gatctgcacc agatcctagc    1920
gtaattacac ttgagaatag ttgggggaga cttccactg caattcaaga gtctaaccaa    1980 ggagccttg ctagtccaat tcaactgcaa agacgtaatg gttccaaatt cagtgtgtac    2040
gatgtgagta tattaatccc tatcatagct ctcatggtgt atagatgcgc acctccacca    2100
tcgtcaggat ccgaagaaga tgacacgacc gtatgttgct ctatgagcta ctcctggact    2160
ggtgcgctgg gcggtggcgg ctcagaggaa tccgaagaat ccgatgatga catgggtttt    2220
ggtctgttcg acaccggtgg tgaggagtcc gaggaatccg acgacgatat gggcttcggc    2280
ctgtttgaca ccggttctct gcagcatcac catcaccatc acaaggacga gctgtaa      2337
```

<210> SEQ ID NO 73
<211> LENGTH: 2139
<212> TYPE: DNA
<213> ORGANISM: Artificial Sequence
<220> FEATURE:
<223> OTHER INFORMATION: Synthetic polynucleotide

<400> SEQUENCE: 73

```
atgaaaaaga cagctatcgc gattgcagtg gcactggctg gtttcgctac cgtagcgcag      60
gccgcgaatt tggccgaaga agctttcgac ctctggaacg aatgcgccaa agcctgcgtg     120
ctcgacctca aggacggcgt gcgttccagc cgcatgagcg tcgacccggc catcgccgac     180
accaacggcc agggcgtgct gcactactcc atggtcctgg agggcggcaa cgacgcgctc     240
aagctggcca tcgacaacgc cctcagcatc accagcgacg gcctgaccat ccgcctcgaa     300
ggcggcgtcg agccgaacaa gccggtgcgc tacagctaca cgcgccaggc gcgcggcagt     360
tggtcgctga actggctggt accgatcggc acgagaagc cctcgaacat caaggtgttc     420
atccacgaac tgaacgccgg caaccagctc agccacatgt cgccgatcta ccatcgag     480 atgggcgaca gttgctggcg gaagctggcg cgcgatgcca ccttcttcgt cagggcgcac     540
gagagcaacg agatgcagcc gacgctcgcc atcagccatg ccggggtcag cgtggtcatg     600
gcccagaccc agccgcgccg ggaaaagcgc tggagcgaat gggccagcgg caaggtgttg     660
tgcctgctcg acccgctgga cggggtctac aactacctcg cccagcaacg ctgcaacctc     720
gacgatacct gggaaggcaa gatctaccgg gtgctcgccg gcaacccggc gaagcatgac     780
ctggacatca acccacggt catcagtcat cgcctgcact ttcccgaggg cggcagcctg     840
gccgcgctga ccgcgcacca ggcttgccac ctgccgctgg agactttcac ccgtcatcgc     900
cagccgcgcg gctgggaaca actggagcag tgcggctatc cggtgcagcg gctggtcgcc     960
ctctacctgg cggcgcggct gtcgtggaac caggtcgacc aggtgatccg caacgccctg    1020
gccagccccg gcagcggcgg cgacctgggc gaagcgatcc gcgagcagcc ggagcaggcc    1080
cgtctggccc tgaccctggc cgccgccgag agcgagcgct tcgtccggca gggcaccggc    1140
aacgacgagg ccggcgcggc caacgccgac gtggtgagcc tgacctgccc ggtcgccgcc    1200
ggtgaatgcg cggccccggc ggacagcggc gacgccctgc tggagcgcaa ctatcccact    1260
ggcgcggagt tcctcggcga cggcggcgac gtcagcttca gcacccgcgg cacgcagaac    1320
```

```
tggacggtgg agcggctgct ccaggcgcac cgccaactgg aggagcgcgg ctatgtgttc    1380
gtcggctacc acggcaccttt cctcgaagcg gcgcaaagca tcgtcttcgg cggggtgcgc    1440
gcgcgcagcc aggacctcga cgcgatctgg cgcggtttct atatcgccgg cgatccggcg    1500
ctggcctacg gctacgccca ggaccaggaa cccgacgcac gcggccggat ccgcaacggt    1560
gccctgctgc gggtctatgt gccgcgctcg agcctgccgg gcttctaccg caccagcctg    1620
accctggccg cgccggaggc ggcgggcgag gtcgaacggc tgatcggcca tccgctgccg    1680
ctgcgcctgg acgccatcac cggccccgag gaggaaggcg ggcgcctgga gaccattctc    1740
ggctggccgc tggccgagcg caccgtggtg attccctcgg cgatccccac cgacccgcgc    1800
aacgtcggcg gcgacctcga cccgtccagc atcccggacc aagaacaggc gatcagcgcc    1860
ctgccggact acgccagcca gcccgggcaa ggagcggccg cgcaggagct agcggaggat    1920
gtcgtgtgct gctcgatgtc ctacgcaatt ggcctgcagg gcggtggcgg ttctggcggc    1980
ggctccggta gcggcggctc cggtgcgtgc tactgtcgta ttccggcttg catcgcgggt    2040
gaacgtcgtt acggcacttg tatttatcaa ggccgcctgt gggcattctg ctgtggttct    2100
ggttcccatc accatcacca tcacaaggac gagctgtaa                           2139
```

```
<210> SEQ ID NO 74
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 74

Arg Arg Arg Arg Arg Arg Arg Arg Arg
1               5

<210> SEQ ID NO 75
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 75

Arg Lys Lys Arg Arg Gln Arg Arg Arg
1               5

<210> SEQ ID NO 76
<211> LENGTH: 13
<212> TYPE: PRT
<213> ORGANISM: Artificial Sequence
<220> FEATURE:
<223> OTHER INFORMATION: Synthetic polynucleotide

<400> SEQUENCE: 76

Gly Arg Lys Lys Arg Arg Gln Arg Arg Arg Pro Pro Gln
1               5                   10

<210> SEQ ID NO 77
<211> LENGTH: 21
<212> TYPE: PRT
<213> ORGANISM: Artificial Sequence
<220> FEATURE:
<223> OTHER INFORMATION: Synthetic polpeptide

<400> SEQUENCE: 77

Lys Glu Thr Trp Trp Glu Thr Trp Trp Thr Glu Trp Ser Gln Pro Lys
```

```
1               5                  10                 15

Lys Lys Arg Lys Val
            20

<210> SEQ ID NO 78
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 78

Arg Gln Ile Lys Ile Trp Phe Gln Asn Arg Arg Met Lys Trp Lys Lys
1               5                  10                 15

<210> SEQ ID NO 79
<211> LENGTH: 27
<212> TYPE: PRT
<213> ORGANISM: Artificial Sequence
<220> FEATURE:
<223> OTHER INFORMATION: Synthetic polypeptide

<400> SEQUENCE: 79

Gly Trp Thr Leu Asn Ser Ala Gly Tyr Leu Leu Gly Lys Ile Asn Leu
1               5                  10                 15

Lys Ala Leu Ala Ala Leu Ala Lys Lys Ile Leu
            20                  25

<210> SEQ ID NO 80
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 80

Val Gln Arg Lys Arg Gln Lys Leu Met Pro
1               5                  10

<210> SEQ ID NO 81
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 81

Ser Lys Lys Lys Lys Ile Lys Val
1               5

<210> SEQ ID NO 82
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 82

Gly Arg Lys Arg Lys Lys Arg Thr
1               5

<210> SEQ ID NO 83
<211> LENGTH: 43
<212> TYPE: DNA
<213> ORGANISM: Artificial Sequence
<220> FEATURE:
```

```
<223> OTHER INFORMATION: Primer

<400> SEQUENCE: 83
tcgagctcaa gcttcgccac catggcgcct atcggctcag tag          43

<210> SEQ ID NO 84
<211> LENGTH: 38
<212> TYPE: DNA
<213> ORGANISM: Artificial Sequence
<220> FEATURE:
<223> OTHER INFORMATION: Primer

<400> SEQUENCE: 84
tggatcccgg gccctctaga ctcgagcggc cgccactg               38

<210> SEQ ID NO 85
<211> LENGTH: 72
<212> TYPE: DNA
<213> ORGANISM: Artificial Sequence
<220> FEATURE:
<223> OTHER INFORMATION: Primer

<400> SEQUENCE: 85
ttcccctcta gaaataattt tgtttaactt taagaaggag ataccatg aaaaagacag    60 ctatcgcgat tg                                                      72

<210> SEQ ID NO 86
<211> LENGTH: 70
<212> TYPE: DNA
<213> ORGANISM: Artificial Sequence
<220> FEATURE:
<223> OTHER INFORMATION: Primer

<400> SEQUENCE: 86
tcgagcagca cacgacatcc tccgctagct cctgcgcggc cgctccttgc ccgggctggc  60
tggcgtagtc                                                         70

<210> SEQ ID NO 87
<211> LENGTH: 70
<212> TYPE: DNA
<213> ORGANISM: Artificial Sequence
<220> FEATURE:
<223> OTHER INFORMATION: Primer

<400> SEQUENCE: 87
cgtccttgtg atggtgatgg tgatgctgca ggccaattgc gtaggacatc gagcagcaca  60
cgacatcctc                                                         70

<210> SEQ ID NO 88
<211> LENGTH: 43
<212> TYPE: DNA
<213> ORGANISM: Artificial Sequence
<220> FEATURE:
<223> OTHER INFORMATION: Primer

<400> SEQUENCE: 88
acggagctcg aattcttaca gctcgtcctt gtgatggtga tgg          43

<210> SEQ ID NO 89
<211> LENGTH: 21
<212> TYPE: DNA
<213> ORGANISM: Artificial Sequence
<220> FEATURE:
<223> OTHER INFORMATION: Primer
```

<400> SEQUENCE: 89
ctcagcttcc tttcgggctt t                                              21

<210> SEQ ID NO 90
<211> LENGTH: 63
<212> TYPE: DNA
<213> ORGANISM: Artificial Sequence
<220> FEATURE:
<223> OTHER INFORMATION: Primer

<400> SEQUENCE: 90
ggccgcctgt gggcattctg ctgtggttct ggttcccatc accatcacca tcacaaggac    60
gag                                                                  63

<210> SEQ ID NO 91
<211> LENGTH: 62
<212> TYPE: DNA
<213> ORGANISM: Artificial Sequence
<220> FEATURE:
<223> OTHER INFORMATION: Primer

<400> SEQUENCE: 91
tgcatcgcgg gtgaacgtcg ttacggcact tgtatttatc aaggccgcct gtgggcattc    60
tg                                                                   62

<210> SEQ ID NO 92
<211> LENGTH: 63
<212> TYPE: DNA
<213> ORGANISM: Artificial Sequence
<220> FEATURE:
<223> OTHER INFORMATION: Primer

<400> SEQUENCE: 92
cggtagcggc ggctccggtg cgtgctactg tcgtattccg gcttgcatcg cgggtgaacg    60
tcg                                                                  63

<210> SEQ ID NO 93
<211> LENGTH: 56
<212> TYPE: DNA
<213> ORGANISM: Artificial Sequence
<220> FEATURE:
<223> OTHER INFORMATION: Primer

<400> SEQUENCE: 93
attggcctgc agggcggtgg cggttctggc ggcggctccg gtagcggcgg ctccgg        56

<210> SEQ ID NO 94
<211> LENGTH: 47
<212> TYPE: DNA
<213> ORGANISM: Artificial Sequence
<220> FEATURE:
<223> OTHER INFORMATION: Primer

<400> SEQUENCE: 94
aaatttgacg tcggcaccgg tggcgctgat gatgttgttg attcttc                  47

<210> SEQ ID NO 95
<211> LENGTH: 71
<212> TYPE: DNA
<213> ORGANISM: Artificial Sequence
<220> FEATURE:
<223> OTHER INFORMATION: Primer

<400> SEQUENCE: 95
aaatttcaat tgcgtaggac atcgagcagc acacgacatc ctctgcacag gcttgagcca    60
tatactcata c                                                         71

<210> SEQ ID NO 96
<211> LENGTH: 47
<212> TYPE: DNA
<213> ORGANISM: Artificial Sequence
<220> FEATURE:
<223> OTHER INFORMATION: Primer

<400> SEQUENCE: 96
aaatttgacg tcggcaccgg tggcgctgat gatgttgttg attcttc                   47

<210> SEQ ID NO 97
<211> LENGTH: 39
<212> TYPE: DNA
<213> ORGANISM: Artificial Sequence
<220> FEATURE:
<223> OTHER INFORMATION: Primer

<400> SEQUENCE: 97
ttgccgcgga catcgagcgg cacacgacat cctctgcac                            39

<210> SEQ ID NO 98
<211> LENGTH: 36
<212> TYPE: DNA
<213> ORGANISM: Artificial Sequence
<220> FEATURE:
<223> OTHER INFORMATION: Primer

<400> SEQUENCE: 98
accgccctgc aggccaattg ccgcggacat cgagcg                               36

<210> SEQ ID NO 99
<211> LENGTH: 47
<212> TYPE: DNA
<213> ORGANISM: Artificial Sequence
<220> FEATURE:
<223> OTHER INFORMATION: Primer

<400> SEQUENCE: 99
aaatttgacg tcggcaccgg tggcgctgat gatgttgttg attcttc                   47

<210> SEQ ID NO 100
<211> LENGTH: 43
<212> TYPE: DNA
<213> ORGANISM: Artificial Sequence
<220> FEATURE:
<223> OTHER INFORMATION: Primer

<400> SEQUENCE: 100
accgccctgc aggccaattg ctgcacaggc ttgagccata tac                       43

<210> SEQ ID NO 101
<211> LENGTH: 21
<212> TYPE: DNA
<213> ORGANISM: Artificial Sequence
<220> FEATURE:
<223> OTHER INFORMATION: Primer

<400> SEQUENCE: 101
ctcagcttcc tttcgggctt t                                               21

```
<210> SEQ ID NO 102
<211> LENGTH: 65
<212> TYPE: DNA
<213> ORGANISM: Artificial Sequence
<220> FEATURE:
<223> OTHER INFORMATION: Primer

<400> SEQUENCE: 102
gaccgtatgt tgctctatga gctactcctg gactggtgcg ctggcaattg gcctgcaggg    60
cggtg                                                               65

<210> SEQ ID NO 103
<211> LENGTH: 60
<212> TYPE: DNA
<213> ORGANISM: Artificial Sequence
<220> FEATURE:
<223> OTHER INFORMATION: Primer

<400> SEQUENCE: 103
tatatggctc aggcctgtgc atctgaagaa gatgacacga ccgtatgttg ctctatgagc    60

<210> SEQ ID NO 104
<211> LENGTH: 33
<212> TYPE: DNA
<213> ORGANISM: Artificial Sequence
<220> FEATURE:
<223> OTHER INFORMATION: Primer

<400> SEQUENCE: 104
aaatttccgc ggcatattcc ccaaacaata ccc                                33

<210> SEQ ID NO 105
<211> LENGTH: 34
<212> TYPE: DNA
<213> ORGANISM: Artificial Sequence
<220> FEATURE:
<223> OTHER INFORMATION: Primer

<400> SEQUENCE: 105
aaatttcaat tgcaaactgt gacgatggtg gagg                               34

<210> SEQ ID NO 106
<211> LENGTH: 33
<212> TYPE: DNA
<213> ORGANISM: Artificial Sequence
<220> FEATURE:
<223> OTHER INFORMATION: Primer

<400> SEQUENCE: 106
aaatttccgc ggcatattcc ccaaacaata ccc                                33

<210> SEQ ID NO 107
<211> LENGTH: 57
<212> TYPE: DNA
<213> ORGANISM: Artificial Sequence
<220> FEATURE:
<223> OTHER INFORMATION: Primer

<400> SEQUENCE: 107
cgtacgacat gctacaacac accacatctt cggatcctga cgatggtgga ggtgcgc      57

<210> SEQ ID NO 108
<211> LENGTH: 65
<212> TYPE: DNA
<213> ORGANISM: Artificial Sequence
<220> FEATURE:
```

<223> OTHER INFORMATION: Primer

<400> SEQUENCE: 108
catgtcatca tcggattctt cggattcctc tgagccgcca ccgccgtacg acatgctaca    60
acaca    65

<210> SEQ ID NO 109
<211> LENGTH: 63
<212> TYPE: DNA
<213> ORGANISM: Artificial Sequence
<220> FEATURE:
<223> OTHER INFORMATION: Primer

<400> SEQUENCE: 109
tcgtcaggat ccgaggatgt cgtgtgccgc tcgatgtccg cgggcggtgg cggctcagag    60
gaa    63

<210> SEQ ID NO 110
<211> LENGTH: 43
<212> TYPE: DNA
<213> ORGANISM: Artificial Sequence
<220> FEATURE:
<223> OTHER INFORMATION: Primer

<400> SEQUENCE: 110
acggagctcg aattcttaca gctcgtcctt gtgatggtga tgg    43

<210> SEQ ID NO 111
<211> LENGTH: 21
<212> TYPE: DNA
<213> ORGANISM: Artificial Sequence
<220> FEATURE:
<223> OTHER INFORMATION: Primer

<400> SEQUENCE: 111
ctcagcttcc tttcgggctt t    21

<210> SEQ ID NO 112
<211> LENGTH: 57
<212> TYPE: DNA
<213> ORGANISM: Artificial Sequence
<220> FEATURE:
<223> OTHER INFORMATION: Primer

<400> SEQUENCE: 112
tatgttgctc tatgagctac tcctggactg gtgcgctggg cggtggcggc tcagagg    57

<210> SEQ ID NO 113
<211> LENGTH: 57
<212> TYPE: DNA
<213> ORGANISM: Artificial Sequence
<220> FEATURE:
<223> OTHER INFORMATION: Primer

<400> SEQUENCE: 113
ccatcgtcag gatccgaaga agatgacacg accgtatgtt gctctatgag ctactcc    57

<210> SEQ ID NO 114
<211> LENGTH: 18
<212> TYPE: DNA
<213> ORGANISM: Artificial Sequence
<220> FEATURE:
<223> OTHER INFORMATION: Primer

<400> SEQUENCE: 114
tagaaggcac agtcgagg                                                    18

<210> SEQ ID NO 115
<211> LENGTH: 65
<212> TYPE: DNA
<213> ORGANISM: Artificial Sequence
<220> FEATURE:
<223> OTHER INFORMATION: Primer

<400> SEQUENCE: 115
aagacgtagt atgttgctct atgagttaca cttggaccgg gacaccggta tcaggcaatt     60
tgaag                                                                 65

<210> SEQ ID NO 116
<211> LENGTH: 52
<212> TYPE: DNA
<213> ORGANISM: Artificial Sequence
<220> FEATURE:
<223> OTHER INFORMATION: Primer

<400> SEQUENCE: 116
ctacaaggac gctagcggtg ctgacacaga agacgtagta tgttgctcta tg             52

<210> SEQ ID NO 117
<211> LENGTH: 70
<212> TYPE: DNA
<213> ORGANISM: Artificial Sequence
<220> FEATURE:
<223> OTHER INFORMATION: Primer

<400> SEQUENCE: 117
tgacacgacc gtatgttgct ctatgagcta ctcctggact ggtgcgctga caccggtatc     60
aggcaatttg                                                            70

<210> SEQ ID NO 118
<211> LENGTH: 46
<212> TYPE: DNA
<213> ORGANISM: Artificial Sequence
<220> FEATURE:
<223> OTHER INFORMATION: Primer

<400> SEQUENCE: 118
acaaggacgc tagctctgaa gaagatgaca cgaccgtatg ttgctc                    46

<210> SEQ ID NO 119
<211> LENGTH: 256
<212> TYPE: PRT
<213> ORGANISM: Artificial Sequence
<220> FEATURE:
<223> OTHER INFORMATION: Synthetic polypeptide

<400> SEQUENCE: 119

Ala Ser Pro Asn Ser Pro Lys Asp Asn Thr Trp Ile Gln Ala Ser
1               5                   10                  15

Leu Thr Trp Leu Met Asp Met Ser Ser Leu Leu Tyr Gln Leu Ile Ser
            20                  25                  30

Thr Arg Ile Pro Ser Phe Ala Ser Pro Asn Gly Leu His Met Arg Glu
        35                  40                  45

Gln Thr Ile Asp Ser Asn Thr Gly Gln Ile Gln Ile Asp Asn Glu His
    50                  55                  60

Arg Leu Leu Arg Trp Asp Arg Arg Pro Pro Asn Asp Ile Phe Leu Asn
65                  70                  75                  80

```
Gly Phe Ile Pro Arg Val Thr Asn Gln Asn Leu Ser Pro Val Glu Asp
                85                  90                  95

Thr His Leu Leu Asn Tyr Leu Arg Thr Asn Ser Pro Ser Ile Phe Val
            100                 105                 110

Ser Thr Thr Arg Ala Arg Tyr Asn Asn Leu Gly Leu Glu Ile Thr Pro
        115                 120                 125

Trp Thr Pro His Ser Ala Asn Asn Ile Ile Tyr Arg Tyr Glu Ile
    130                 135                 140

Phe Ala Pro Gly Gly Ile Asp Ile Asn Ala Ser Phe Ser Arg Asn His
145                 150                 155                 160

Asn Pro Phe Pro Asn Glu Asp Glu Ile Thr Phe Pro Gly Gly Ile Arg
                165                 170                 175

Pro Glu Phe Ile Arg Ser Thr Tyr Glu Tyr His Asn Gly Glu Ile Val
            180                 185                 190

Arg Ile Trp Ile Asn Pro Asn Phe Ile Asn Pro Ser Thr Leu Asn Asp
        195                 200                 205

Val Ser Gly Pro Ser Asn Ile Ser Lys Val Phe Trp His Glu Asn His
    210                 215                 220

Ser Glu Gly Asn Asn Met Asp Ser Lys Gly Phe Ile Leu Asp Leu Asp
225                 230                 235                 240

Tyr Asn Gln Asp Phe Asp Met Phe Ala Pro Asn Gly Glu Ile Pro Asn
                245                 250                 255

<210> SEQ ID NO 120
<211> LENGTH: 253
<212> TYPE: PRT
<213> ORGANISM: Artificial Sequence
<220> FEATURE:
<223> OTHER INFORMATION: Synthetic polypeptide

<400> SEQUENCE: 120

Met Ala Glu Ile Thr Leu Glu Pro Ser Asp Leu Met Ala Gln Thr Asn
1               5                   10                  15

Lys Arg Ile Val Pro Lys Phe Thr Glu Ile Phe Pro Val Glu Asp Ala
            20                  25                  30

Asn Tyr Pro Tyr Ser Ala Phe Ile Ala Ser Val Arg Lys Asp Val Ile
        35                  40                  45

Lys His Cys Thr Asp His Lys Gly Ile Phe Gln Pro Val Leu Pro Pro
    50                  55                  60

Glu Lys Lys Val Pro Glu Leu Trp Phe Tyr Thr Glu Leu Lys Thr Arg
65                  70                  75                  80

Thr Ser Ser Ile Thr Leu Ala Ile Arg Met Asp Asn Leu Tyr Leu Val
                85                  90                  95

Gly Phe Arg Thr Pro Gly Gly Val Trp Trp Glu Phe Gly Lys Asp Gly
            100                 105                 110

Asp Thr His Leu Leu Gly Asp Asn Pro Arg Trp Leu Gly Phe Gly Gly
        115                 120                 125

Arg Tyr Gln Asp Leu Ile Gly Asn Lys Gly Leu Glu Thr Val Thr Met
    130                 135                 140

Gly Arg Ala Glu Met Thr Arg Ala Val Asn Asp Leu Lys Lys Lys
145                 150                 155                 160

Lys Met Ala Thr Leu Glu Glu Glu Glu Val Lys Met Gln Met Gln Met
                165                 170                 175

Pro Glu Ala Ala Asp Leu Ala Ala Ala Ala Ala Asp Pro Gln Ala
            180                 185                 190
```

Asp Thr Lys Ser Lys Leu Val Lys Leu Val Val Met Val Cys Glu Gly
            195                 200                 205

Leu Arg Phe Asn Thr Val Ser Arg Thr Val Asp Ala Gly Phe Asn Ser
        210                 215                 220

Gln His Gly Val Thr Leu Thr Val Thr Gln Gly Lys Gln Val Gln Lys
225                 230                 235                 240

Trp Asp Arg Ile Ser Lys Ala Ala Phe Glu Trp Ala Asp
                245                 250

<210> SEQ ID NO 121
<211> LENGTH: 22
<212> TYPE: PRT
<213> ORGANISM: Artificial Sequence
<220> FEATURE:
<223> OTHER INFORMATION: Synthetic polypeptide

<400> SEQUENCE: 121

Phe Ile Leu Asp Leu Asp Tyr Asn Gln Asp Phe Asp Met Phe Ala Pro
1               5                   10                  15

Asn Gly Glu Ile Pro Asn
            20

<210> SEQ ID NO 122
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 122

Cys Thr Leu Asn Phe Pro Ile Ser Pro Ile
1               5                   10

<210> SEQ ID NO 123
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 123

Gly Ala Glu Thr Phe Tyr Val Asp Gly Ala
1               5                   10

<210> SEQ ID NO 124
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 124

Pro Lys Lys Lys Arg Lys Val
1               5

<210> SEQ ID NO 125
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 125

Lys Arg Pro Ala Ala Thr Lys Lys Ala Gly Gln Ala Lys Lys Lys Lys

<210> SEQ ID NO 126
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 126

Pro Ala Ala Thr Lys Lys Ala Gly Gln Ala
1               5                   10

<210> SEQ ID NO 127
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 127

Lys Arg Lys Lys Lys Lys
1               5

<210> SEQ ID NO 128
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 128

Lys Ile Pro Ile Lys
1               5

<210> SEQ ID NO 129
<211> LENGTH: 69
<212> TYPE: DNA
<213> ORGANISM: Artificial Sequence
<220> FEATURE:
<223> OTHER INFORMATION: Primer

<400> SEQUENCE: 129
gtcggattcc tcggactcct caccaccggt gtcgaacaga ccaaaaccca tgtcatcatc      60
ggattcttc                                                             69

<210> SEQ ID NO 130
<211> LENGTH: 69
<212> TYPE: DNA
<213> ORGANISM: Artificial Sequence
<220> FEATURE:
<223> OTHER INFORMATION: Primer

<400> SEQUENCE: 130
gtgatgctgc agagaaccgg tgtcaaacag gccgaagccc atatcgtcgt cggattcctc      60
ggactcctc                                                             69

ACTIVATABLE TOXIN COMPLEXES COMPRISING A CLEAVABLE INHIBITORY PEPTIDE

RELATED APPL ing of two polypeptide chains, corresponding to segments of an N-glycosidase domain, held together by non-covalent interactions which are synthesized from a single precursor that undergoes post-translational processing.

Ricin toxin (RT) from *Ricinus communis* is a type II RIP consisting of the catalytic A chain covalently linked to the lectin domain B chain, the latter of which binds to galactose residues on the surface of eukaryotic cells and stimulates receptor-mediated endocytosis of the toxin molecule (Stirpe and Battelli, 2006). Cell-bound ricin is taken up by endocytosis, following which most of the toxin molecules are recycled back to the cell surface or transported to the lysosomes and degraded. A small fraction is translocated by retrograde transport to the trans-Golgi network, backward through the Golgi apparatus to the endoplasmic reticulum and from there to the cytosol (Olsnes, 2004).

Maize RIP is a Type III RIP produced as an inactive precursor proenzyme (pro-RIP) having a 25-amino acid internal inactivation region on the protein surface. During germination, proteolytic removal of this internal inactivation region generates the active heterodimeric maize RIP (Walsh et al., 1991; Bass et al., 1992). HIV-activated toxins designed on the basis of maize RIP have been disclosed (Law et al., 2010). According to this disclosure, replacement of the first and last 10 residues of the internal inactivation region with two HIV-PR recognition sequences, and fusion of an 11 amino acid transduction peptide derived from the HIV-1 Tat protein to the N-termini of the modified RIPs resulted in the generation of pro-RIPs which were efficiently cleaved in-vitro by recombinant HIV-PR or in-vivo (in HIV infected cells) by virally encoded protease. Upon treatment of infected cells, the N-glycosidase and anti-viral activities of the modified cleavable RIPs were found to be higher than these of an uncleavable-nonactivated pro-RIP and resembled these of an activated mutant in which the inhibitory region was genetically removed.

The mammalian defensins are a family of small cationic peptides characterized by their β-sheet-dominant structure stabilized by two or three intramolecular disulfide bonds (Ganz, (2003) Nat. Rev. Immunol. 3, 710-720). They are further subdivided into three subfamilies: α-defensins; β-defensins; and θ-defensins. Six human α-defensin peptides (each composed of 29-35 amino acid residues) have been identified from five genes, namely HNP (human neutrophil peptide)-1 to -4, HD-5, and HD-6 (Ericksen et al., Antimicrob Agents Chemother. 2005; 49:269-75). HNP-1-4 are expressed primarily by granulocytes and certain lymphocyte populations (Ganz et al., (1985) J. Clin. Invest. 76, 1427-1435; Agerberth et al., (2000) Blood 96, 3086-3093). The amino acid sequences of HNP-1-3 are identical except for the first N-terminal residue. The α-defensins have been identified as natural peptide antibiotics which display microbicidal activity against numerous bacteria, fungi, and viruses (Lehrer et al., (1993) Annu. Rev. Immunol. 11, 105-128).

HNP-1, HNP-2 and HNP-3 have been disclosed to have neutralizing activity against lethal factor (LF), the major toxin of *B. anthracis* (Kim et al., Proc Natl Acad Sci USA. 2005 Mar. 29; 102(13)). HNP-1, HNP-2 and HNP-3 have further been disclosed to neutralize toxins of the mono-ADP-ribosyltransferase family, particularly diphtheria toxin and *Pseudomonas* exotoxin A (Kim et al Biochem J (2006) 399, 225-229). HNP-1, HNP-3, and enteric human defensin-5 (HD-5) have been disclosed to inhibit the activity of *Clostridium difficile* toxin B.

The conserved C-terminus of the ribosome stalk proteins P1 and P2 has been disclosed to interact with both ricin and Shiga-like toxin 1. This interaction is reportedly required for efficient ribosome binding and cytotoxicity. In addition, a synthetic peptide corresponding to the sequence of the conserved C terminus of P1 and P2 was shown to inhibit the ribosome-inactivating function of SLT-1 (Vater et al., 1995; Chiou et al., 2008; McCluskey et al., 2008). The crystal structure of a similar peptide in complex with the type I RTP trichosanthin has been disclosed (Too et al., 2009).

Hepatitis C virus (HCV) is a small, enveloped RNA virus belonging to the *Hepacivirus* genus of the Flaviviridae family, which is recognized as a major cause of chronic liver disease and affects approximately 200 million people worldwide. Persistent infection is associated with the development of chronic hepatitis, hepatic steatosis, cirrhosis, and hepatocellular carcinoma. A protective vaccine for HCV is not yet available, and the currently favored treatment, which is a combination of pegylated α-interferon and ribavirin, fails to eliminate infection in nearly 50% of infected subjects.

The HCV genome encodes one large open reading frame that is translated as a polyprotein and proteolytically processed to yield the viral structural and non-structural (NS) proteins. The envelope glycoproteins E1 and E2 and the core protein are the structural proteins, which together form the viral particle. The non-structural proteins include the p7 ion channel, the NS2-3 protease, the NS3 serine protease/RNA helicase and its co-factor NS4A, the NS4B and NS5A proteins and the NS5B RNA-dependent RNA polymerase (RdRp) (Moradpour et al., 2007; Suzuki et al., 2007). HCV polyprotein processing involves the NS2-3 autoprotease, which cleaves in cis at the NS2-3 junction, and the NS3-4A serine protease, which cleaves at four downstream NS protein junctions, respectively termed NS3/4A; NS4A/4B; NS/4B/5A, AND NS5A/5B. NS3 has been extensively studied and shown to possess multiple enzymatic activities that are essential for HCV replication. The N-terminus, in complex with its co-factor NS4A, primarily functions as a serine protease, which cleaves the viral polyprotein precursor downstream to NS3. The remaining $2/3$ of the protein has helicase and NTPase activities (Bartenschlager, 1999).

WO 2006/109196 discloses a method to identify a compound that inhibits HCV replication comprising: contacting a genetically modified mouse with a compound and analyzing the expression of NS3 protease activity, whereby a compound that inhibits expression of NS3 is indicative that said compound inhibits HCV replication.

WO 2009/022236 discloses compositions that comprise an isolated nucleic acid encoding a chimeric hepatitis C virus NS3/4A polypeptide or a fragment thereof, which comprises a sequence that encodes an antigen, preferably a non-HCV epitope, wherein the nucleic acid encoding the antigen can be inserted within the NS3/4A nucleic acid or attached thereto. Further disclosed is a composition comprising a recombinant peptide immunogen comprising an antigen, such as an antigen comprising an epitope from a plant, virus, bacteria, or a cancer cell; and a heterologous HCV NS3 protease cleavage site. According to the disclosure, NS3/4A is used as a carrier or adjuvant to provide T helper cells access to a fused antigen, thereby enhancing the immune response to the fused antigen, and the antigen may be inter alia a toxin.

WO 2008/052490 discloses a chimeric peptide containing at least one segment which inhibits the activation of the NS3 protease of a Flaviviridae family virus, and a cell penetrating segment which can inhibit or attenuate infection by the virus. Further disclosed are pharmaceutical compounds containing the chimeric peptides and use thereof for prevention and/or treatment of Flaviviridae virus infections.

WO 2004/005473 discloses an immunogenic fusion protein comprising (a) a modified NS3 polypeptide comprising at least one amino acid substitution to the HCV NS3 region, such that protease activity is inhibited, and (b) at least one polypeptide derived from a region of the HCV polyprotein other than the NS3 region. According to the disclosure, compositions of the invention may include a carrier or an adjuvant inter alia a detoxified mutant of a bacterial ADP-ribosylating toxin such as a cholera toxin.

WO 2003/064453 discloses active inhibitors, termed "trojan inhibitors" (TI) and the use thereof in the form of specifically shaped trojan proteasome-inhibitors (TPI) or trojan assembling-inhibitors (TAI), such as proteasome- and assembling-inhibitors which are initially inactive and are only activated in the target cell by means of a specific protease for the target cell. According to the disclosure, said inhibitor can be used in the treatment of viral infections, whereby a virus-specific protease is expressed, particularly in HIV-infections and AIDS-therapy, and in the therapy of tumoral diseases, whereby the tumor cells are characterized by a specific protease.

WO 2002/087500 discloses a synthetic prototoxophore, which is a relatively non-toxic compound that includes a toxin moiety, such as an antimetabolite or a DNA intercalating agent, and a substrate domain for a viral enzyme, which upon binding of a viral enzyme to the substrate domain, the catalytic activity of the viral enzyme converts the prototoxophore to a toxophore, which is toxic to a cell. Further disclosed are methods of using a prototoxophore to reduce or inhibit viral infectivity, and to ameliorate the severity of a viral infection.

WO 2005/090393 discloses a composition comprising a first effector component of a multimeric bacterial protein toxin, the first effector component comprising at least a first monomer and a second monomer, wherein said first and second monomers form a heterooligomer, wherein said first and second monomers are different, and each of said first and second monomers are modified by at least two of the following methods: (a) substitution of a native cell-recognition domain for a non-native cell-recognition domain; (b) substitution of a native proteolytic activation site for a non-native proteolytic activation site; (c) modification of said first monomer to generate a first modified monomer, whereby said first modified monomer can pair only with said second monomer; (d) modification of said first monomer and said second monomer, whereby a second effector component can bind only at a site formed by the interaction of said first monomer and said second monomer molecule; or (e) a combination thereof.

According to the disclosure, the bacterial protein toxin may be inter alia cholera toxin or Shiga toxin; (b) may comprise substitution of a native furin cleavage site by a serine protease cleavage site; and the composition may be used for treating a viral infection inter alia HCV.

WO 2000/062067 discloses a fusion molecule comprising at least one protein transduction domain (PTD) and at least one linked molecule, inter alia an anti-infective drug.

WO 1999/029721 discloses an anti-pathogen system comprising a fusion protein comprising a covalently linked protein transduction domain and a cytotoxic domain (i.e. a caspase), wherein the cytotoxic domain further comprises at least one pathogen-specific protease cleavage site, wherein the pathogen may be inter alia HCV.

U.S. Pat. No. 7,247,715 discloses a purified and isolated nucleic acid sequence having a nucleotide sequence encoding an A chain of a ricin-like toxin, a B chain of a ricin-like toxin and a heterologous linker amino acid sequence linking the A and B chains, the heterologous linker sequence containing a cleavage recognition site for a protease, inter alia a viral protease, wherein the cleavage recognition site is recognized by the viral protease inter alia hepatitis C virus.

There remains an unmet need for therapeutic agents which are effective for the treatment of debilitating diseases, including viral infections such as HCV.

SUMMARY OF THE INVENTION

The inventors of the present invention disclose herein a therapeutic approach for eradicating diseased cells, including cells infected by intracellular pathogens such as viruses, as well as cancerous cells. The invention provides multi-segment fusion proteins, which include a highly toxic catalytic domain based on a naturally occurring toxin, such as that of a plant or bacterial species, and a cleavable inhibitory peptide which "disarms" the activity of the catalytic domain until the inhibitory peptide is released, preferably at the infection or disease site. The inhibitory peptide is rendered cleavable due to the presence of a protease cleavage recognition site within the fusion protein, with the cleavage site being the target of a protease specifically expressed in the diseased cells. When the fusion protein comes into contact with the protease, such as a virus-encoded protease, enzymatic release of the inhibitory peptide occurs and "arms" the fusion protein into the active toxic state.

Specifically, the multi-segment fusion protein comprises the following segments from the amino terminus to the carboxy terminus in the following order: a cell binding domain; a cell translocation domain; a toxin catalytic domain; a protease enzyme cleavage recognition site; an inhibitory peptide; and at least one linker, wherein the at least one linker is located between the protease enzyme cleavage recognition site and the inhibitory peptide.

The invention is based, in part, on the finding that hepatitis C virus (HCV) NS3 protease-activated chimeric toxins comprising cell binding and translocation domains from *Pseudomonas* exotoxin A, and a catalytic toxin domain of either diphtheria toxin or ricin A in fusion with a cleavable inhibitor peptide, exhibit a significant increase in enzymatic activity following NS3-mediated cleavage, and exhibit high levels of cytotoxicity, both in NS3-transfected cells and in HCV-infected cells. The fusion proteins disclosed herein comprise toxin enzymatic domains which have been "zymogenized", and thus are also referred to herein as "zymogenized toxins" or "zymoxins".

Without being bound by any theory or mechanism of action, the efficacy of the invention disclosed herein is due to the selective activation of the fusion protein in vivo. Since the inhibitory peptide may only be released within infected cells which express the virally encoded protease, the invention disclosed herein is effective for selective killing of infected cells, and for blocking multiplication and spread of the infectious organism.

The present invention is particularly advantageous for eradicating intracellular viral infections which do not involve display of viral antigens on the outer surface of infected cells, and are thus not amenable to treatment with agents which include targeting and binding moieties, such as antibodies, directed to cell surface-displayed viral antigens. Such infections, including those caused by hepatitis B and hepatitis C viruses, are generally characterized by the arrangement of viral proteins on internal cell membranes and budding of viral particles from cells, in the absence of any trace of viral infection on the outer cell membrane.

However, the invention may also be used to provide agents for treating viral infections which do involve display of viral antigens on the outer surface of infected cells, such as HIV infection.

BRIEF DESCRIPTION OF THE DRAWINGS

FIG. 1 shows tetracycline induced expression of active EGFP-scNS3 and EGFP-full NS3-4A in T-Rex 293 cells.

DETAILED DESCRIPTION OF THE INVENTION

Figures 1A, 1B, 1C:
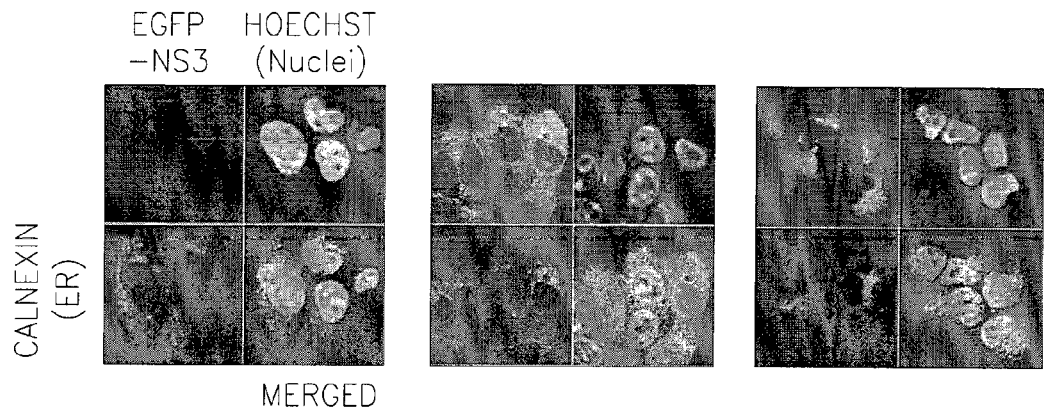
FIGS. 1A-C (upper panel) shows immunofluorescence analysis of inducible NS3 expressing cells. $10^5$ cells induced to express EGFP-scNS3 or EGFP-full NS3-4A were seeded on cover-slips in a 24 well plate. After 12 hours, the cells were treated with 1 µg/ml of tetracycline for 24 hours and then were fixed and permeabilized. Following immunostaining with rabbit anti-calnexin and Cy3-conjugated goat-anti rabbit antibody for ER visualization (indicated in red) and nuclei staining by Hoechst 33258 (indicated in blue), slides were examined by confocal fluorescence microscopy. (A), non-induced cells; (B), induced scNS3 expressing cells; (C), induced full NS3-4A expressing cells.

The present invention provides toxin fusion proteins and conjugate proteins which are selective and activatable in vivo due to the presence of a cleavable inhibitory peptide which prevents toxic effects until cleaved by a protease. The inhibitory peptide included in the protein is selected and positioned so as to specifically inhibit the activity of the catalytic toxic domain and not the other functional domains. The protein is further engineered so as to contain a protease enzyme cleavage recognition site, which is the substrate of a specific protease expressed in diseased cells, such as the NS3 protease expressed in HCV infected cells. Upon contact with the relevant protease at the disease site, such as within virus-infected cells, the protein is acted upon by the protease so as to release the inhibitory peptide, thus activating the protein into its active toxic state.

In a first aspect, the invention provides a multi-domain toxin protein conjugate, the conjugate comprising: a cell binding domain; a cell translocation domain; a toxin catalytic domain; a protease enzyme cleavage recognition site; an inhibitory peptide (protease inhibitory peptide); and at least one linker, wherein the at least one linker is located between the protease enzyme cleavage recognition site and the inhibitory peptide.

In another aspect, the invention provides a toxin fusion protein, the fusion protein comprising: a first segment comprising a cell binding domain; a second segment comprising a cell translocation domain; a third segment comprising a toxin catalytic domain; a fourth segment comprising a protease enzyme cleavage recognition site; a fifth segment comprising an inhibitory peptide; and at least one linker, wherein the at least one linker is located between the fourth segment comprising the protease enzyme cleavage recognition site and the fifth segment comprising the inhibitory peptide. In a particular embodiment, the protein conjugate comprises a fusion protein. In a particular embodiment, the protein conjugate comprises covalent linkages between the domains. In a particular embodiment, the protein conjugate comprises non-covalent linkages between the domains. In a particular embodiment, the protein conjugate comprises a combination of covalent and non-covalent linkages between or among the domains.

In a particular embodiment, the cell binding domain comprises at least one of: a cell binding domain of a bacterial, plant or fungal toxin; a cell-penetrating peptide (CPP); an antibody; a cell surface receptor ligand, or a combination thereof. Each possibility corresponds to a separate embodiment of the invention.

In a particular embodiment, the cell binding domain comprises a cell binding domain of a bacterial or plant toxin. In a particular embodiment, the toxin is selected from the group consisting of *Pseudomonas* exotoxin, diphtheria toxin, cholera toxin; tetanus toxin, botulinum toxin, *Clostridium difficile* toxin, anthrax toxin, verotoxin, pertussis toxin, ricin, abrin, Shiga-like toxin 1 (SLT-1), modecin, volkensin, visumin, trichosanthin, maize RIP, luffaculin 1, and alpha-luffin. Each possibility corresponds to a separate embodiment of the invention.

In a particular embodiment, the cell binding domain comprises a cell binding domain from a toxin selected from the group consisting of *Pseudomonas* exotoxin and diphtheria toxin. Each possibility corresponds to a separate embodiment of the invention.

In a particular embodiment, the cell binding domain comprises a cell-penetrating peptide. In a particular embodiment, the cell-penetrating peptide is selected from the group consisting of a polyarginine, such as RRRRRRRRR (SEQ ID NO:74); TAT$_{49-57}$ (RKKRRQRRR; SEQ ID NO:75); TAT (GRKKRRQRRRPPQ; SEQ ID NO:76), Pep-1 (KETWWETWWTEWSQPKKKRKV; SEQ ID NO:77) Antennapedia cell-penetrating peptide (RQIKIWFQNRRMKWKK; SEQ ID NO:78), transportan (GWTLNSAGYLLGKINLKALAALAKKIL; SEQ ID NO:79) and a nuclear localization sequence (NLS), such as VQRKRQKLMP (SEQ ID NO:80), SKKKKIKV (SEQ ID NO:81) or GRKRKKRT (SEQ ID NO:82).

In a particular embodiment, the cell binding domain comprises an antibody specific for an antigen expressed on the surface of a diseased cell. In a particular embodiment, the cell binding domain comprises an antibody specific for an antigen encoded by an intracellular pathogen. In a particular embodiment, the diseased cell is selected from the group consisting of a pathogen-infected cell and a cancerous cell. In a particular embodiment, the pathogen is selected from the group consisting of a virus, a bacteria and a fungus. In a particular embodiment, the diseased cell is selected from the group consisting of a virus-infected cell, a bacteria-infected cell and a fungus-infected cell.

In a particular embodiment, the pathogen is a virus. In a particular embodiment, the virus is selected from the group consisting of a retrovirus, a paramyxovirus, a orthomyxovirus, an arenavirus, a filovirus, a coronavirus and a rhabdovirus. In a particular embodiment, the virus is selected from a human immunodeficiency virus (HIV), such as HIV-1; a hepatitis virus, such as HBV or HCV; a herpes simplex virus, such as HSV-1 or HSV-2; an influenza virus such as influenza A virus, influenza B virus or influenza C virus; cytomegalovirus (CMV); respiratory syncytial virus (RSV); measles virus; polio virus and smallpox virus. Each possibility corresponds to a separate embodiment of the invention.

In a particular embodiment, the virus is HCV.

In a particular embodiment, the cell binding domain comprises an antibody such as a monoclonal antibody or an antigen-binding fragment thereof. In a particular embodiment, the fragment is selected from the group consisting of Fab, F(ab)$_2$, scFv, dsFv, sc-dsFv and Fv.

In a particular embodiment, the antigen expressed on the surface of a diseased cell is a viral antigen. In a particular embodiment, the viral antigen is selected from the group consisting of HIV gp120 and HIV gp41.

In a particular embodiment, the antigen encoded by a pathogen is a virus-encoded antigen. In a particular embodiment, the virus-encoded antigen is selected from the group consisting of HCV NS3; HCV NS4B; HCV NS5A; HCV NS5B; HBV core protein (HBcAg); HIV gp120 and HIV gp41. [OK—WE ARE PROVIDING POSSIBILITIES FOR THE CASES OF "antigen expressed on the surface of a diseased cell" AND "antigen encoded by an intracellular pathogen" SPECIFIED ABOVE.

In a particular embodiment, the antigen is a tumor-specific antigen.

In a particular embodiment, the cell binding domain specifically binds the asialoglycoprotein receptor. In a particular embodiment, the cell binding domain comprises carbohydrate residues.

In a particular embodiment, the cell translocation domain comprises a cell translocation domain of a plant, bacterial or fungal toxin. In a particular embodiment, the cell translocation domain comprises a cell translocation domain of a toxin selected from the group consisting of *Pseudomonas* exotoxin diphtheria toxin, anthrax toxin, botulinum toxin and *Clostridium difficile* toxin. In a particular embodiment, the cell translocation domain comprises the cell translocation of *Pseudomonas* exotoxin or diphtheria toxin. Each possibility corresponds to a separate embodiment of the invention.

In a particular embodiment, the cell translocation domain comprises a cell-penetrating peptide. In a particular embodiment, the cell-penetrating peptide is selected from the group consisting of a polyarginine, such as RRRRRRRRR (SEQ ID NO:74); TAT$_{49-57}$ (RKKRRQRRR; SEQ ID NO:75); TAT (GRKKRRQRRRPPQ; SEQ ID NO:76), Pep-1 (KETWWETWWTEWSQPKKKRKV; SEQ ID NO:77) Antennapedia cell-penetrating peptide (RQIKIWFQNRRMKWKK; SEQ ID NO:78), transportan (GWTLNSAGYLLGKINLKALAALAKKIL; SEQ ID NO:79) and a nuclear localization sequence (NLS), such as VQRKRQKLMP (SEQ ID NO:80), SKKKKIKV (SEQ ID NO:81) or GRKRKKRT (SEQ ID NO:82).

In a particular embodiment, the cell translocation domain comprises a transduction domain of a viral protein. In a particular embodiment, the cell translocation domain comprises an HIV TAT protein transduction domain.

In a particular embodiment, the cell binding domain and the cell translocation domain are derived from *Pseudomonas* exotoxin. In a particular embodiment, the cell binding domain and the cell translocation domain comprise a single domain. In a particular embodiment, the cell binding domain and the cell translocation domain are derived from heterologous toxins. In a particular embodiment, the cell binding domain and the cell translocation domain are derived from a single toxin.

In a particular embodiment, the toxin catalytic domain comprises a catalytic domain from a plant, bacterial or fungal toxin. In a particular embodiment, the toxin catalytic domain is from a toxin selected from the group consisting of *Pseudomonas* exotoxin, diphtheria toxin, tetanus toxin, botulinum toxin, *Clostridium difficile* toxin, anthrax toxin, verotoxin, pertussis toxin, ricin, abrin, Shiga-like toxin 1 (SLT-1), modecin, volkensin, visumin, trichosanthin, maize RIP, mosquitocidal toxin from *Bacillus sphaericus* SSII-1 (MTX); luffaculin 1, and alpha-luffin. Each possibility corresponds to a separate embodiment of the invention.

In a particular embodiment, the toxin catalytic domain is derived from a toxin selected from the group consisting of diphtheria toxin, ricin and *Pseudomonas* exotoxin. Each possibility corresponds to a separate embodiment of the invention. In a particular embodiment, the cell binding domain and the toxin catalytic domain are from heterologous toxins.

In a particular embodiment, the cell binding domain and the cell translocation domain are both derived from *Pseudomonas* exotoxin, and the toxin catalytic domain is from diphtheria toxin or ricin. Each possibility corresponds to a separate embodiment of the invention.

In a particular embodiment, the protease enzyme cleavage recognition site comprises a cleavage recognition site of a protease enzyme specifically expressed in a diseased cell but not in a healthy cell. In a particular embodiment, a diseased cell expressed a protease unique to the disease. In a particular embodiment, proteases within a healthy cell do not cleave the protease enzyme cleavage recognition site. In a particular embodiment, the diseased cell is a pathogen-infected cell or a cancerous cell. In a particular embodiment, the pathogen encodes the protease enzyme. Particular embodiments of the pathogen are as hereinbefore described. In a particular embodiment, the protease enzyme cleavage recognition site is a substrate of a viral protease enzyme. In a particular embodiment, the viral protease enzyme is selected from the group consisting of HCV NS3 protease; HIV protease; CMV protease; and HSV protease. In a particular embodiment, the protease enzyme cleavage recognition site comprises an HCV NS3 target site. In a particular embodiment, the HCV NS3 target site is at an NS protein junction selected from the group consisting of NS3/4A; NS4A/4B; NS4B/5A and NS5A/5B.

In a particular embodiment, the protease enzyme cleavage recognition site comprises an amino acid sequence selected from the group consisting of SEQ ID NOs:1-18. Each possibility corresponds to a separate embodiment of the invention.

In a particular embodiment, the protease enzyme cleavage recognition site comprises SEQ ID NO:1.

In a particular embodiment, the protease enzyme cleavage recognition site comprises an amino acid sequence selected from the group consisting of SEQ ID NOs:19-38. Each possibility corresponds to a separate embodiment of the invention.

In a particular embodiment, the protease enzyme cleavage recognition site comprises SEQ ID NO:19.

| SEQ ID NO: | Amino acid sequence | Junction |
|---|---|---|
| 1 | EDVVCCSMSY | NS5A/5B |
| 2 | DSVVCCSMSY | NS5A/5B |
| 3 | EGVICCSMSY | NS5A/5B |
| 4 | DSVICCSMSY | NS5A/5B |
| 5 | DDVICCSMSY | NS5A/5B |
| 6 | QSVVCCSMSY | NS5A/5B |
| 7 | DLEVVTSTWV | NS3/4A |
| 8 | DLEVMTSTWV | NS3/4A |
| 9 | DLEIMTSTWV | NS3/4A |
| 10 | QLEVVTSTWV | NS3/4A |
| 11 | DEMEECSQHL | NS4A/4B |
| 12 | DEMEECASHL | NS4A/4B |
| 13 | DEMEECASRA | NS4A/4B |
| 14 | DEMEECASKA | NS4A/4B |
| 15 | ECTTPCSGSW | NS4B/5A |

| SEQ ID NO: | Amino acid sequence | cleavage recognition site of |
|---|---|---|
| 16 | DCSTPCSGSW | NS4B/5A |
| 17 | DCPIPCSGSW | NS4B/5A |
| 18 | DCPVPCSGSW | NS4B/5A |
| 19 | SEEDDTTVCCSMSYSWTGAL | NS5A/5B) |
| 20 | EEASEDVVCCSMSYTWTGAL | NS5A/5B |
| 21 | SEEDDSVVCCSMSYSWTGAL | NS5A/5B |
| 22 | EEDGEGVICCSMSYTWTGAL | NS5A/5B |
| 23 | SDQEDSVICCSMSYSWTGAL | NS5A/5B |
| 24 | GEASDDVICCSMSYTWTGAL | NS5A/5B |
| 25 | DSEEQSVVCCSMSYSWTGAL | NS5A/5B |
| 26 | GADTEDVVCCSMSYSWTGAL | NS5A/5B |
| 27 | CMSADLEVVTSTWVLVGGVL | NS3/4A |
| 28 | CMQADLEVMTSTWVLAGGVL | NS3/4A |
| 29 | CMQADLEIMTSTWVLAGGVL | NS3/4A |
| 30 | CMSAQLEVVTSTWVLVGGVL | NS3/4A |
| 31 | YQEFDEMEECSQHLPYIEQG | NS4A/4B |
| 32 | YQEFDEMEECASHLPYIEQG | NS4A/4B |
| 33 | YEAFDEMEECASRAALIEEG | NS4A/4B |
| 34 | YQAFDEMEECASKAALIEEG | NS4A/4B |
| 35 | WISSECTTPCSGSWLRDIWD | NS4B/5A |
| 36 | WINEDCSTPCSGSWLRDVWD | NS4B/5A |
| 37 | WITEDCPIPCSGSWLRDVWD | NS4B/5A |
| 38 | WITEDCPVPCSGSWLQDIWD | NS4B/5A |

| SEQ ID NO: | Amino acid sequence | cleavage recognition site of |
|---|---|---|
| 39 | SGVVNASCRLAN | CMV protease enzyme |
| 40 | SSYVKASVSPEN | CMV protease enzyme |
| 41 | SALVNASSAHVN | HSV-1 protease enzyme |
| 42 | STYLQASEKFKN | HSV-1 protease enzyme |
| 43 | VSQNYPIVQN | HIV protease enzyme |
| 44 | KARVLAEAMS | HIV protease enzyme |
| 45 | STAIMMQKGN | HIV protease enzyme |
| 46 | TSAIMMQRGN | HIV protease enzyme |
| 47 | ERQANFLGKI | HIV protease enzyme |
| 48 | RPGNFLQSRP | HIV protease enzyme |
| 49 | ERQANFLREN | HIV protease enzyme |
| 50 | ENLAFQQGEA | HIV protease enzyme |
| 51 | EDLAFLQFKA | HIV protease enzyme |
| 52 | TSFSFPQITC | HIV protease enzyme |
| 53 | VSFNFPQVTC | HIV protease enzyme |
| 54 | CTLNFPISPIGAETFYVDGA | HIV protease enzyme |
| 55 | IRKVLFLDGI | HIV protease enzyme |
| 56 | PDCAWLEAQE | HIV protease enzyme |
| 122 | CTLNFPISPI | HIV protease enzyme |
| 123 | GAETFYVDGA | HIV protease enzyme |

In other embodiments, the protease enzyme cleavage recognition site comprises a CMV protease enzyme cleavage recognition site selected from SEQ ID NO:39 and SEQ ID NO:40. In other embodiments, the protease enzyme cleavage recognition site comprises an HSV-1 protease enzyme cleavage recognition site selected from SEQ ID NO:41 and SEQ ID NO:42.

In other embodiments, the protease enzyme cleavage recognition site comprises an HIV protease enzyme cleavage recognition site selected from SEQ ID NO:43; SEQ ID NO:44; SEQ ID NO:45; SEQ ID NO:46; SEQ ID NO:47; SEQ ID NO:48; SEQ ID NO:49; SEQ ID NO:50; SEQ ID NO:51; SEQ ID NO:52; SEQ ID NO:53; SEQ ID NO:54; SEQ ID NO:55; and SEQ ID NO:56. Each possibility corresponds to a separate embodiment of the invention.

In a particular embodiment, the inhibitory peptide specifically inhibits a catalytic domain that has ADP-ribosyl transferase activity. In a particular embodiment, the inhibitory peptide specifically inhibits a catalytic domain that has N-glycosidase activity. In a particular embodiment, the inhibitory peptide comprises an autoinhibiting fragment of a toxin that has ADP-ribosyl transferase activity. In a particular embodiment, the inhibitory peptide comprises an autoinhibiting fragment of a toxin that has N-glycosidase activity.

In a particular embodiment, the inhibitory peptide comprises a defensin peptide or a fragment thereof. In a particular embodiment, the inhibitory peptide comprises a ribosomal protein or a fragment thereof. In a particular embodiment, the inhibitory peptide is a fragment of a human defensin peptide or a fragment of a ribosomal stalk protein. Each possibility corresponds to a separate embodiment of the invention.

In a particular embodiment, the human defensin peptide is a human alpha defensin peptide selected from the group consisting of HNP-1; HNP-2; HNP-3; HNP-4; HD-5 and HD-6. Each possibility corresponds to a separate embodiment of the invention.

In a particular embodiment, the human defensin peptide is human HNP-1.

In a particular embodiment, the inhibitory peptide is a fragment of a ribosomal stalk protein selected from the group consisting of ribosomal stalk protein P1 and ribosomal stalk protein P2.

In a particular embodiment, the inhibitory peptide comprises an autoinhibiting fragment of a toxin selected from the group consisting mosquitocidal toxin (MTX; SEQ ID NO:119) from *Bacillus sphaericus* SSII-1 and maize RIP (SEQ ID NO:120). In a particular embodiment, the inhibitory peptide comprises FILDLDYNQDFDMFAPNGEIPN (SEQ ID NO:121).

| SEQ ID NO | DESCRIPTION | AMINO ACID SEQUENCE |
|---|---|---|
| 119 | mosquitocidal toxin from *Bacillus sphaericus* SSII-1 | ASPNSPKDNTWIQAASLTWLMDMSSLLYQLISTRIPSFASPNGL HMREQTIDSNTGQIQIDNEHRLLRWDRRPPNDIFLNGFIPRVTN QNLSPVEDTHLLNYLRTNSPSIFVSTTRARYNNLGLEITPWTPH SANNNIIYRYEIFAPGGIDINASFSRNHNPFPNEDEITFPGGIRPEF IRSTYEYHNGEIVRIWINPNFINPSTLNDVSGPSNISKVFWHENH SEGNNMDSKG FILDLDYNQDFDMFAPNGEIPN |
| 120 | maize RIP | MAEITLEPSDLMAQTNKRIVPKFTEIFPVEDANYPYSAFIASVRKD VIKH CTDHKGIFQPVLPPEKKVPELWFYTELKTRTSSITLAIRMD NLYLVGFRTPGGVWWEFGKDGDTHLLGDNPRWLGFGGRYQD LIGNKGLETVTMGRAEMTRAVNDLAKKKKMATLEEEEVKMQM QMPEAADLAAAAAADPQADTKSKLVKLVVMVCEGLRFNTVSRT VDAGFNSQHGVTLTVTQGKQVQKWDRISKAAFEWAD |

In a particular embodiment, the inhibitory peptide comprises a peptide selected from the group consisting of SEQ ID NO:57 (ACYCRIPACIAGERRYGTCIYQGRLWAFCC) and EESEESDDDMGFGLFD (SEQ ID NO:58). In a particular embodiment, the inhibitory peptide is selected from the group consisting of SEQ ID NO:57, SEQ ID NO:58 and SEQ ID NO:59 (EESEESDDDMGFGLFDTGGEESEESDDDMGFGLFD).

In a particular embodiment, the inhibitory peptide comprises a human alpha defensin peptide or a fragment thereof, and the catalytic domain comprises a catalytic domain from a toxin that has ADP-ribosyl transferase activity. In a particular embodiment, the inhibitory peptide comprises a human alpha defensin peptide or a fragment thereof; and the catalytic domain has ADP-ribosyl transferase activity. In a particular embodiment, the inhibitory peptide comprises a fragment of a human alpha defensin peptide selected from the group consisting of HNP-1, HNP-2 and HNP-3; and the catalytic domain is from a toxin selected from the group consisting of: *Pseudomonas* exotoxin, diphtheria toxin, *Clostridium difficile* toxin and anthrax toxin. Each possibility corresponds to a separate embodiment of the invention.

In a particular embodiment, the inhibitory peptide comprises a ribosomal stalk protein or a fragment thereof and the catalytic domain is from a toxin that has N-glycosidase activity. In a particular embodiment, the inhibitory peptide comprises a ribosomal stalk protein or a fragment thereof; and the catalytic domain has N-glycosidase activity. In a particular embodiment, the inhibitory peptide comprises a fragment of a ribosomal stalk protein selected from the group consisting of ribosomal stalk protein P1 and ribosomal stalk protein P2; and the catalytic domain is from a toxin selected from the group consisting of ricin, abrin, Shiga-like toxin 1 (SLT-1), modecin, volkensin, visumin, trichosanthin, maize RIP, luffaculin 1 and alpha-luffin. Each possibility corresponds to a separate embodiment of the invention.

In one embodiment, the at least one linker comprises from about 2 to about 50 amino acid residues. In a particular embodiment, the at least one linker comprises from about 2 to about 20 amino acid residues. In a particular embodiment, the at least one linker comprises a plurality of amino acid residues selected from the group consisting of glycine, serine histidine and a combination thereof. In another embodiment, the linker is a single amino acid.

In a particular embodiment, the linker comprises an amino acid sequence selected from the group consisting of GGGGSGGGSGSGGSG (SEQ ID NO:60); GSGS (SEQ ID NO:61); SSGS (SEQ ID NO:62); and GGGGS (SEQ ID NO:63).

In a particular embodiment, the inhibitory peptide of the protein conjugate is flanked by linkers. In a particular embodiment, the inhibitory peptide flanked by linkers is C-terminal to the protease enzyme cleavage recognition site in the protein conjugate. In a particular embodiment of the protein conjugate, the inhibitory peptide is C-terminal to the catalytic domain. In a particular embodiment of the protein conjugate, the protease enzyme cleavage recognition site and the inhibitory peptide are C-terminal to the catalytic domain.

In a particular embodiment, the inhibitory peptide in the protein conjugate is N-terminal to the catalytic domain. In a particular embodiment, the inhibitory peptide is directly linked or linked via a linker to the N-terminal of the catalytic domain. In a particular embodiment, the protease enzyme cleavage recognition site and the inhibitory peptide in the protein conjugate are N-terminal to the catalytic domain. In a particular embodiment, the protease enzyme cleavage recognition site and the inhibitory peptide are linked to the N-terminal of the catalytic domain.

In a particular embodiment of the fusion protein, the fifth segment comprising the inhibitory peptide is flanked by linkers. In a particular embodiment of the fusion protein, the fifth segment flanked by linkers is C-terminal to the fourth segment comprising the protease enzyme cleavage recognition site.

In a particular embodiment of the fusion protein, the fourth and fifth segments are C-terminal to the third segment. In a particular embodiment of the fusion protein, the fourth and fifth segments are N-terminal to the third segment.

In a particular embodiment of the fusion protein, the first through fifth segments are arranged in the order of N-terminal to C-terminal. In a particular embodiment of the fusion protein, the first through fifth segments are arranged in the order of C-terminal to N-terminal.

In a particular embodiment, the fusion protein comprises an amino acid sequence selected from the group consisting of SEQ ID NO:64; SEQ ID NO:65; SEQ ID NO:66; SEQ ID NO:67; and SEQ ID NO:68.

In a particular embodiment, the fusion protein is encoded by a nucleic acid sequence selected from the group consisting of SEQ ID NO:69; SEQ ID NO:70; SEQ ID NO:71; SEQ ID NO:72; and SEQ ID NO:73 (encoding SEQ ID NOS:64-68, respectively).

| SEQ ID NO | Amino acid sequence |
|---|---|
| 64 | MKKTAIAIAVALAGFATVAQAANLAEEAFDLWNECAKACVLDLKDGVRSSRMS VDPAIADTNGQGVLHYSMVLEGGNDAL KLAIDNALSITSDGLTIRLEGGVEPNKPVRYSYTRQARGSWSLNWLVPIGHEKPS NIKVFIHELNAGNQLSHMSPIYTIE MGDELLAKLARDATFFVRAHESNEMQPTLAISHAGVSVVMAQTQPRREKRWSE WASGKVLCLLDPLDGVYNYLAQQRCNL DDTWEGKIYRVLAGNPAKHDLDIKPTVISHRLHFPEGGSLAALTAHQACHLPLET FTRHRQPRGWEQLEQCGYPVQRLVA LYLAARLSWNQVDQVIRNALASPGSGGDLGEAIREQPEQARLALTLAAAESERF VRQGTGNDEAGAANADVVSLTCPVAA GECAGPADSGDALLERNYPTGAEFLGDGGDVGTGGADDVVDSSKSFVMENFSS YHGTKPGYVDSIQKGIQKPKSGTQGNY DDDWKGFYSTDNKYDAAGYSVDNENPLSGKAGGVVKVTYPGLTKVLALKVDN AETIKKELGLSLTEPLMEQVGTEEFIKR FGDGASRVVLSLPFAEGSSSVEYINNWEQAKALSVELEINFETRGKRGQDAMYE YMAQACAEDVVCCSMSYAIGLQGGGG SGGGSGSGGSGACYCRIPACIAGERRYGTCIYQGRLWAFCCGSGSHHHHHHICDE L |
| 65 | MKKTAIAIAVALAGFATVAQAANLAEEAFDLWNECAKACVLDLKDGVRSSRMS VDPAIADTNGQGVLHYSMVLEGGNDAL KLAIDNALSITSDGLTIRLEGGVEPNKPVRYSYTRQARGSWSLNWLVPIGHEKPS NIKVFIHELNAGNQLSHMSPIYTIE MGDELLAKLARDATFFVRAHESNEMQPTLAISHAGVSVVMAQTQPRREKRWSE WASGKVLCLLDPLDGVYNYLAQQRCNL DDTWEGKIYRVLAGNPAKHDLDIKPTVISHRLHFPEGGSLAALTAHQACHLPLET FTRHRQPRGWEQLEQCGYPVQRLVA LYLAARLSWNQVDQVIRNALASPGSGGDLGEAIREQPEQARLALTLAAAESERF VRQGTGNDEAGAANADVVSLTCPVAA GECAGPADSGDALLERNYPTGAEFLGDGGDVSFSTRGIFPKQYPIINFTTAGATV QSYTNFIRAVRGRLTTGADVRHEIP VLPNRVGLPINQRFILVELSNHAELSVTLALDVTNAYVVGYRAGNSAYFFHPDN QEDAEAITHLFTDVQNRYTFAFGGNY DRLEQLAGNLRENIELGNGPLEEAISALYYYSTGGTQLPTLARSFIICIQMISEAAR FQYIEGEMRTRIRYNRRSAPDPS VITLENSWGRLSTAIQESNQGAFASPIQLQRRNGSKFSVYDVSILIPIIALMVYRCA PPPSSGSEDVVCCSMSYGGGGSE ESEESDDDMGFGLFDTGGEESEESDDDMGFGLFDTGSLQHHHHHHKDEL |
| 66 | MKKTAIAIAVALAGFATVAQAANLAEEAFDLWNECAKACVLDLKDGVRSSRMS VDPAIADTNGQGVLHYSMVLEGGNDAL KLAIDNALSITSDGLTIRLEGGVEPNKPVRYSYTRQARGSWSLNWLVPIGHEKPS NIKVFIHELNAGNQLSHMSPIYTIE MGDELLAKLARDATFFVRAHESNEMQPTLAISHAGVSVVMAQTQPRREKRWSE WASGKVLCLLDPLDGVYNYLAQQRCNL DDTWEGKIYRVLAGNPAKHDLDIKPTVISHRLHFPEGGSLAALTAHQACHLPLET FTRHRQPRGWEQLEQCGYPVQRLVA LYLAARLSWNQVDQVIRNALASPGSGGDLGEAIREQPEQARLALTLAAAESERF VRQGTGNDEAGAANADVVSLTCPVAA GECAGPADSGDALLERNYPTGAEFLGDGGDVGTGGADDVVDSSKSFVMENFSS YHGTKPGYVDSIQKGIQKPKSGTQGNY DDDWKGFYSTDNKYDAAGYSVDNENPLSGKAGGVVKVTYPGLTKVLALKVDN AETIKKELGLSLTEPLMEQVGTEEFIKR FGDGASRVVLSLPFAEGSSSVEYINNWEQAKALSVELEINFETRGKRGQDAMYE YMAQACASEEDDTTVCCSMSYSWTGA LAIGLQGGGGSGGGSGSGGSGACYCRIPACIAGERRYGTCIYQGRLWAFCCGSGS HHHHHHKDEL |
| 67 | MKKTAIAIAVALAGFATVAQAANLAEEAFDLWNECAKACVLDLKDGVRSSRMS VDPAIADTNGQGVLHYSMVLEGGNDAL KLAIDNALSITSDGLTIRLEGGVEPNKPVRYSYTRQARGSWSLNWLVPIGHEKPS NIKVFIHELNAGNQLSHMSPIYTIE MGDELLAKLARDATFFVRAHESNEMQPTLAISHAGVSVVMAQTQPRREKRWSE WASGKVLCLLDPLDGVYNYLAQQRCNL DDTWEGKIYRVLAGNPAKHDLDIKPTVISHRLHFPEGGSLAALTAHQACHLPLET FTRHRQPRGWEQLEQCGYPVQRLVA LYLAARLSWNQVDQVIRNALASPGSGGDLGEAIREQPEQARLALTLAAAESERF VRQGTGNDEAGAANADVVSLTCPVAA GECAGPADSGDALLERNYPTGAEFLGDGGDVSFSTRGIFPKQYPIINFTTAGATV QSYTNFIRAVRGRLTTGADVRHEIP |

| | |
|---|---|
| | VLPNRVGLPINQRFILVELSNHAELSVTLALDVTNAYVVGYRAGNSAYFFHPDN<br>QEDAEAITHLFTDVQNRYTFAFGGNY<br>DRLEQLAGNLRENIELGNGPLEEAISALYYYSTGGTQLPTLARSFIICIQMISEAAR<br>FQYIEGEMRTRIRYNRRSAPDPS<br>VITLENSWGRLSTAIQESNQGAFASPIQLQRRNGSKFSVYDVSILIPIIALMVYRCA<br>PPPSSGSEEDDTTVCCSMSYSWT<br>GALGGGGSEESEESDDDMGFGLFDTGGEESEESDDDMGFGLFDTGSLQHHHHH<br>HKDEL |
| 68 | MKKTAIAIAVALAGFATVAQAANLAEEAFDLWNECAKACVLDLKDGVRSSRMS<br>VDPAIADTNGQGVLHYSMVLEGGNDALKLAIDNALSITSDGLTIRLE<br>GGVEPNKPVRYSYTRQARGSWSLNWLVPIGHEKPSNIKVFIHELNAGNQLSHMS<br>PIYTIEMGDELLAKLARDATFFVRAHESNEMQPTLAISHAGVSVVM<br>AQTQPRREKRWSEWASGKVLCLLDPLDGVYNYLAQQRCNLDDTWEGKIYRVL<br>AGNPAKHDLDIKPTVISHRLHFPEGGSLAALTAHQACHLPLETFTRHR<br>QPRGWEQLEQCGYPVQRLVALYLAARLSWNQVDQVIRNALASPGSGGDLGEAI<br>REQPEQARLALTLAAAESERFVRQGTGNDEAGAANADVVSLTCPVAA<br>GECAGPADSGDALLERNYPTGAEFLGDGGDVSFSTRGTQNWTVERLLQAHRQL<br>EERGYVFVGYHGTFLEAAQSIVFGGVRARSQDLDAIWRGFYIAGDPA<br>LAYGYAQDQEPDARGRIRNGALLRVYVPRS SLPGFYRTSLTLAAPEAAGEVERLI<br>GHPLPLRLDAITGPEEEGGRLETILGWPLAERTVVIPSAIPTDPR<br>NVGGDLDPSSIPDQEQAISALPDYASQPGQGAAAQELAEDVVCCSMSYAIGLQG<br>GGGSGGGSGSGGSGACYCRIPACIAGERRYGTCIYQGRLWAFCCGS<br>GSHHHHHHKDEL |

| SEQ<br>ID<br>NO | Nucleic acid sequence |
|---|---|
| 69 | atgaaaaagacagctatcgcgattgcagtggcactggctggtttcgctaccgtagc<br>gcaggccgcgaatttggccgaagaagctttcgacctctggaacgaatgcgccaaag<br>cctgcgtgctcgacctcaaggacggcgtgcgaccagccgcatgagcgtcgaccc<br>ggccatcgccgacaccaacggccagggcgtgctgcactactccatgGTCCTGGAGGGCGGCAACGACGC<br>GCTCAAGCTGGCCATCGACAACGCCCTCAGCATCACCAGCGACGGCCTGACC<br>ATCCGCCTCGAAGGCGGCGTCGAGCCGAACAAGCCGGTCGCTACAGCTACA<br>CGCGCCAGGCGCGCGGCAGTTGGTCGCTGAACTGGCTGGTACCGATCGGCCA<br>CGAGAAGCCCTCGAACATCAAGGTGTTCATCCACGAACTGAACGCCGGCAAC<br>CAGCTCAGCCACATGTCGCCGATCTACACCATCGAGATGGGCGACGAGTTGC<br>TGGCGAAGCTGGCGCGCGATGCCACCTTCTTCGTCAGGGCGCACGAGAGCAA<br>CGAGATGCAGCCGACGCTCGCCATCAGCCATGCCGGGGTCAGCGTGGTCATG<br>GCCCAGACCCAGCCGCGCCGGGAAAAGCGCTGGAGCGAATGGGCCAGCGGC<br>AAGGTGTTGTGCCTGCTCGACCCGCTGGACGGGGTCTACAACTACCTCGCCC<br>AGCAACGCTGCAACCTCGACGATACCTGGGAAGGCAAGATCTACCGGGTGCT<br>CGCCGGCAACCCGGCGAAGCATGACCTGGACATCAAACCCACGGTCATCAGT<br>CATCGCCTGCACTTTCCCGAGGGCGGCAGCCTGGCCGCGCTGACCGCGCACC<br>AGGCTTGCCACCTGCCGCTGGAGACTTTCACCCGTCATCGCCAGCCGCGCGG<br>CTGGGAACAACTGGAGCAGTGCGGCTATCCGGTGCAGCGGCTGGTCGCCCTC<br>TACCTGGCGGCGCGGCTGTCGTGGAACCAGGTCGACCAGGTGATCCGCAACG<br>CCCTGGCCAGCCCCGGCAGCGGCGGCGACCTGGGCGAAGCGATCCGCGAGC<br>AGCCGGAGCAGGCCCGTCTGGCCCTGACCCTGGCCGCCGCCGAGAGCGAGCG<br>CTTCGTCCGGCAGGGCACCGGCAACGACGAGGCCGGCGCGGCCAACGCCGA<br>CGTGGTGAGCCTGACCTGCCCGGTCGCCGCCGGTGAATGCGCGGGCCCGGCG<br>GACAGCGGCGACGCCCTGCTGGAGCGCAACTATCCCACTGGCGCGGAGTTCC<br>TCGGCGACGGCGGCgacgtcggcaccggtggcgctgatgatgttgttgattatctaaatcttttgtgatggaaaactt<br>ttcttcgtaccacgggactaaacctggttatgtagattccatcaaaaggtatacaaaagccaaaatctggtacacaaggaaatta<br>tgacgatgattggaaagggttttatagtaccgacaataaatacgacgtgcgggatactctgtagataataataataaaaccgctctctg<br>gaaaagctggaggcgtggtcaaagtgacgtatccaggactgacgaaggttctcgcactaaaagtggataatgccgaaactata<br>agaaagagttaggtttaagtctcactgaaccgttgatggagcaagtcggaacggaagagtttatcaaaaggttcggtgatggtgc<br>ttcgcgtgtagtgctcagccttccctttcgctgaggggagttctagcgttgaatatattaataactgggaacaggcgaaagcgttaa<br>gcgtagaacttgagattaattttgaaacccgtggaaaacgtcgccaagatgcgatgtatgagtatatggctcaagcctgtgcaG<br>AGGATGTCGTGTGCTGCTCGATGTCCTACGCAATTGGCCTGCAGGGCGGTGG<br>CGGTTCTGGCGGCGGCTCCGGTAGCGGCGGCTCCGGTGCGTGCTACTGTCGT<br>ATTCCGGCTTGCATCGCGGGTGAACGTCGTTACGGCACTTGTATTTATCAAGG<br>CCGCCTGTGGGCATTCTGCTGTGGTTCTGGTTCCCATCACCATCACCATCACA<br>AGGACGAGCTGTAA |
| 70 | atgaaaaagacagctatcgcgattgcagtggcactggctggtttcgctaccgtagcgcaggccgcgaatttggccgaagaagct<br>ttcgacctctggaacgaatgcgccaaagcctgcgtgctcgacctcaaggacggcgtgcgttccagccgcatgagcgtcgaccc<br>ggccatcgccgacaccaacggccagggcgtgctgcactactccatgGTCCTGGAGGGCGGCAACGACGC<br>GCTCAAGCTGGCCATCGACAACGCCCTCAGCATCACCAGCGACGGCCTGACC<br>ATCCGCCTCGAAGGCGGCGTCGAGCCGAACAAGCCGGTCGCTACAGCTACA<br>CGCGCCAGGCGCGCGGCAGTTGGTCGCTGAACTGGCTGGTACCGATCGGCCA<br>CGAGAAGCCCTCGAACATCAAGGTGTTCATCCACGAACTGAACGCCGGCAAC<br>CAGCTCAGCCACATGTCGCCGATCTACACCATCGAGATGGGCGACGAGTTGC<br>TGGCGAAGCTGGCGCGCGATGCCACCTTCTTCGTCAGGGCGCACGAGAGCAA<br>CGAGATGCAGCCGACGCTCGCCATCAGCCATGCCGGGGTCAGCGTGGTCATG<br>GCCCAGACCCAGCCGCGCCGGGAAAAGCGCTGGAGCGAATGGGCCAGCGGC<br>AAGGTGTTGTGCCTGCTCGACCCGCTGGACGGGGTCTACAACTACCTCGCCC<br>AGCAACGCTGCAACCTCGACGATACCTGGGAAGGCAAGATCTACCGGGTGCT |

-continued

```
    CGCCGGCAACCCGGCGAAGCATGACCTGGACATCAAACCCACGGTCATCAGT
    CATCGCCTGCACTTTCCCGAGGGCGGCAGCCTGGCCGCGCTGACCGCGCACC
    AGGCTTGCCACCTGCCGCTGGAGACTTTCACCCGTCATCGCCAGCCGCGCGG
    CTGGGAACAACTGGAGCAGTGCGGCTATCCGGTGCAGCGGCTGGTCGCCCTC
    TACCTGGCGGCGCGGCTGTCGTGGAACCAGGTCGACCAGGTGATCCGCAACG
    CCCTGGCCAGCCCCGGCAGCGGCGGCGACCTGGGCGAAGCGATCCGCGAGC
    AGCCGGAGCAGGCCCGTCTGGCCCTGACCCTGGCCGCCGCCGAGAGCGAGCG
    CTTCGTCCGGCAGGGCACCGGCAACGACGAGGCCGGCGCGGCCAACGCCGA
    CGTGGTGAGCCTGACCTGCCCGGTCGCCGCCGGTGAATGCGCGGGCCCGGCG
    GACAGCGGCGACGCCCTGCTGGAGCGCAACTATCCCACTGGCGCGGAGTTCC
    TCGGCGACGGCGGCGACGTCAGCTTCAGCACCCGCGGcatattccccaaacaatacccaatt
    ataaactttaccacagcgggtgccactgtgcaaagctacacaaactttatcagagctgttcgcggtcgtttaacaactggagctga
    tgtgagacatgaaataccagtgttgccaaacagagttggtttgcctataaaccaacggtttattttagttgaactctcaaatcatgca
    gagctttctgttacattagccctggatgtcaccaatgcatatgtggtcggctaccgtgctggaaatagcgcatatttctttcatcctga
    caatcaggaagatgcagaagcaatcactcatcttttcactgatgtcaaaatcgatatacattcgcctttggtggtaattatgatagac
    ttgaacaacttgctggtaatctgagagaaaatatcgagttgggaaatggtccactagaggaggctatctcagcgctttattattaca
    gtactggtggcactcagatccaactctggctcgttcctttataatttgcatccaaatgatttcagaagcagcaagattccaatatatt
    gagggagaaatgcgcacgagaattaggtacaaccggagatctgcaccagatcctagcgtaattacacttgagaatagttgggg
    gagactttccactgcaattcaagagtctaaccaaggagcctttgctagtccaattcaactgcaaagacgtaatggttccaaattcag
    tgtgtacgatgtgagtatattaatccctcatagctctcatggtgtatagatgcgcacctccaccatcgtcaggatccGAAGA
    TGTGGTGTGTTGTAGCATGTCGTAcGGCGGTGGCGGCTCAGAGGAATCCGAA
    GAATCCGATGATGACATGGGTTTTGGTCTGTTCGAcaccggtGGTGAGGAGTCCG
    AGGAATCCGACGACGATATGGGCTTCGGCCTGTTTGACaccggttctCTGCAGCAT
    CACCATCACCATCACAAGGACGAGCTGTAA 71  atgaaaaagacagctatcgcgattgcagtggcactggctggtncgctaccgtagcgcaggccgcgaatttggccgaagaagct
    ttcgacctctggaacgaatgcgccaaagcctgcgtgctcgacctcaaggacggcgtgcgttccagccgcatgagcgtcgaccc
    ggccatcgccgacaccaacggccagggcgtgctgcactactccatggTCCTGGAGGGCGGCAACGACGC
    GCTCAAGCTGGCCATCGACAACGCCCTCAGCATCACCAGCGACGGCCTGACC
    ATCCGCCTCGAAGGCGGCGTCGAGCCGAACAAGCCGGTGCGCTACAGCTACA
    CGCGCCAGGCGCGCGGCAGTTGGTCGCTGAACTGGCTGGTACCGATCGGCCA
    CGAGAAGCCCTCGAACATCAAGGTGTTCATCCACGAACTGAACGCCGGCAAC
    CAGCTCAGCCACATGTCGCCGATCTACACCATCGAGATGGGCGACGAGTTGC
    TGGCGAAGCTGGCGCGCGATGCCACCTTCTTCGTCAGGGCGCACGAGAGCAA
    CGAGATGCAGCCGACGCTCGCCATCAGCCATGCCGGGGTCAGCGTGGTCATG
    GCCCAGACCCAGCCGCGCCGGGAAAAGCGCTGGAGCGAATGGGCCAGCGGC
    AAGGTGTTGTGCCTGCTCGACCCGCTGGACGGGGTCTACAACTACCTCGCCC
    AGCAACGCTGCAACCTCGACGATACCTGGGAAGGCAAGATCTACCGGGTGCT
    CGCCGGCAACCCGGCGAAGCATGACCTGGACATCAAACCCACGGTCATCAGT
    CATCGCCTGCACTTTCCCGAGGGCGGCAGCCTGGCCGCGCTGACCGCGCACC
    AGGCTTGCCACCTGCCGCTGGAGACTTTCACCCGTCATCGCCAGCCGCGCGG
    CTGGGAACAACTGGAGCAGTGCGGCTATCCGGTGCAGCGGCTGGTCGCCCTC
    TACCTGGCGGCGCGGCTGTCGTGGAACCAGGTCGACCAGGTGATCCGCAACG
    CCCTGGCCAGCCCCGGCAGCGGCGGCGACCTGGGCGAAGCGATCCGCGAGC
    AGCCGGAGCAGGCCCGTCTGGCCCTGACCCTGGCCGCCGCCGAGAGCGAGCG
    CTTCGTCCGGCAGGGCACCGGCAACGACGAGGCCGGCGCGGCCAACGCCGA
    CGTGGTGAGCCTGACCTGCCCGGTCGCCGCCGGTGAATGCGCGGGCCCGGCG
    GACAGCGGCGACGCCCTGCTGGAGCGCAACTATCCCACTGGCGCGGAGTTCC
    TCGGCGACGGCGGCgacgtcggcaccggtggcgctgatgatgttgttgattatctaaatcttagtgatggaaaactt
    ttcttcgtaccacgggactaaacctggttatgtagattccattcaaaaaggtatacaaaagccaaatctggtacacaaggaaatta
    tgacgatgattggaaagggttttatagtaccgacaataaatacgacgctgcgggatactctgtagataatgaaaacccgctctctg
    gaaaagctggaggcgtggtcaaagtgacgtatccaggactgacgaaggttctcgcactaaaagttggataatgccgaaactatta
    agaaagagttaggtttaagtctcactgaaccgttgatggagcaagtcggaacggaagagtttatcaaaaggttcggtgatggtgc
    ttcgcgtgtagtgctcagccttccttcgctgaggggagttctagcgttgaatatattaataactgggaacaggcgaaagcgttaa
    gcgtagaacttgagattaattttgaaaccgtggaaaacgtggcgatgtatgagtatatggctcaggcctgtgcaTC
    TGAAGAAGATGACACGACCGTATGTTGCTCTATGAGCTACTCCTGGACTGGT
    GCGCTGGCAATTGGCCTGCAGGGCGGTGGCGGTTCTGGCGGCGGCTCCGGTA
    GCGGCGGCTCCGGTGCGTGCTACTGTCGTATTCCGGCTTGCATCGCGGGTGAA
    CGTCGTTACGGCACTTGTATTTATCAAGGCCGCCTGTGGGCATTCTGCTGTGG
    TTCTGGTTCCCATCACCATCACCATCACAAGGACGAGCTGTAA 72  atgaaaaagacagctatcgcgattgcagtggcactggctggtttcgctaccgtagcgcaggccgcgaatttggccgaagaagct
    ttcgacctctggaacgaatgcgccaaagcctgcgtgctcgacctcaaggacggcgtgcgttccagccgcatgagcgtcgaccc
    ggccatcgccgacaccaacggccagggcgtgctgcactactccatggTCCTGGAGGGCGGCAACGACGC
    GCTCAAGCTGGCCATCGACAACGCCCTCAGCATCACCAGCGACGGCCTGACC
    ATCCGCCTCGAAGGCGGCGTCGAGCCGAACAAGCCGGTGCGCTACAGCTACA
    CGCGCCAGGCGCGCGGCAGTTGGTCGCTGAACTGGCTGGTACCGATCGGCCA
    CGAGAAGCCCTCGAACATCAAGGTGTTCATCCACGAACTGAACGCCGGCAAC
    CAGCTCAGCCACATGTCGCCGATCTACACCATCGAGATGGGCGACGAGTTGC
    TGGCGAAGCTGGCGCGCGATGCCACCTTCTTCGTCAGGGCGCACGAGAGCAA
    CGAGATGCAGCCGACGCTCGCCATCAGCCATGCCGGGGTCAGCGTGGTCATG
    GCCCAGACCCAGCCGCGCCGGGAAAAGCGCTGGAGCGAATGGGCCAGCGGC
    AAGGTGTTGTGCCTGCTCGACCCGCTGGACGGGGTCTACAACTACCTCGCCC
    AGCAACGCTGCAACCTCGACGATACCTGGGAAGGCAAGATCTACCGGGTGCT
    CGCCGGCAACCCGGCGAAGCATGACCTGGACATCAAACCCACGGTCATCAGT
    CATCGCCTGCACTTTCCCGAGGGCGGCAGCCTGGCCGCGCTGACCGCGCACC
    AGGCTTGCCACCTGCCGCTGGAGACTTTCACCCGTCATCGCCAGCCGCGCGG
    CTGGGAACAACTGGAGCAGTGCGGCTATCCGGTGCAGCGGCTGGTCGCCCTC
    TACCTGGCGGCGCGGCTGTCGTGGAACCAGGTCGACCAGGTGATCCGCAACG
```

-continued

```
    CCCTGGCCAGCCCCGGCAGCGGCGGCGACCTGGGCGAAGCGATCCGCGAGC
    AGCCGGAGCAGGCCCGTCTGGCCCTGACCCTGGCCGCCGCCGAGAGCGAGCG
    CTTCGTCCGGCAGGGCACCGGCAACGACGAGGCCGGCGCGGCCAACGCCGA
    CGTGGTGAGCCTGACCTGCCCGGTCGCCGCCGGTGAATGCGCGGGCCCGGCG
    GACAGCGGCGACGCCCTGCTGGAGCGCAACTATCCCACTGGCGCGGAGTTCC
    TCGGCGACGGCGGCGACGTCAGCTTCAGCACCCGCGGcatattcccccaaacaatacccaatt
    ataaactttaccacagcgggtgccactgtgcaaagctacacaaactttatcagagctgttcgcggtcgtttaacaactggagctga
    tgtgagacatgaaataccagtgttgccaaacagagttggtttgcctataaccaacggtttattttagttgaactctcaaatcatgca
    gagattctgttacattagccctggatgtcaccaatgcatatgtggtcggctaccgtgctggaaatagcgcatatttattcatcctga
    caatcaggaagatgcagaagcaatcactcatatttcactgatgttcaaaatcgatatacattcgcattggtggtaattatgatagac
    ttgaacaacttgctggtaatctgagagaaaatatcgagttgggaaatggtccactagaggaggctatctcagcgctttattattaca
    gtactggtggcactcagcttccaactctggctcgttccttataatttgcatccaaatgatttcagaagcagcaagattccaatatatt
    gagggagaaatgcgcacgagaattaggtacaaccggagatctgcaccagatcctagcgtaattacacttgagaatagttgggg
    gagactttccactgcaattcaagagtctaaccaaggagccttTgctagtccaattcaactgcaaagacgtaatggttccaaattcag
    tgtgtacgatgtgagtatattaatccctatcatagactcatggtgtatagatgcgcacctccaccatcgtcaggatccGAAGA
    AGATGACACGACCGTATGTTGCTCTATGAGCTACTCCTGGACTGGTGCGCTGG
    GCGGTGGCGGCTCAGAGGAATCCGAAGAATCCGATGATGACATGGGTTTTGG
    TCTGTTCGACaccggtGGTGAGGAGTCCGAGGAATCCGACGACGATATGGGCTT
    CGGCCTGTTTGACaccggttctCTGCAGCATCACCATCACCATCACAAGGACGAGC
    TGTAA 73 atgaaaaagacagctatcgcgattgcagtggcactggctggtttcgctaccgtagcgcaggccgcgaatttggccgaagaagct
    ttcgacctctggaacgaatgcgccaaagcctgcgtgctcgacctcaaggacggcgtgcgttccagccgcatgagcgtcgaccc
    ggccatcgccgacaccaacggccagggcgtgctgcactactccatgGTCCTGGAGGGCGGCAACGACGC
    GCTCAAGCTGGCCATCGACAACGCCCTCAGCATCACCAGCGACGGCCTGACC
    ATCCGCCTCGAAGGCGGCGTCGAGCCGAACAAGCCGGTGCGCTACAGCTACA
    CGCGCCAGGCGCGCGGCAGTTGGTCGCTGAACTGGCTGGTACCGATCGGCCA
    CGAGAAGCCCTCGAACATCAAGGTGTTCATCCACGAACTGAACGCCGGCAAC
    CAGCTCAGCCACATGTCGCCGATCTACACCATCGAGATGGGCGACGAGTTGC
    TGGCGAAGCTGGCGCGCGATGCCACCTTCTTCGTCAGGGCGCACGAGAGCAA
    CGAGATGCAGCCGACGCTCGCCATCAGCCATGCCGGGGTCAGCGTGGTCATG
    GCCCAGACCCAGCCGCGCCGGGAAAAGCGCTGGAGCGAATGGGCCAGCGGC
    AAGGTGTTGTGCCTGCTCGACCCGCTGGACGGGGTCTACAACTACCTCGCCC
    AGCAACGCTGCAACCTCGACGATACCTGGGAAGGCAAGATCTACCGGGTGCT
    CGCCGGCAACCCGGCGAAGCATGACCTGGACATCAAACCCACGGTCATCAGT
    CATCGCCTGCACTTTCCCGAGGGCGGCAGCCTGGCCGCGCTGACCGCGCACC
    AGGCTTGCCACCTGCCGCTGGAGACTTTCACCCGTCATCGCCAGCCGCGCGG
    CTGGGAACAACTGGAGCAGTGCGGCTATCCGGTGCAGCGGCTGGTCGCCCTC
    TACCTGGCGGCGCGGCTGTCGTGGAACCAGGTCGACCAGGTGATCCGCAACG
    CCCTGGCCAGCCCCGGCAGCGGCGGCGACCTGGGCGAAGCGATCCGCGAGC
    AGCCGGAGCAGGCCCGTCTGGCCCTGACCCTGGCCGCCGCCGAGAGCGAGCG
    CTTCGTCCGGCAGGGCACCGGCAACGACGAGGCCGGCGCGGCCAACGCCGA
    CGTGGTGAGCCTGACCTGCCCGGTCGCCGCCGGTGAATGCGCGGGCCCGGCG
    GACAGCGGCGACGCCCTGCTGGAGCGCAACTATCCCACTGGCGCGGAGTTCC
    TCGGCGACGGCGGCGACGTCAGCTTCAGCACCCGCGGCACGCAGAACTGGAC
    GGTGGAGCGGCTGCTCCAGGCGCACCGCCAACTGGAGGAGCGCGGCTATGTG
    TTCGTCGGCTACCACGGCACCTTCCTCGAAGCGGCGCAAAGCATCGTCTTCG
    GCGGGGTGCGCGCGCGCAGCCAGGACCTCGACGCGATCTGGCGCGGTTTCTA
    TATCGCCGGCGATCCGGCGCTGGCCTACGGCTACGCCCAGGACCAGGAACCC
    GACGCACGCGGCCGGATCCGCAACGGTGCCCTGCTGCGGGTCTATGTGCCGC
    GCTCGAGCCTGCCGGGCTTCTACCGCACCAGCCTGACCCTGGCCGCGCCGGA
    GGCGGCGGGCGAGGTCGAACGGCTGATCGGCCATCCGCTGCCGCTGCGCCTG
    GACGCCATCACCGGCCCCGAGGAGGAAGGCGGGCGCCTGGAGACCATTCTC
    GGCTGGCCGCTGGCCGAGCGCACCGTGGTGATTCCCTCGGCGATCCCCACCG
    ACCCGCGCAACGTCGGCGGCGACCTCGACCCGTCCAGCATCCCGGACCAAGA
    ACAGGCGATCAGCGCCCTGCCGGACTACGCCAGCCAGCCCGGGcaaggaGCggcc
    GCGCAGGAGCTAGCGGAGGATGTCGTGTGCTGCTCGATGTCCTACGCAATTG
    GCCTGCAGGGCGGTGGCGGTTCTGGCGGCGGCTCCGGTAGCGGCGGCTCCGG
    TGCGTGCTACTGTCGTATTCCGGCTTGCATCGCGGGTGAACGTCGTTACGGCA
    CTTGTATTTATCAAGGCCGCCTGTGGGCATTCTGCTGTGGTTCTGGTTCCCATC
    ACCATCACCATCACAAGGACGAGCTGTAA
```

In particular embodiments, there is provided a pharmaceutical composition comprising a multi-domain toxin protein conjugate or toxin fusion protein as disclosed herein; and a pharmaceutically acceptable carrier.

In another aspect, the invention provides a method for treating a disease, the method comprising administering to a subject in need thereof a therapeutically effective amount of a multi-domain toxin protein conjugate, or a toxin fusion protein, or a pharmaceutical composition, as disclosed herein.

In another aspect, the invention provides a multi-domain toxin protein conjugate or toxin fusion protein as disclosed herein for treating a disease.

In particular embodiments, the disease is selected from an infectious disease and cancer.

In particular embodiments, the infectious disease is caused by a pathogen selected from the group consisting of a virus, a bacteria and a fungus. In particular embodiments, the pathogen is characterized by having a protease (the nucleic acid encoding the protease and/or the actual protein) that is not expressed endogenically by a healthy cell.

Particular embodiments of the virus are as hereinbefore described.

In a particular embodiment, the virus is HCV.

In particular embodiments, the multi-domain toxin protein conjugate or toxin fusion protein is administered as a single dose or over a period of time in multiple doses.

In particular embodiments, the multi-domain toxin protein conjugate or toxin fusion protein is formulated for administration by a route selected from parenteral (for example for infusion, bolus injection or direct injection to an organ or infection site); and oral.

Other objects, features and advantages of the present invention will become clear from the following description and examples.

DEFINITIONS

The term "protein conjugate" as used herein refers to a polypeptide structure comprising a plurality of segments or domains in association through covalent bonds, non-covalent bonds or a combination thereof. The segments and domains may be from heterologous proteins, or from the same protein.

The term "protein domain" as used herein refers to a polypeptide unit that is a structural and/or functional unit of a larger protein, either as found in nature, such as a multi-domain bacterial or plant toxin, or a recombinantly engineered multi-domain protein. Reference to a protein domain includes both the situation when the protein domain is contained within the larger protein and when it is separate therefrom.

The term "segment" as used herein refers to a peptide or polypeptide fragment of a larger protein, which may or may not be distinguished on the basis of structural and/or functional characteristics. Reference to a segment includes both the situation when the segment is contained within the larger protein and when it is separate therefrom.

The term "fusion protein" as used herein refers to a multi-segment continuous polypeptide, wherein at least some of the segments are derived from heterologous proteins.

The term "heterologous" in reference to portions of a larger protein molecule indicates that the larger polypeptide comprises two or more subsequences that are not found in the same relationship in nature. For example, a fusion protein may comprise the heterologous segments of a cell binding domain from a first bacterial toxin e.g. *Pseudomonas* exotoxin, and a catalytic domain from a different second bacterial toxin e.g. diphtheria toxin. In general, heterologous protein segments are joined together to form a fusion protein using recombinant engineering techniques, in which nucleic acid molecules encoding the corresponding heterologous protein segments are produced, ligated together into a plasmid with appropriate regulatory elements and expressed in a recombinant organism. Similarly, "heterologous" nucleic acid molecules in reference to portions of a larger nucleic acid molecule means that the larger nucleic acid comprises two or more subsequences that are not found in the same relationship in nature.

The term "linker" as used herein refers to an internal amino acid sequence or a single amino acid which is covalently linked between two distinct segments of a fusion protein or domains of a fusion protein or protein conjugate. In general, a linker has no functional activity of its own and preferably does not interfere with the activity of any of the functional units of the protein, but serves to provide a spatial separation between such segments or domains so as to reduce or avoid steric hindrance between or among them.

The term "inhibitory peptide" as used herein refers to a peptide or protein which reversibly inhibits the activity of a catalytic domain of a catalytic protein, for example, by physically blocking the active site, by physically blocking an allosteric site, by providing a physical barrier which prevents interaction of the catalytic domain with its substrate, or by destabilizing the catalytic domain in any manner.

As used herein, the singular forms "a", "an" and "the" include plural forms unless the context clearly dictates otherwise.

Protein Conjugates and Fusion Proteins

The protein conjugates and fusion proteins of the invention comprise a plurality of functional domains which respectively confer upon the protein the ability to bind to a cell, translocate across the cell membrane, and exert a toxic effect by catalyzing an enzymatic activity. In addition, the proteins comprise an inhibitory peptide which neutralizes the activity of the toxic domain until and unless cleaved by a specific protease.

The functional domains of the proteins of the invention include domains from plant, bacterial or fungal protein toxins. As used herein, "plant toxins", "bacterial toxins" and "fungal toxins" respectively refer any toxin produced by a plant, bacteria or fungus. The toxin domains may be wild-type proteins or recombinant proteins. Further, such toxins include those which are variously classified according to their mechanism of action and/or structural organization, for example ADP-ribosylating toxins such as *Pseudomonas* exotoxin and diphtheria toxin; N-glycosidase containing ribosome inactivating toxins (RIPs) such as ricin, abrin, and Shiga-like toxin 1, including those variously classified as Type I, Type II and Type III RIPs; and binary bacterial toxins to refer to those which comprise separate cell binding and catalytic domains, including for example, anthrax toxin, pertussis toxins, cholera toxin, *E. coli* heat-labile enterotoxin, Shiga toxin, pertussis toxin, *Clostridium perfringens* iota toxin, *Clostridium spiroforme* toxin, *Clostridium difficile* toxin, *Clostridium botulinum* C2 toxin, and *Bacillus cereus* vegetative insecticidal protein.

The proteins of the invention may include domains from different i.e. heterologous toxins which are joined together by chemical conjugation (and/or non-covalent interactions), or often preferably those which are expressed as recombinant fusion proteins. In addition, the cell binding domain of the protein disclosed herein may include a cell binding domain of a toxin, and additionally or alternately comprise a cell targeting antibody of a cell surface receptor ligand. All of these types of moieties may be found together in a single fusion protein or protein conjugate, and may further include various modifications.

As used herein the term "cell binding domain" refers to a protein domain which has affinity for a receptor expressed on a target cell. The cell binding domain of the protein of the invention may be a cell binding domain of a toxin; or may alternately or in addition comprise an antibody or a cell surface receptor ligand.

A cell binding domain of a toxin may be a separate functional domain, as in the case of bacterial binary toxins, or it may be a toxin which comprises as single chain which possesses cell binding and catalytic properties.

Cell binding domains of toxins include for example, domain Ia of *Pseudomonas* exotoxin; the R domain of diphtheria toxin; the B chain of ricin; anthrax protective antigen; the B chain of cholera toxin; the B chain of tetanus toxin; the heavy chain of botulinum toxin, the B chain of *Clostridium difficile* toxin; and anthrax protective antigen. Additional possibilities include cell binding domains of verotoxin, pertussis toxin, abrin, Shiga-like toxin 1 (SLT-1), modecin, volkensin, visumin, trichosanthin, maize RIP, luffaculin 1, and alpha-luffin.

A "cell translocation domain" refers to a protein domain which causes or facilitates transport of a protein according to the invention across a cell membrane and into the cytosol. The cell translocation domain may be that of a plant, bacterial or fungal toxin, such as a cell translocation domain of *Pseudomonas* exotoxin diphtheria toxin, anthrax toxin, botulinum toxin or *Clostridium difficile* toxin; or may be from a viral protein, such as the HIV TAT protein transduction domain.

The cell binding domain and/or the cell translocation domain may comprise a cell-penetrating peptide, which is any short peptide that promotes and facilitates transport of a protein across the plasma membrane and into a cell. Cell-penetrating peptides are reviewed for example in Sawant et al Mol Biosyste., 2010, 6,628-640.

Non limiting examples of cell-penetrating peptides include various polyarginines, such as $R_8$; $TAT_{49-57}$ (RKKRRQRRR); TAT (GRKKRRQRRRPPQ), Pep-1 (KETWWETWWTEWSQPKKKRKV) Antennapedia cell-penetrating peptide, also referred to as "penetratin" (RQIKIWFQNRRMKWKK), transportan (GWTLNSAGYLLGKINLKALAALAKKIL).

Various nuclear localization sequences (NLS) may also serve as cell-penetrating peptides, such as the sequence PKKKRKV (SEQ ID NO: 124) from the SV40 Large T-antigen (see for example, Kalderon et al., (1984) Cell 39 (3 Pt 2): 499-509); the NLS of nucleoplasmin (KR[PAATKKAGQA]KKKK (SEQ ID NOs: 125-127); see for example, Dingwall et al., (September 1988). J Cell Biol. 107 (3): 841-9); the acidic M9 domain of hnRNP A1; the sequence KIPIK (SEQ ID NO: 128) in yeast transcription repressor Matα2, and the complex signals of U snRNPs.

A "toxin catalytic domain" refers to a protein domain derived from a toxin which exerts a toxic effect on a cell by catalyzing a enzymatic reaction which is detrimental to the cell. Toxin catalytic domains include *Pseudomonas* exotoxin domain 3; diphtheria toxin domain C; the A chain of tetanus toxin; the A chain of cholera toxin; *Clostridium botulinum* C2 subunit A; *Clostridium difficile* toxin subunit A; lethal factor of anthrax toxin; Shiga toxin subunit A; pertussis toxin Sl subunit; the A chain of ricin; and corresponding domains of verotoxin, abrin, Shiga-like toxin 1 (SLT-1), modecin, volkensin, visumin, trichosanthin, maize RIP, luffaculin 1, and alpha-luffin It is to be understood that a toxin catalytic domain may be from a toxin having only a catalytic i.e. A chain, such as for example the plant toxins trichosanthin, MMC and pokeweed antiviral proteins, d wheat germ inhibitor, and the fungal toxins alpha-sarcin, restrictocin, mitogillin, neomycin and phenomycin.

It is to be understood that a toxin domain for use in the invention, such as a cell binding domain or a catalytic domain, may be altered relative to that of the native toxin domain. Such alterations may include for example truncation or chemical modification. For example, a toxin catalytic domain may be truncated to contain only that portion of the native chain which is necessary for exerting its cytotoxic effect. For example, the first 30 amino acids of the ricin A chain may be removed resulting in a truncated A chain which retains toxic activity. A truncated domain may be prepared by expression of a truncated gene or by proteolytic degradation. Similarly, a protein of the invention may contain only a portion of a toxin cell binding domain that is necessary or sufficient for cell binding; and only a portion of a toxin cell translocation domain that is necessary or sufficient for transport into the cell cytoplasm.

In addition, domains may be modified by having a different glycosylation state relative to the native toxin domain. Thus, a domain may be glycosylated or non-glycosylated. Glycosylated proteins may be obtained by expression in the appropriate host cell capable of glycosylation. Non-glycosylated proteins may be obtained by expression in nonglycosylating host cells or by treatment to remove or destroy the all or some of the carbohydrate moieties.

A sequence containing a cleavage recognition site for a viral, fungal, parasitic or cancer associated protease may be selected based on the pathogen-infected or malignant diseased cell which is to be targeted by the protein of the invention. The cleavage recognition site may be selected from sequences known to encode a cleavage recognition site for a viral, bacterial, fungal or cancer associated protease. Sequences encoding cleavage recognition sites may be identified by testing the expression product of the sequence for susceptibility to cleavage by a viral, bacterial, fungal or cancer associated protease. A polypeptide containing the suspected cleavage recognition site may be incubated with a protease and the amount of cleavage product determined (Dilannit, 1990, J. Biol. Chem. 285: 17345-17354 (1990)).

Substrates and cleavage recognition sequence of HCV NS3 are disclosed in WO 2009/022236 and referenced disclosed therein.

Substrates of proteases from human cytomegalovirus, human herpes virus, varicalla zoster virus and infectious laryngotracheitis virus, and enzymatic activity assay methodologies, are disclosed for example in Liu F. & Roizman, B. (J. Virol. 65:5149-5156 (1991)) and Welch, A. R. (Proc. Natl. Acad. Sci. USA 88:10792-10796 (1991)).

Substrates of Epstein-Barr virus protease, and enzymatic activity assay methodology is disclosed for example in Welch, A. R. (Proc. Natl. Acad. Sci. USA 88:10792-10796 (1991)).

Substrates of poliovirus protease, and enzymatic activity assay methodology is disclosed for example in Weidner, J. R. et al. (Arch. Biochem. Biophys. 286:402-408 (1991)).

Substrates of proteases associated with *Candida* yeasts, and enzymatic activity, including that of aspartic proteinases associated specifically with numerous virulent strains including *Candida albicans, Candida tropicalis*, and *Candida parapsilosis* is disclosed for example in Abad-Zapatero, C. et al., Protein Sci. 5:640-652 (1996); Cutfield, S. M. et al., Biochemistry 35:398-410 (1995); Ruchel, R. et al, Zentralbl. Bakteriol. Mikrobiol Hyg. I Abt. Orig. A. 255:537-548 (1983); Remold, H. et al., Biochim. Biophys. Acta 167:399-406 (1968)).

The fusion proteins and complexes of the invention further include an inhibitory peptide which specifically inhibits the catalytic domain. The inhibitory peptide may specifically inhibit a catalytic domain that has ADP-ribosyl transferase activity, for example a catalytic domain of *Pseudomonas* exotoxin, diphtheria toxin, or *Clostridium difficile* toxin. Alternately, the inhibitory peptide may specifically inhibit a catalytic domain that has N-glycosidase activity, for example a catalytic domain of RIP toxin such as ricin, abrin, Shiga-like toxin 1 (SLT-1), modecin, volkensin, visumin, trichosanthin, maize RIP, luffaculin 1 or alpha-luffin.

In additional embodiment, the inhibitory peptide may correspond to an autoinhibiting fragment of a toxin that has ADP-ribosyl transferase activity, or a toxin that has N-glycosidase activity. Toxins that contain autoinhibitory fragments include for example, mosquitocidal toxin (MTX) from *Bacillus sphaericus* SSII-1 and maize RIP A defensin peptide or a fragment thereof may serve as the inhibitory peptide, when the fusion protein or conjugate includes a catalytic domain that has ADP-ribosyl transferase activity. The defensin peptide may be a human alpha defensin peptide, such as HNP-1; HNP-2; HNP-3; HNP-4; HD-5 or HD-6. In a particular embodiment, the human defensin peptide is human HNP-1. Human alpha defensin peptides are disclosed for example, in Ericksen et al., Antimicrob Agents Chemother. 2005; 49:269-75; Ganz et al., J Clin Invest. 1985; 76:1427-35; Valore et al., Blood. 1992; 79:1538-44; and Mallow et al., J Biol Chem. 1996; 271:4038-45.

In a particular embodiment, the inhibitory peptide comprises a fragment of a human alpha defensin peptide selected from HNP-1, HNP-2 and HNP-3; and the catalytic domain is from a toxin selected from *Pseudomonas* exotoxin, diphtheria toxin, *Clostridium difficile* toxin and anthrax toxin.

A ribosomal protein or a fragment thereof may serve as the inhibitory peptide when the fusion protein or conjugate includes a catalytic domain that has N-glycosidase activity. For example, the inhibitory peptide may be a fragment of a ribosomal stalk protein selected from ribosomal stalk protein P1 and ribosomal stalk protein P2. The interaction between ribosomal stalk proteins P1 and P2 and ricin toxin is disclosed for example, in Chiou et al., Mol Microbiol 2008, December 70(6), 1441-1452.

In a particular embodiment, the inhibitory peptide comprises a fragment of a ribosomal stalk protein selected ribosomal stalk protein P1 and ribosomal stalk protein P2; and the catalytic domain is from a toxin selected from ricin, abrin, Shiga-like toxin 1 (SLT-1), modecin, volkensin, visumin, trichosanthin, maize RIP, luffaculin 1 and alpha-luffin.

For preparing recombinant proteins, a nucleic acid can be amplified from cDNA or genomic DNA using appropriate oligonucleotide primers and standard PCR amplification techniques. The nucleic acid so amplified can be cloned into an appropriate vector and characterized by DNA sequence analysis. It will be appreciated that cDNA may be prepared from mRNA, by isolating total cellular mRNA by a variety of techniques. cDNA is then synthesized from the mRNA using reverse transcriptase (for example, Moloney MLV reverse transcriptase, or AMV reverse transcriptase. Such methods may be used to obtain the coding sequences of toxins or domains thereof from plants, bacteria or fungi.

Sequences encoding toxin domains may be obtained by selective amplification of a coding region, using sets of degenerative primers or probes for selectively amplifying the coding region in a genomic or cDNA library. Appropriate primers may be selected from the nucleic acid sequence the toxin domains of interest. It is also possible to design synthetic oligonucleotide primers from the nucleotide sequences for use in PCR. Suitable primers may be selected from the sequences encoding regions of toxin proteins which are highly conserved.

The nucleic acid molecule of the invention may also be prepared by site directed mutagenesis. Site directed mutagenesis may be accomplished by DNA amplification of mutagenic primers in combination with flanking primers.

The nucleic acid molecule of the invention may also be prepared by total gene synthesis assembled from synthesized oligonucleotides, as is known in the art.

The nucleic acid molecule of the invention may also encode a fusion protein. A sequence encoding a heterologous linker sequence and encoding a cleavage recognition site for a disease-specific protease may be cloned from a cDNA or genomic library or chemically synthesized based on the known sequence of such cleavage sites. The linker sequence may then be fused in frame with the sequences encoding domains of a toxin for expression as a fusion protein. It will be appreciated that a nucleic acid molecule encoding a fusion protein may contain a sequence encoding different functional domains e.g. cell binding and catalytic, from the same toxin or from different toxins. For example, the cell binding domain may be derived from *Pseudomonas* exotoxin, and the catalytic domain may be derived from ricin. A protein may also be prepared by chemical conjugation of the various domains or segments and linker sequence using conventional coupling agents for covalent attachment.

A nucleic acid molecule may comprise, as operatively linked elements, a transcriptional promoter; a nucleic acid sequence encoding a secretion signal peptide; a transcriptional termination signal; a selectable marker and a nucleic acid sequence encoding the recombinant toxic protein of the invention. The term "operatively linked" as used herein indicates that the segments are arranged so that they function in their intended purposes, e.g. transcription begins in the promoter, proceeds through the coding regions and halts at the terminator. The nucleic acid molecules may also include sequences such that homologous recombination occurs between the vector and the genomic DNA of the yeast.

Nucleic acid molecules encoding the protein comprising the domains of interest may be incorporated in a known manner into an appropriate expression vector which ensures good expression of the protein. Possible expression vectors include cosmids, plasmids, or modified viruses (e.g. replication defective retroviruses, adenoviruses and adeno-associated viruses), so long as the vector is compatible with the host cell used. The expression vectors are "suitable for transformation of a host cell", which means that the expression vectors contain a nucleic acid molecule of the invention and regulatory sequences selected on the basis of the host cells to be used for expression, which is operatively linked to the nucleic acid molecule. Operatively linked is intended to mean that the nucleic acid is linked to regulatory sequences in a manner which allows expression of the nucleic acid.

The invention therefore contemplates a recombinant expression vector of the invention containing a nucleic acid molecule of the invention, or a fragment thereof, and the necessary regulatory sequences for the transcription and translation of the inserted protein sequence.

Suitable regulatory sequences may be derived from a variety of sources, including bacterial, fungal, yeast, viral, mammalian, or insect genes (For example, see the regulatory sequences described in Goeddel, Gene Expression Technology: Methods in Enzymology 185, Academic Press, San Diego, Calif. (1990). Selection of appropriate regulatory sequences is dependent on the host cell chosen, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector. It will also be appreciated that the necessary regulatory sequences may be supplied by the native toxins and/or flanking regions.

The recombinant expression vectors of the invention may also contain a selectable marker gene which facilitates the selection of host cells transformed or transfected with a recombinant molecule of the invention. Examples of selectable marker genes are genes encoding a protein such as G418 and hygromycin which confer resistance to certain drugs, beta-galactosidase, chloramphenicol acetyltransferase, firefly luciferase, or an immunoglobulin or portion thereof such as the Fc portion of an immunoglobulin preferably IgG. Other selectable marker genes include the ARG4 (argininosuccinate lyase) genes from *P. pastoris* and *S. cerevisiae*, the HIS4 (histidinol dehydrogenase) genes from *P. pastoris* and *S. cerevisiae*, the uracil utilization gene (URA), genes providing the capacity for leucine or adenine synthesis, and the like. Transcription of the selectable marker gene is monitored by changes in the concentration of the selectable marker protein such as beta-galactosidase, chloramphenicol acetyltransferase, or firefly luciferase. If the selectable marker gene encodes a protein conferring drug resistance, such as neomycin resistance, then transformant cells can be selected with G418. Cells that have incorporated the selectable marker gene will survive, while the other cells die. This makes it possible to visualize and assay for expression of recombinant expression vectors of the invention and in particular to determine the effect of a mutation on expression and phenotype. It will be appreciated that selectable markers can be introduced on a separate vector from the nucleic acid of interest.

The recombinant expression vectors may also contain genes which encode a fusion moiety which provides increased expression of the recombinant protein; increased solubility of the recombinant protein; and aid in the purification of the target recombinant protein by acting as a ligand in affinity purification. For example, a proteolytic cleavage site may be added to the target recombinant protein to allow separation of the recombinant protein from the fusion moiety subsequent to purification of the fusion protein. Typical fusion expression vectors include pGEX (Amrad Corp., Melbourne, Australia), pMAL (New England Biolabs, Beverly, Mass.) and pRIT5 (Pharmacia, Piscataway, N.J.) which fuse glutathione S-transferase (GST), maltose E binding protein, or protein A, respectively, to the recombinant protein.

Recombinant expression vectors can be introduced into host cells to produce a transformant host cell. The term "transformant host cell" is intended to include prokaryotic and eukaryotic cells which have been transformed or transfected with a recombinant expression vector of the invention. The terms "transformed with", "transfected with", "transformation" and "transfection" are intended to encompass introduction of nucleic acid (e.g. a vector) into a cell by one of many possible techniques known in the art. Prokaryotic cells can be transformed with nucleic acid by, for example, electroporation or calcium-chloride mediated transformation. Nucleic acid can be introduced into mammalian cells via conventional techniques such as calcium phosphate or calcium chloride co-precipitation, DEAE-dextran mediated transfection, lipofectin, electroporation or microinjection. Suitable methods for transforming and transfecting host cells can be found in Sambrook et al. (Molecular Cloning: A Laboratory Manual, 2nd Edition, Cold Spring Harbor Laboratory press (1989)), and other laboratory textbooks.

Suitable host cells include a wide variety of prokaryotic and eukaryotic host cells. For example, the proteins of the invention may be expressed in bacterial cells such as *E. coli*, insect cells (using baculovirus), yeast cells or mammalian cells. Other suitable host cells can be found in Goeddel, Gene Expression Technology: Methods in Enzymology 185, Academic Press, San Diego, Calif. (1991).

More particularly, bacterial host cells suitable for carrying out the present invention include *E. coli, B. subtilis, Salmonella typhimurium*, and various species within the genus' *Pseudomonas, Streptomyces*, and *Staphylococcus*, as well as many other bacterial species well known to one of ordinary skill in the art. Suitable bacterial expression vectors preferably comprise a promoter which functions in the host cell, one or more selectable phenotypic markers, and a bacterial origin of replication. Representative promoters include the beta-lactamase (penicillinase) and lactose promoter system (see Chang et al., Nature 275:615 (1978)), the trp promoter (Nichols and Yanofsky, Meth in Enzymology 101:155, (1983) and the tac promoter (Russell et al., Gene 20: 231, (1982)). Representative selectable markers include various antibiotic resistance markers such as the kanamycin or ampicillin resistance genes. Suitable expression vectors include but are not limited to bacteriophages such as lambda derivatives or plasmids such as pBR322 (Bolivar et al., Gene 2:9 S, (1977)), the pUC plasmids pUC18, pUC19, pUC 118, pUC 119 (see Messing, Meth in Enzymology 101:20-77, 1983 and Vieira and Messing, Gene 19:259-268 (1982)), and pNH8A, pNH16a, pNH18a, and Bluescript M13 (Stratagene, La Jolla, Calif.). Typical fusion expression vectors which may be used are discussed above, e.g. pGEX (Amrad Corp., Melbourne, Australia), pMAL (New England Biolabs, Beverly, Mass.) and pRIT5 (Pharmacia, Piscataway, N.J.). Examples of inducible non-fusion expression vectors include pTrc (Amann et al., Gene 69:301-315 (1988)) and pET 11d (Studier et al., Gene Expression Technology Methods in Enzymology 185, Academic Press, San Diego, Calif., 60-89 (1990)).

Yeast and fungi host cells suitable for carrying out the present invention include, but are not limited to *Saccharomyces cerevisae*, the genera *Pichia, Kluyveromyces, Hanensula, Candida* and *Torulopsis* and various species of the genus *Aspergillus*. Examples of vectors for expression in yeast *S. cerivisae* include pYepSec1 (Baldari. et al., Embo J. 6:229-234 (1987)), pMFa (Kurjan and Herskowitz, Cell 30:933-943 (1982)), pJRY88 (Schultz et al., Gene 54:113-123 (1987)), and pYES2 (Invitrogen Corporation, San Diego, Calif.). Examples of vectors for expression in yeast *P. pastoris* include pPICZ.alpha.A. Protocols for the transformation of yeast and fungi are well known to those of ordinary skill in the art. (see Hinnen et al., Proc. Natl. Acad. Sci. USA 75:1929 (1978); Itoh et al., J. Bacteriology 153:163 (1983), and Cullen et al. (Bio/Technology 5:369 (1987)).

Pharmaceutical Compositions and Therapeutic Uses

Protein toxins of the invention and pharmaceutical compositions comprising such the modified bacterial protein toxins can be administered directly to the patient, e.g., for inhibition of virally infected cell growth in vivo, or for inhibition of cancer, tumor, or precancer cell growth in vivo.

Administration is by any of the routes normally used for introducing a compound into ultimate contact with the tissue to be treated. The compounds are administered in any suitable manner, preferably with pharmaceutically acceptable carriers. Suitable methods of administering such compounds are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention (see, e.g., Remington's Pharmaceutical Sciences, 17th ed. 1985)).

Formulations suitable for parenteral administration, such as, for example, by intravenous, intramuscular, intradermal, and subcutaneous routes, include aqueous and non¬ aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. The formulations of compounds can be presented in unit-dose or multi-dose sealed containers, such as ampules and vials. Injection solutions and suspensions can be prepared from sterile powders, granules, and tablets of the kind previously described.

The dose administered to a patient ("a therapeutically effective amount"), in the context of the present invention should be sufficient to effect a beneficial therapeutic response in the patient over time. The dose will be determined by the efficacy of the particular compound employed and the condition of the patient, as well as the body weight or surface area of the patient to be treated. The size of the dose also will be determined by the existence, nature, and extent of any adverse side-effects that accompany the administration of a particular compound in a particular patient In determining the effective amount of the compound(s) to be administered in the treatment of a disease such as a viral infection or cancer, the physician evaluates circulating plasma levels of the respective compound(s), progression of the disease, and the production of anti-compound antibodies. In general, the dose equivalent of a compound is from about 1 ng/kg to 10 mg/kg for a typical patient.

Proteins of the present invention can be administered at a rate determined by the $LD_{50}$ of the particular compound, and its side-effects at various concentrations, as applied to the mass and overall health of the patient. Administration can be accomplished via single or divided doses.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

The Examples disclosed herein describe the construction and analysis of rationally designed viral-protease activated chimeric toxins, also denoted herein as "zymoxins" for "zymogenized toxins".

The following Materials and Methods were used in the Examples disclosed herein.

Bacterial Strains

The following *Escherichia coli* strains were used: XL-1 Blue (Stratagene, USA) for plasmid propagation and Rosetta (DE-3) (Novagen, USA) for expression of the T7 promoter-driven recombinant toxins.

Recombinant DNA Techniques and Vectors

Recombinant DNA techniques were carried out according to standard protocols or as recommended by suppliers. Nucleotide sequences were determined using the PRISM 3100 Genetic Analyzer (Applied Biosystems, USA) according to the supplier's recommendations. The bacterial T7 promoter-based expression vector pET28a, used for expression of recombinant toxins in *Escherichia coli*, was from Novagen (USA). The eukaryotic tetracycline-inducible CMV promoter-based expression vector pcDNA 4/TO, used for expression of EGFP-scNS3 and EGFP-full NS3-4A in T-REx 293 Cell Line was from Invitrogen (USA). All plasmid and DNA fragment purifications were carried out with HiYield Plasmid Mini Kit and HiYield Gel/PCR DNA Extraction Kit (RBC bioscience, Taiwan). T4 DNA ligase and restriction enzymes were purchased from New England Biolabs (USA). DNA ligations were carried out at 16° C. overnight.

Genomic DNA extraction from *Ricinus communis* was performed as described in (Edwards et al., 1991)

Construction of Expression Vectors
(i) Tetracycline-Inducible Vector Encoding the Cytosolic EGFP-scNS3.

The previously described NS4A-NS3 (single-chain NS3; scNS3) (Dimasi et al., 1998; Taremi et al., 1998; Berdichevsky et al., 2003; Gal-Tanamy et al., 2005) coding sequence was amplified by PCR using the plasmid pMGT14 (Gal-Tanamy et al., 2005) DNA as template, and the following primers:

Forward:
(SEQ ID NO: 83)
5'-TCGAGCTCAAGCTTCGCCACCATGGCGCCTATCGGCTCAGTAG-3'

Reverse:
(SEQ ID NO: 84)
5'-TGGATCCCGGGCCCTCTAGACTCGAGCGGCCGCCACTG-3'.

The PCR product was digested with HindIII and ApaI (restriction sites are underlined in the primer sequences) and was cloned between the corresponding sites in pEGFP-C2 (Clontech, USA), generating plasmid pEGFP-C2-scNS3". Next, a fragment containing the coding sequence of the EGFP-scNS3 fusion was excised from the above plasmid by digestion with Eco47III and ApaI and was cloned between the corresponding sites in the Tetracycline inducible vector pcDNA4/TO, generating plasmid pcDNA4/TO EGFP-scNS3.

(ii) Tetracycline-Inducible Vector Encoding the Membrane Bound EGFP-Full NS3-4A.

The coding sequence of the full length NS3 (including the helicase domain) followed by NS4A from 1a HCV genotype was excised from the plasmid NS3/4A-pVAX1 (Frelin et al., 2003), by digestion with NarI and ApaI. The DNA fragment was then cloned between the corresponding sites in pcDNA4/TO EGFP-scNS3 (replacing the scNS3 sequence), generating plasmid "pcDNA 4/TO EGFP-Full NS3-4A".

Figure 2A:
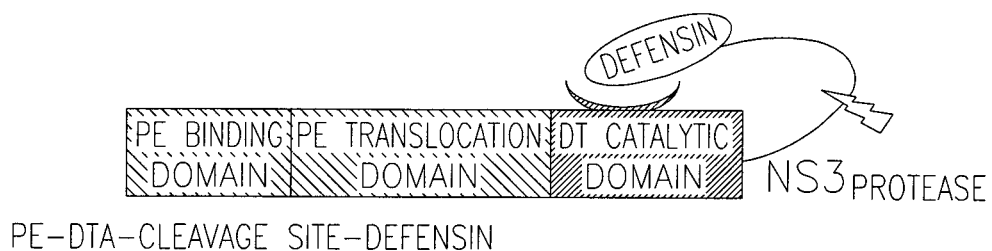
FIGS. 2A and 2C show schematic representations of the toxins "PE-DTA-cleavage site-defensin" and "PE-DTA-mutated cleavage site-defensin", respectively.

(iii) Plasmid PE-DTA-Cleavage Site-Defensin (Shown Schematically in FIG. 2A).

The coding sequence of amino acids 1-605 of *Pseudomonas* exotoxin A (PE), including the signal peptide, was amplified by PCR from a plasmid encoding a PE derivative (PE-QQΔ) kindly provided by Dr. Ira Pastan, NCI, NIH, Bethesda, Md., USA, in which lysines 590 and 606 are substituted with glutamine residues and lysine 613 was deleted (Debinski and Pastan, 1994).

In the same amplification process, a DNA sequence encoding the 10 amino acid minimal NS3 cleavage sequence EDV-VCCSMSY (SEQ ID NO:1), also referred to as P6-P4', from HCV NS5A/B site derived from HCV genotype 1b/1a (Steinkuhler et al., 1996) followed by MfeI site, PstI site, 6 histidine residues (6×HIS) and the KDEL ER retrieval signal was introduced to the 3' end of the toxin coding sequence, using the primers:

Forward:
(SEQ ID NO: 85)
5' TTCCCCTCTAGAAATAATTTTGTTTAACTTTAAGAAGGAGATAT

ACCATGAAAAAGACAGCTATCGCGATTG-3'.

Reverse: (in this order, when PCR product of the
forward and the first reverse primer used as a
template for the forward and the second reverse
primer, and so on):
(SEQ ID NO: 86)
5'-TCGAGCAGCACACGACATCCTCCGCTAGCTCCTGCGCGGCCGCT

CCTTGCCCGGGCTGGCTGGCGTAGTC-3'.

(SEQ ID NO: 87)
5'-CGTCCTTGTGATGGTGATGGTGATGCTGCAGGCCAATTGCGTAG

GACATCGAGCAGCACACGACATCCTC-3'.
and (SEQ ID NO: 88)
5'-ACGGAGCTC<u>GAATTC</u>TTACAGCTCGTCCTTGTGATGGTGATGG-3'.

The final PCR product was digested with XbaI and EcoRI and was cloned between the corresponding sites in the bacterial expression plasmid pET28a, generating the plasmid "pET28a PE QQ delta NS5AB-HIS-KDEL". Next, the human alpha-defensin 1 (HNP 1) coding sequence, preceded by a flexible GS-rich linker of 15 amino acids (GGGGSGGGSGSGGSG) and followed by a linker of 4 amino acids (GSGS), was inserted between the NS5AB and the 6×HIS of the above plasmid. This insert was created by PCR using DNA of the plasmid "pET28a PE QQ delta NS5AB-HIS-KDEL" DNA as template, the reverse primer:

(SEQ ID NO: 89)
5'-CTCAGCTTCCTTTCGGGCTTT-3', and the forward primers: (in this order, when PCR product of the reverse and the first forward primer used as a template for the reverse and the second forward primer, and so on):

(SEQ ID NO: 90)
5'-GGCCGCCTGTGGGCATTCTGCTGTGGTTCTGGTTCCCATCACCA

TCACCATCACAAGGACGAG-3', (SEQ ID NO: 91)
5'-TGCATCGCGGGTGAACGTCGTTACGGCACTTGTATTTATCAAGG

CCGCCTGTGGGCATTCTG-3', (SEQ ID NO: 92)
5'-CGGTAGCGGCGGCTCCGGTGCGTGCTACTGTCGTATTCCGGCTT

GCATCGCGGGTGAACGTCG-3'
and (SEQ ID NO: 93)
5'-ATTGGCCTGCAGGGCGGTGGCGGTTCTGGCGGCGGCTCCGGTAG

CGGCGGCTCCGG-3'

The PCR product was digested with PstI and EcoRI and was cloned between the corresponding sites in the plasmid "pET28a PE QQ delta NS5AB-HIS-KDEL", generating the plasmid "pET28a PE QQ delta NS5AB-15aa linker-HPNI-HIS-KDEL". In the next step, a DNA fragment encoding diphtheria toxin A (kindly provided by Prof. Nadir Arber, Integrated Cancer Prevention Center, Tel Aviv Sourasky Medical Center, Israel) was used as a template for PCR amplification of the region encoding amino acids 1-187 of the mature toxic A domain (without the signal peptide). In the same amplification process, a DNA sequence encoding the 1b derived P6-P4' NS5A/B junction was introduced to the 3' end of the toxin coding sequence.

The primers that have been used:
Forward:
(SEQ ID NO: 94)
5'-AAATTTGACGTCGGCACCGGTGGCGCTGATGATGTTGTTGATT CTTC-3'
and reverse:
(SEQ ID NO: 95)
5'-AAATTTCAATTGCGTAGGACATCGAGCAGCACACGACATCCTC

TGCACAGGCTTGAGCCATATACTCATAC-3'.

The PCR product was digested with restriction enzymes AatII and MfeI and was cloned between the corresponding sites in the plasmid "pET28a PE QQ delta NS5AB-15aa linker-HPNI-HIS-KDEL", generating the plasmid "pET28a PE QQ delta-DTA(1-187)(instead domain III)-NS5AB-15aa linker-HNP-HIS-KDEL" in which the catalytic domain of PE (domain III) was replaced by amino acids 1-187 of DTA, followed by the NS3 cleavable NS5A/B junction sequence, a flexible linker of 15 amino acids rich in glycine and serine, the human alpha-defensin 1 (HNP 1) coding sequence (encoding ACYCRIPACIAGERRYGTCIYQGRLWAFCC), a short 4 amino acid linker, 6×HIS and the KDEL retrieval signal.

Figure 2B:
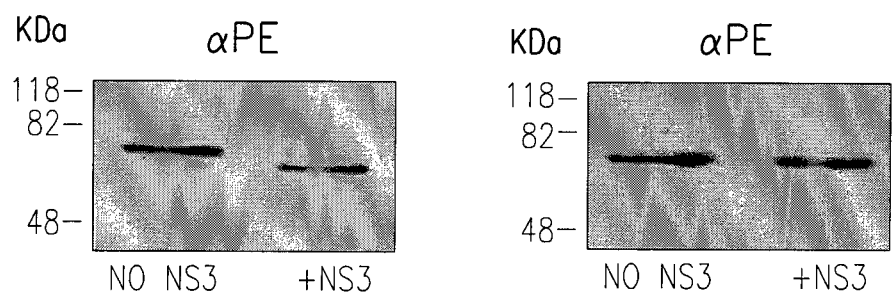
FIG. 2B shows in vitro cleavage by NS3. Each toxin (600 ng) was incubated with or without 500 ng of recombinant MBP-scNS3 fusion in a total volume of 60 µl for 1 hour at 37
Figure 2C:
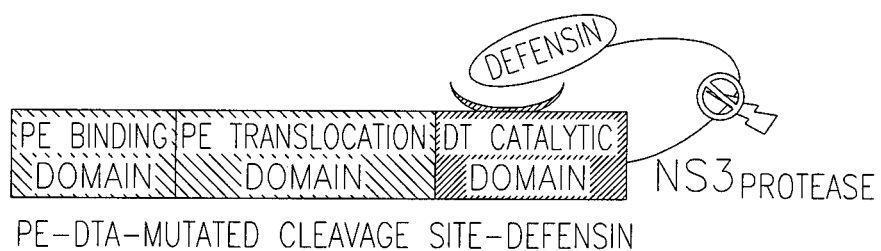

(Iv) Plasmid "PE-DTA-Mutated Cleavage Site-Defensin" (Shown Schematically in FIG. 2C).

The minimal NS3 cleavage sequence (P6-P4') derived from NS5A/B junction of HCV 1b/1a genotype in the plasmid "pET28a PE QQ delta-DTA(1-187)(instead domain III)-NS5AB-15aa linker-HNP-HIS-KDEL" was mutated by substituting P1 cysteine to arginine and P4' tyrosine to alanine using the DNA of plasmid "pET28a PE QQDTA(1-187)(instead domain III) 15aa linker-HNP-NS5AB-HIS-KDEL" as template with the following primers:

Forward:
(SEQ ID NO: 96)
5'-AAATTTGACGTCGGCACCGGTGGCGCTGATGATGTTGTTGATTCTT

C-3'
and reverse primers (in this order, when PCR
product of the forward and the first reverse
primer used as a template for the forward
and the second reverse primer):
(SEQ ID NO: 97)
5'-TTGCCGCGGACATCGAGCGGCACACGACATCCTCTGCAC-3'
and (SEQ ID NO: 98)
5'-ACCGCCCTGCAGGCCAATTGCCGCGGACATCGAGCG-3'.

The PCR product was digested with AatII and PstI and was cloned between the corresponding sites in the plasmid "pET28a PE QQ-DTa(1-187)(instead domain III) 15aa linker-HNP-NS5AB-HIS-KDEL" generating the plasmid "pET28a PE QQ delta-DTA(1-187)(instead domain III)-mutated NS5AB-15aa linker-HNP-HIS-KDEL".

(v) Plasmid "pET28a PE QQ delta-DTA(1-187)(Instead Domain III) 15aa Linker-HNP-HIS-KDEL (Uncleavable)".

For construction of the vector encoding the control DTA based uncleavable toxin, in which the whole NS3 cleavage site was deleted, a PCR was performed using DNA of the plasmid "pET28a PE QQ delta-DTA(1-187)(instead domain III) 15aa linker-HNP-NS5AB-HIS-KDEL" as template, the forward primer:

(SEQ ID NO: 99)
5'-AAATTTGACGTCGGCACCGGTGGCGCTGATGATGTTGTTGATTCTT
C-3' and the reverse primer:

(SEQ ID NO: 100)
5'-ACCGCCCTGCAGGCCAATTGCTGCACAGGCTTGAGCCATATA
C-3'.

The PCR product was digested with PstI and AatII and was cloned between the corresponding sites in the same plasmid that has been used as a template, generating the plasmid "pET28a PE QQ delta-DTA(1-187)(instead domain III) 15aa linker-HNP-HIS-KDEL (uncleavable)"

(vi) Plasmid "PE-DTA-Cleavage Site-Defensin".

For construction of the vector encoding "PE-DTA-cleavage site-defensin" in which the P6-P4' NS3 cleavage sequence derived from 1b genotype NS5A/B junction was replaced by the P10-P10' cleavage sequence derived from 2a genotype NS5A/B junction, a PCR was performed using the DNA of plasmid "pET28a PE QQ delta-DTA(1-187)(instead domain III) 15aa linker-HNP-NS5AB-HIS-KDEL" as template, using the reverse primer:

5'- CTCAGCTTCCTTTCGGGCTTT -3'. (SEQ ID NO: 101)

and the forward primers (in this order, when PCR product of the reverse and the first forward primer used as a template for the reverse and the second forward primer, and so on):

(SEQ ID NO: 102)
5'-
GACCGTATGTTGCTCTATGAGCTACTCCTGGACTGGTGCGCTGGCAATTG
GCCTGCAGGGCGGTG-3'.
and (SEQ ID NO: 103)
5'-
TATATGGCTCAGGCCTGTGCATCTGAAGAAGATGACACGACCGTATGTTG
CTCTATGAGC -3'.

The PCR product was digested with StuI and XhoI and was cloned between the corresponding sites in a plasmid similar to the one used as a template, in which the StuI site was introduced silently (without changing the protein sequence) upstream to the 1b derived NS5A/B sequence, generating plasmid "pET28a PE QQ delta-DTA(1-187)(instead domain III)-full 2a NS5AB-15aa linker-HNP-HIS-KDEL".

(vii) Plasmid "PE-RTA-Cleavage Site-Stalk Peptide" (Shown Schematically in FIG. 4A).

For construction of the vector encoding the RTA based cleavable zymoxin "PE-RTA-cleavage site-stalk peptide", the coding sequence of the catalytic domain, ricin toxin A chain (amino acids 1-267) was amplified from a *Ricinus communis* genomic DNA preparation by PCR using the forward primer:

(SEQ ID NO: 104)
5'-AAATTTCCGCGGCATATTCCCCAAACAATACCC-3', and the reverse primer:

(SEQ ID NO: 105)
5'-AAATTTCAATTGCAAACTGTGACGATGGTGGAGG-3'.

The PCR product was digested with SacII and MfeI and was cloned between the corresponding sites of plasmid "pET28a PE QQ delta NS5AB-HIS-KDEL", generating the plasmid "pET28a PE QQ (I-II-Ib-RTA)-HIS-KDEL", which served as a template for another PCR using the forward primer:

(SEQ ID NO: 106)
5'-AAATTTCCGCGGCATATTCCCCAAACAATACCC-3' and the reverse primers (in this order, when PCR product of the forward and the first reverse primer used as a template for the forward and the second reverse primer, and so on):

(SEQ ID NO: 107)
5'-
CGTACGACATGCTACAACACACCACATCTTCGGATCCTGACGATGGTGGA
GGTGCGC-3', (SEQ ID NO: 108)
5'-
CATGTCATCATCGGATTCTTCGGATTCCTCTGAGCCGCCACCGCCGTACG
ACATGCTACAACACA-3', (SEQ ID NO: 129)
5'-
GTCGGATTCCTCGGACTCCTCACCACCGGTGTCGAACAGACCAAAACCCA
TGTCATCATCGGATTCTTC -3'
and (SEQ ID NO: 130)
5'-
GTGATGCTGCAGAGAACCGGTGTCAAACAGGCCGAAGCCCATATCGTCGT
CGGATTCCTCGGACTCCTC -3'.

The PCR product was digested with SacII and PstI, and was cloned between the corresponding sites in the same plasmid that has been used as a template, generating plasmid "pET28a PE QQ delta RTA-short linker-stalk peptide-HIS-KDEL" in which two repeats of the acidic 16 residue peptide corresponding to the conserved C terminus of the ribosomal stalk proteins (EESEESDDDMGFGLFD) have been fused to the C-terminus of RTA, preceded by the P6-P4' NS3 cleavable NS5A/B junction sequence derived from 1b/1a genotype, a short linker of Gly-Gly-Gly-Gly-Ser and followed by 6×HIS and the KDEL ER retrieval signal.

(viii) Plasmid "PE-RTA-Mutated Cleavage Site-Stalk Peptide" (Shown Schematically in FIG. 4B).

For construction of the vector encoding the uncleavable control zymoxin "PE-RTA-mutated cleavage site-stalk peptide", the minimal NS3 cleavage sequence (P6-P4') derived from NS5A/B junction of HCV 1b/1a genotype in the plasmid "pET28a PE QQ delta RTA-short linker-stalk peptide-HIS-KDEL" was mutated by substituting P1 cysteine to arginine and P4' tyrosine to alanine using the following primers with the DNA of plasmid "pET28a PE QQ delta RTA-short linker-stalk peptide-HIS-KDEL" as template:

Forward:
(SEQ ID NO: 109)
5'-TCGTCAGGATCCGAGGATGTCGTGTGCCGCTCGATGTCCGCGGGCGGTGGCGGCTCAGAGGAATC-3'

Reverse:
(SEQ ID NO: 110)
5'-ACGGAGCTCGAATTCTTACAGCTCGTCCTTGTGATGGTGATGG-3'.

The PCR product was digested with BamHI and EcoRI, and was cloned between the corresponding sites in the same plasmid that has been used as a template, generating the plasmid "pET28a PE QQ delta RTA-mutated NS5AB-short linker-stalk peptide-HIS-KDEL".

(ix) Plasmid "PE-RTA-Cleavage Site-Stalk Peptide".

For construction of the vector encoding "PE-RTA-cleavage site-stalk peptide" zymoxin in which the P6-P4' NS3 cleavage sequence derived from 1b genotype NS5A/B junction was replaced by the P10-P10' cleavage sequence derived from 2a genotype NS5A/B junction, a PCR was performed using the DNA of plasmid "pET28a PE QQ delta RTA-short linker-stalk peptide-HIS-KDEL" as template, the reverse primer:

```
                                        (SEQ ID NO: 111)
5'-CTCAGCTTCCTTTCGGGCTTT -3'
``` and the forward primers (in this order, when PCR product of the reverse and the first forward primer used as a template for the reverse and the second forward primer, and so on):

```
                                        (SEQ ID NO: 112)
5'-
TATGTTGCTCTATGAGCTACTCCTGGACTGGTGCGCTGGGCGGTGGCGGC
TCAGAGG -3'
                                        (SEQ ID NO: 113)
5'-
CCATCGTCAGGATCCGAAGAAGATGACACGACCGTATGTTGCTCTATGAG
CTACTCC -3'.
```

The PCR product was digested with BamHI and XhoI and was cloned between the corresponding sites in the same plasmid that has been used as a template, generating the plasmid "pET28a PE QQ delta RTA-full 2a NS5AB-short linker-stalk peptide-HIS-KDEL".

(x) Plasmid "MBP-EGFP-NS5AB-CBD".

For construction of the vector encoding the NS3 cleavable substrate "MBP-EGFP-NS5AB-CBD" bearing the P6-P4' NS3 cleavage sequence derived from 1b/1a genotype NS5A/B junction (shown schematically in FIG. 1D), the EGFP-NS5A/B-CBD coding sequence was excised from the plasmid "pYB-44" (Berdichevsky et al., 2003) by digestion with NcoI and BamHI, and ligated into the corresponding sites in the plasmid "pCMV/H6myc/Cyto-MBP" (Shaki-Loewenstein et al., 2005), generating plasmid "pCMV/MBP-EGFP-NS5AB-CBD".

(xi) Plasmid "MBP-EGFP-Full 1b NS5AB-CBD".

For construction of the vector encoding the NS3 cleavable substrate "MBP-EGFP-full 1b NS5AB-CBD" bearing the P10-P8' NS3 cleavage sequence derived from 1b genotype NS5A/B junction, a PCR was performed using the DNA of plasmid "pCMV/MBP-EGFP-NS5AB-CBD" as template, the reverse primer: 5'-TAGAAGGCACAGTCGAGG-3' (SEQ ID NO:114) and the forward primers (in this order, when PCR product of the reverse and the first forward primer used as a template for the reverse and the second forward primer, and so on):

```
                                        (SEQ ID NO: 115)
5'-
AAGACGTAGTATGTTGCTCTATGAGTTACACTTGGACCGGGACACCGGTA
TCAGGCAATTTGAAG-3'
and
                                        (SEQ ID NO: 116)
5'-
CTACAAGGACGCTAGCGGTGCTGACACAGAAGACGTAGTATGTTGCTCTA
TG -3'
```

The PCR product was digested with NheI and HindIII and was cloned between the corresponding sites in the same plasmid that has been used as a template, generating plasmid "pCMV/MBP-EGFP-full 1b NS5AB-CBD".

(xii) Plasmid "MBP-EGFP-Full 2a NS5AB-CBD".

For construction of the vector encoding the NS3 cleavable substrate "MBP-EGFP-full 2a NS5AB-CBD" bearing the P10-P10' NS3 cleavage sequence derived from 2a genotype NS5A/B junction, a PCR was performed using the DNA of plasmid "pCMV/MBP-EGFP-NS5AB-CBD" as template, the reverse primer: 5'-TAGAAGGCACAGTCGAGG-3' and the forward primers (in this order, when PCR product of the reverse and the first forward primer used as a template for the reverse and the second forward primer, and so on):

```
                                        (SEQ ID NO: 117)
5'-
TGACACGACCGTATGTTGCTCTATGAGCTACTCCTGGACTGGTGCGCTGA
CACCGGTATCAGGCAATTTG-3'
and
                                        (SEQ ID NO: 118)
5'-ACAAGGACGCTAGCTCTGAAGAAGATGACACGACCGTATGTTGCTC-
3'.
```

The PCR product was digested with NheI and HindIII and cloned between the corresponding sites in the same plasmid that has been used as a template, generating plasmid "pCMV/MBP-EGFP-full 2a NS5AB-CBD".

Protein Expression and Purification

*E. coli* BL21 Rosetta (DE3) cells were transformed with pET28a based expression plasmids and grown in 1 liter of LB medium supplemented with 50 μg/ml Kanamycin, at 37° C. 250 rpm shaking to O.D. 600 nm of 0.8. The cells were chilled down to 30° C. and induced with 1 mM IPTG for 3-4 hours at 30° C., 250 rpm. The cells were collected by centrifugation at 5000 g, 4° C. 10 minutes. For preparation of periplasmic fractions, the cell pellet was gently re-suspended in 200 ml of ice-cold 20% sucrose, 30 mM Tris(HCl) (pH 7.4), 1 mM EDTA, using glass beads. The cell suspension was incubated on ice for 15 minutes and centrifuged at 6000 g, 4° C. 15 minutes. The cell pellet was gently re-suspended in 200 ml of ice cold sterile double distilled water (DDW), incubated on ice for 15 minutes and centrifuged at 8000 g, 4° C. 20 minutes. The supernatant periplasmic fraction was adjusted to 20 mM Tris-HCl (pH 8.0), 300 mM NaCl and 5 mM Imidazole. The periplasmic fraction was incubated over-night, in continues rotation with 700 µl of Ni-NTA resin (Favorgen, Taiwan) that was previously equilibrated with Binding buffer (20 mM Tris-HCl pH 8.0, 300 mM NaCl). Ni-NTA resin was then separated from the periplasmic supernatant by 5 minutes centrifugation at 70 g, 4° C., loaded on Poly Prep column (Bio-Rad, USA) and washed with 20 ml of binding buffer+5 mM imidazole. Bound His-tagged protein was subsequently eluted with 700 µl PBS containing 500 mM imidazole, and dialyzed twice against 1 liter of PBS.

Cell Culture, Transfection, Protein Extraction and Immunoblotting

Human embryonic kidney cells HEK293, stably expressing the tetracycline repressor protein (T-REx 293 Cell Line, Invitrogen, USA), and human hepatoma cells Huh7.5 (Blight et al., 2002) were used throughout this study. Cell lines were maintained in DMEM supplemented with 10% fetal calf serum (FCS), 2 mM 1-glutamine, 100 U/ml penicillin, 100 µg/ml streptomycin and 12.5 U/ml nystatin (Biological Industries, Israel) in a humidified 5% $CO_2$ incubator at 37° C. The calcium-phosphate transfection method was applied for introducing 2 µg of the plasmids "pcDNA 4/TO EGFP-scNS3", "pcDNA 4-TO EGFP-Full NS3-4A" or "pCMV/MBP-EGFP-NS5AB-CBD" into T-Rex 293 cells, seeded $1.5 \times 10^6$ cells per 6 cm plate 24 hours before transfection. Stable transfectants, inducibly expressing EGFP-scNS3 or EGFP-Full NS3-4A were selected in a medium containing zeocin (200 µg/ml) (CAYLA, France).

2 µg of the plasmids "pCMV MBP-EGFP-full 1b NS5AB-CBD" or "pCMV MBP-EGFP-full 2a NS5AB-CBD" were introduced into uninfected or HCV infected Huh7.5 Cells (seeded $3 \times 10^5$ cells per well in 6-well plate 24 hours before transfection) using FuGENE 6 reagent (Roche, Germany), according to the manufacturer instructions.

For protein extraction, 48 hours post-transfection the cells were washed with PBS, scraped and lysed in a buffer containing 150 mM NaCl, 5 mM EDTA, 0.5% NP-40, 10 mM Tris(HCl) pH 7.5, and protease inhibitors cocktail (Sigma, Israel). Following 30 minutes of incubation on ice, lysates were cleared by centrifugation at 20,000 g for 10 minutes, at 4° C. For immunoblotting, protein samples were electrophoresed on 12% SDS/polyacrylamide gel, transferred to nitrocellulose and detected using rabbit polyclonal anti-GFP antibody (Santa-Cruz, USA) or polyclonal mouse serum anti-MBP followed by HRP-conjugated goat anti-rabbit or anti-mouse mouse antibodies (Jackson ImmunoResearch Laboratories, USA) and ECL detection. immunoblotting of purified recombinant toxins was similarly performed, using rabbit polyclonal anti-PE antibody, kindly provided by Dr. Ira Pastan, NCI, NIH, Bethesda, Md., USA.

Viral Infection.

Virus assays were carried out with an inter-genotypic chimeric virus produced by replacing the core-NS2 segment of the JFH-1 virus genome with the comparable segment of the genotype 1a H77 virus. This chimeric virus, HJ3-5, contains two compensatory mutations that promote its growth in cell culture as described previously (Yi et al., 2007; McGivern et al., 2009). HCV RNAs were transcribed in vitro and electroporated into cells essentially as described previously (Yi and Lemon, 2004; Yi et al., 2006). In brief, 10 µg of in vitro-synthesized HCV RNA was mixed with $5 \times 10^6$ Huh7.5 cells in a 2-mm cuvette and pulsed twice at 1.4 kV and 25 µF. Cells were seeded into 12-well plates or 25-cm² flasks, and passaged at 3- to 4-day intervals posttransfection by trypsinization and reseeding with a 1:3 to 1:4 split into fresh culture vessels. When infectivity reached >95%, as was monitored by immunofluorescent staining with anti HCV core protein, Cells were taken for cytotoxicity or substrate cleavage assays.

Immunofluorescence Microscopy.

$1 \times 10^5$ T-REx 293 cells inducibly expressing EGFP-scNS3 or EGFP-full NS3-4A were seeded on poly-L-lysine coated cover-slips in a 24 well-plate. After 12 hours, the cells were treated with 1 mg/ml of tetracycline for 24 hours (or remained untreated), washed with PBS, fixed with 4% paraformaldehyde in PBS at room temperature for 20 minutes, permeabilized with Triton X-100 (0.1% in PBS) for 5 minutes, and blocked with 90% fetal calf serum/10% PBS at room temperature for 25 minutes. Slides were incubated with 1:200 diluted rabbit-polyclonal anti-calnexin antibody (Sigma, USA) as primary antibody for 1 hour, and followed by 1:500 diluted Cy3-conjugated anti-rabbit IgG (Jackson ImmunoResearch Laboratories, USA) secondary antibody and Hoechst 33258 (5 µg/ml) (Sigma, USA) for 1 hour at room temperature. Slides were washed with PBS, mounted in ImmuGlo Mounting Medium (IMMCO Diagnostics, USA), and examined with a Zeiss LSM 510 META laser scanning confocal microscope.

HUH7.5 cells infected with HCV HJ3-5 chimeric virus were seeded into 8-well chamber slides (Nalge Nunc, USA). After 24 hours, cells were fixed and permeabilized as described above and stained with 1:300 diluted mouse monoclonal antibody C7-50 (Affinity BioReagents, USA) specific for the HCV core protein followed by staining with 1:100 diluted Cy2-conjugated goat anti-mouse IgG (Jackson ImmunoResearch Laboratories, USA). Slides were mounted and examined using a fluorescence microscope.

In Vitro Cleavage of DTA and RTA Based Toxins.

600 ng of DTA based toxins or 3000 ng of RTA based toxins were incubated with or without 500 ng or 1000 ng, respectively, of recombinant MBP-scNS3 fusion (Gal-Tanamy et al., 2005) in a reaction buffer (50 mM Tris-HCl (pH 7.5), 150 mM NaCl, 0.05% tween 20, 20% glycerol and 1.7 mM of DTT) in a total volume of 60 µl for 1 hour at 37° C. NS3 mediated cleavage was verified by western blotting of 50 ng (DTA based toxins) or 250 ng (RTA based toxins) toxin samples using rabbit polyclonal anti-PE antibody.

ADP-Ribosylation Assay

ADP-ribosylation activity of DTA based toxins was determined by measuring transfer of ADP-ribose from [$^{14}$C]NAD to EF-2 essentially as described at (Mansfield et al., 1996). Shortly, 30 ng of each toxin were diluted to 210 µL in 50 mM Tris-HCl (pH 8.0), 1 mM EDTA, and 0.1% BSA. Mixture was incubated with wheat germ extract in the presence of 2.4 µM [$^{14}$C] NAD ($6 \times 10^5$ cpm) (Amersham Biosciences, UK) for 40 minutes at RT. Reactions were terminated by addition of TCA to the reaction mixture which resulted in total protein precipitation. Level of ADP-ribosylated EF2 was assessed by measuring the radioactivity of the precipitated protein by a scintillation counter.

Ribosome Depurination Assay

The catalytic activity of ricin A based toxins was determined by a modification of the in-vitro assay described at (May et al., 1989; Munishkin and Wool, 1995). A serial dilutions of the cleavable or uncleavable RTA based toxins (treated or untreated with NS3) were incubated with 10 µl of micrococcal nuclease-treated rabbit reticulocyte lysate (Promega, USA) for 30 minutes at 30° C., after which total RNA from each mixture was extracted with phenol and chloroform, precipitated in ethanol and suspended in 22 µl of water. Half of the RNA (11 µl) was then treated with 50 µl of acidic aniline (1M aniline in 2.8 M acetic acid) for 10 minutes at 40° C. and the other half remained untreated. Next, RNA was recovered by precipitation with ammonium acetate and ethanol, and analyzed by 3% TBE agarose gel electrophoresis.

Cell-Viability Assay

Cell-killing activities of recombinant toxins of were measured by a MTT assay. For cytotoxicity assay on T-REx 293 cells inducibly expressing NS3 protease, $4\times10^4$ cells were seeded per well in 96-well plates. After 9 hours, cells were treated with 1 µg/ml of tetracycline or left untreated. 2 hours later, cells were incubated with serial dilutions of the toxins (presence of tetracycline was kept in the growth media of induced cells). After 72 hours, the media was replaced by fresh media (100 µl per well) containing 1 mg/ml MTT (Thiazolyl Blue Tetrazoliam Bromide (Sigma, USA) dissolved in PBS) reagent and the cells were incubated for another 30 minutes. MTT-formazan crystals were dissolved by the addition of extraction solution (20% SDS, 50% DMF, pH 4.7) (100 µl per well) and incubation for 16 hours at 37° C. Absorbance at 570 nm was recorded on an automated microtiter plate reader. The results were expressed as percentage of living cells relatively to the untreated controls. The $IC_{50}$ value is the concentration of the toxin which inhibited cell growth by 50%.

For cytotoxicity assay on HCV infected or uninfected HUH7.5 cells, $1\times10^4$ Huh7.5 cells uninfected or infected with HJ3-5 chimeric virus were seeded per well in 96-well plates. After 24 hours, cells were incubated with serial dilutions of the toxins. 96 hours later, the media was replaced by fresh media (100 µl per well) containing 1 mg/ml MTT and the cells were incubated for another 60 minutes. Further steps were identical to theses described above.

Example 1

Establishment of NS3 Protease Expressing Model Cell System

For the purpose of establishing a model cell line expressing the HCV NS3 protease, we constructed a fusion protein between the previously described single chain construct NS4A-NS3 (single-chain NS3; scNS3) (Gal-Tanamy et al., 2005) in which a short synthetic peptide encompassing residues 21-34 of NS4A (of the 1b HCV genotype) was linked to the N terminus of the NS3 protease domain (Dimasi et al., 1998; Taremi et al., 1998; Berdichevsky et al., 2003), and enhanced green fluorescent protein (EGFP). In addition, another construct was made, comprising a fusion of EGFP and the full length NS3 (protease/RNA helicase) followed by full length NS4A (of the 1a HCV genotype) (Frelin et al., 2003). As opposed to EGFP-scNS3, which is predicted to be a soluble cytoplasmic or nucleocytoplasmic protein; the EGFP-full length NS3 (which strongly interacts with the full length NS4A following auto-cleavage) is expected to be associated with membranes when expressed in mammalian cells, more precisely mimicking the intracellular localization of this complex in HCV infected cells. The is based on the reasoning that the hydrophobic amino terminal domain of the full NS4A directs the NS3-NS4A complex to the ER membrane or an ER-like modified compartment (Wolk et al., 2000; Moradpour et al., 2003; Zemel et al., 2004; Moradpour et al., 2007).

A TET-ON inducible system was established to avoid toxic effects observed upon prolonged over-expression of EGFP-scNS3 and EGFP-full NS3-4A in HEK293 cells. In the TET-ON system, based on T-REx™ 293 cell line (Invitrogen), expression of EGFP-scNS3 or EGFP full NS3-4A (also referred to herein as "scNS3" and "full NS3-4A", respectively) is induced by addition of tetracycline (Tet) to the growth medium.

Figure 1D:
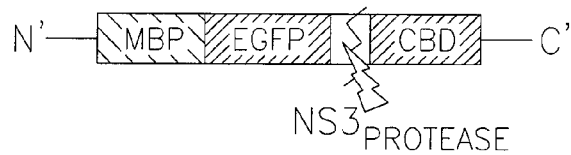
FIG. 1D shows a schematic diagram of the plasmid pCMV/MBP-EGFP-NS5AB-CBD encoding a cleavable substrate.
Figure 1E:
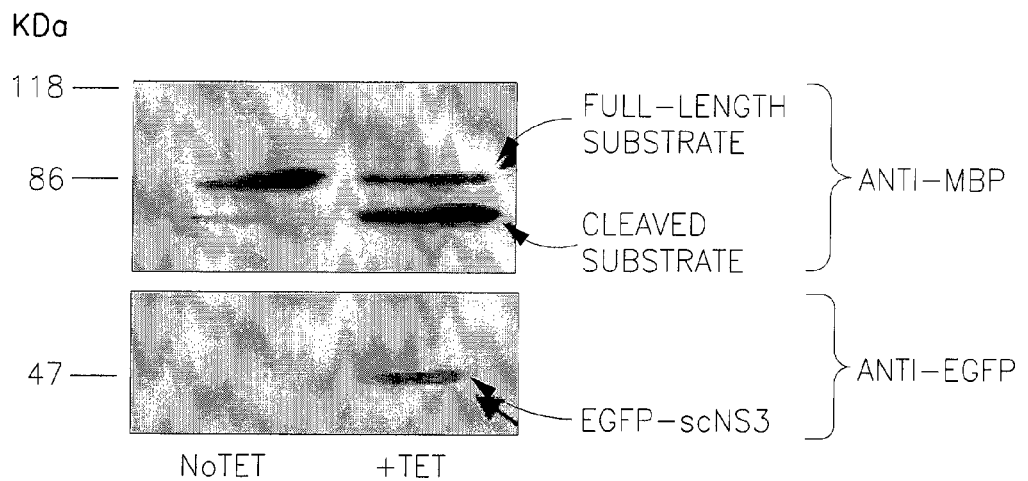
FIG. 1E shows in vivo substrate cleavage by NS3. Cells induced to express EGFP-scNS3 were transfected with 2 µg of the plasmid pCMV/MBP-EGFP-NS5AB-CBD encoding a cleavable substrate (represented in FIG. 1D). After 24 hours, cells were treated with 1 µg/ml of tetracycline (TET) or left untreated. After 24 hours, total cell extract proteins (20 µg) were analyzed by immunoblotting, using either rabbit anti-EGFP antibody or mouse serum anti-MBP antibody, followed by HRP-conjugated secondary antibody and ECL development, for detection of substrate cleavage products. Bands corresponding to the full length substrate, cleaved substrate and EGFP-scNS3 are indicated by arrows.

In order to monitor specific NS3 proteolytic activity in Tet induced cells, we constructed another plasmid coding for a modification of our previously described polypeptide which serves as a substrate for proteolysis by the NS3 protease (Berdichevsky et al., 2003). This plasmid, denoted pCMV/MBP-EGFP-NS5AB-CBD, encodes a fusion protein of maltose binding protein (MBP), enhanced green fluorescence protein (EGFP), the 10 amino acid minimal NS3 cleavage sequence (P6-P4') from HCV NS5A/B site derived from HCV genotype 1b/1a (for both 1b and 1a genotypes this sequence is identical) (Steinkuhler et al., 1996) and cellulose binding domain (CBD). As shown in FIG. 1, addition of Tet to selected stable clones of the inducible system results in EGFP-scNS3 (FIG. 1B) and EGFP-full NS3-4A expression (FIG. 1C), as assayed by fluorescence confocal microscopy and immunoblotting. Regarding the intracellular localization of the proteases, EGFP-full NS3-4A was only partially colocalized with calnexin (ER) in these cells, but apparently was absent from the nucleus and has less diffuse distribution pattern in comparison to the nucleocytoplamic EGFP-scNS3, as was expected. Immunoblot analysis (FIG. 1E) also shows efficient cleavage of MBP-EGFP-NS5AB-CBD (also referred to herein as "cleavable substrate"; schematically represented in FIG. 1D) in cells transfected with pCMV/MBP-EGFP-NS5AB-CBD and induced for NS3 expression.

Example 2

Construction of a Diphtheria Toxin-Based Zymoxin

The toxin-substrate interaction model predicts that an intimate interaction between DTA and its intracellular target elongation factor 2 resides in the C terminal portion of the toxin (Jorgensen et al., 2005). The present inventors have now fused human alpha-defensin 1 (HNP 1) to the C-terminus of DTA, preceded by the 10 amino acid minimal NS3 cleavage sequence (P6-P4') from HCV (genotype 1b/1a) NS5A/B site (referred as “cleavage site”) and a flexible linker of 15 amino acid rich in serine and glycine residues. This construct was then fused in its N-terminus to the binding and translocation domains of *Pseudomonas* exotoxin A (PE) in order to enable internalization and trafficking to the cytosol of mammalian cells, as the natural binding and translocation domains of the diphtheria toxin, which are positioned to the C-terminus of the wild type toxin, were substituted by the HNP1 polypeptide. In addition, a 6×His tag followed by a KDEL ER retrieval signal were placed at the most C terminal portion of the construct (“PE-DTA-cleavage site-defensin”), for facilitating the toxin purification and as the KDEL retrieval system is exploited by PE in order to reach the ER lumen (Jackson et al., 1999), respectively. This 6×His-KDEL extension was positioned at the C-terminus of all the chimeric constructs disclosed herein, which have been expressed in *E. coli* BL21 cells and purified from the periplasmic fraction as described in Materials and Methods. As a control, an uncleavable chimeric toxin was constructed, in which the NS3 cleavage site was mutated by substituting P1 cysteine to arginine and P4' tyrosine to alanine (“PE-DTA-mutated cleavage site-defensin”), represented in FIG. 2C.

Example 3

DTA-Based Zymoxin Enzymatic Activity is Elevated Following NS3 Protease Cleavage In order to evaluate the susceptibility of the constructs described in Example 2 to cleavage by the NS3 protease and to evaluate the influence of such cleavage on their ADP-ribosylation activity, an in vitro cleavage reaction was carried out by incubating the chimeric toxins with recombinant MBP-scNS3 fusion produced in *E. coli* (Gal-Tanamy et al., 2005), followed by an ADP-ribosylation activity assay using wheat germ extract as a source of elongation factor 2 (Collier and Kandel, 1971; Hwang et al., 1987). A schematic representation of the PE-DTA chimeric toxins, the in vitro cleavage products and the ADP-ribosylation assay results are shown in FIG. 2. As shown, incubation of the toxin "PE-DTA-cleavage site-defensin" with the recombinant protease resulted in a complete cleavage of the chimeric toxin that appeared as a lower weight product in immunoblot assay using anti-PE antibodies (FIG. 2B left panel). Moreover, the cleavage led to a considerable increase in the ADP-ribosylation activity of the toxin (FIG. 2D).

Figure 2D:
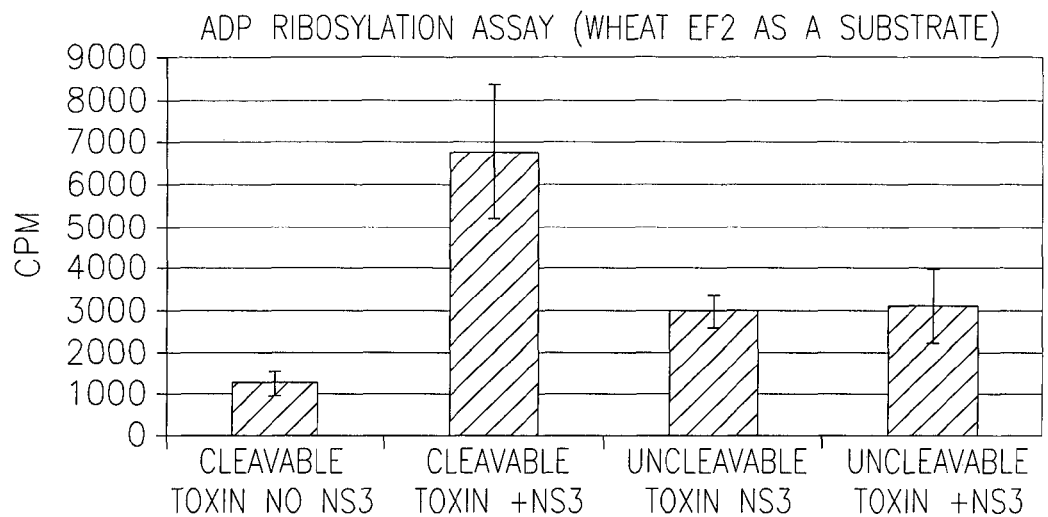
FIG. 2 shows schematic representations of the PE-DTA chimeric toxins and demonstration of in-vitro cleavage by NS3 followed by ADP-ribosylation assay.
Figure 3A:
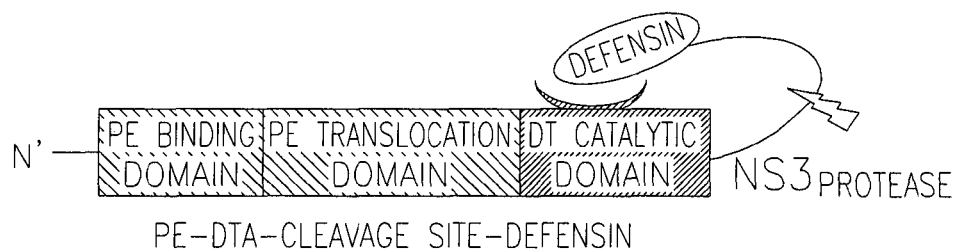
Figure 3B:
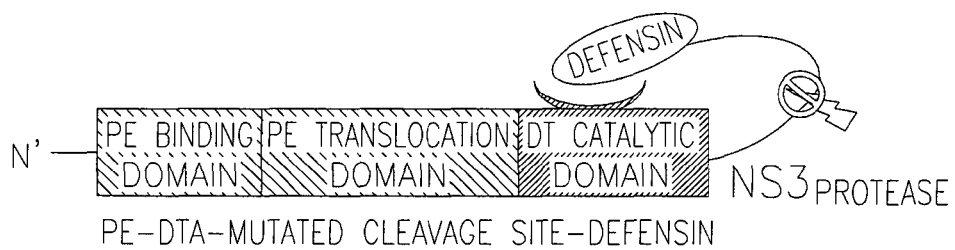
Figure 3C:
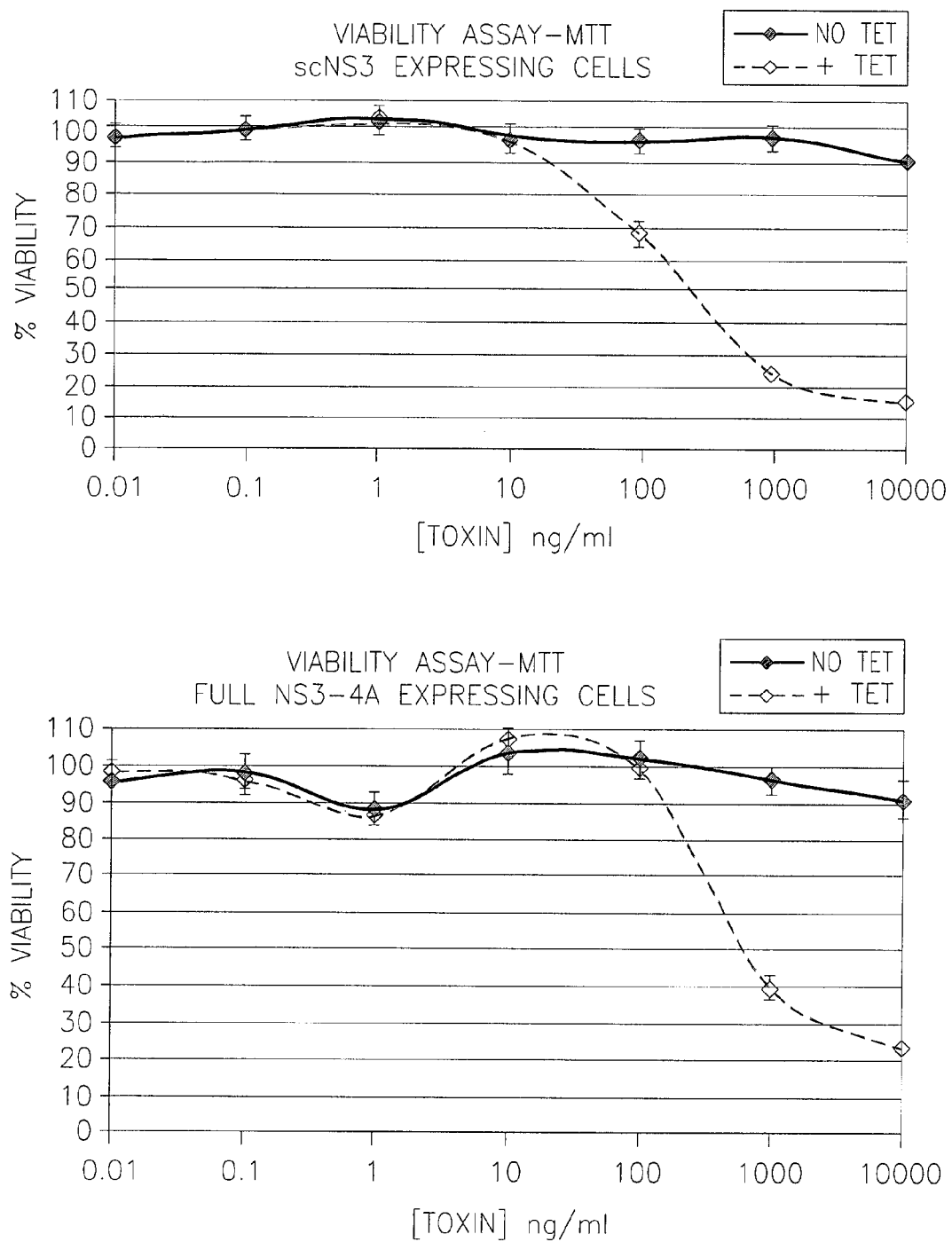
Figure 3C:
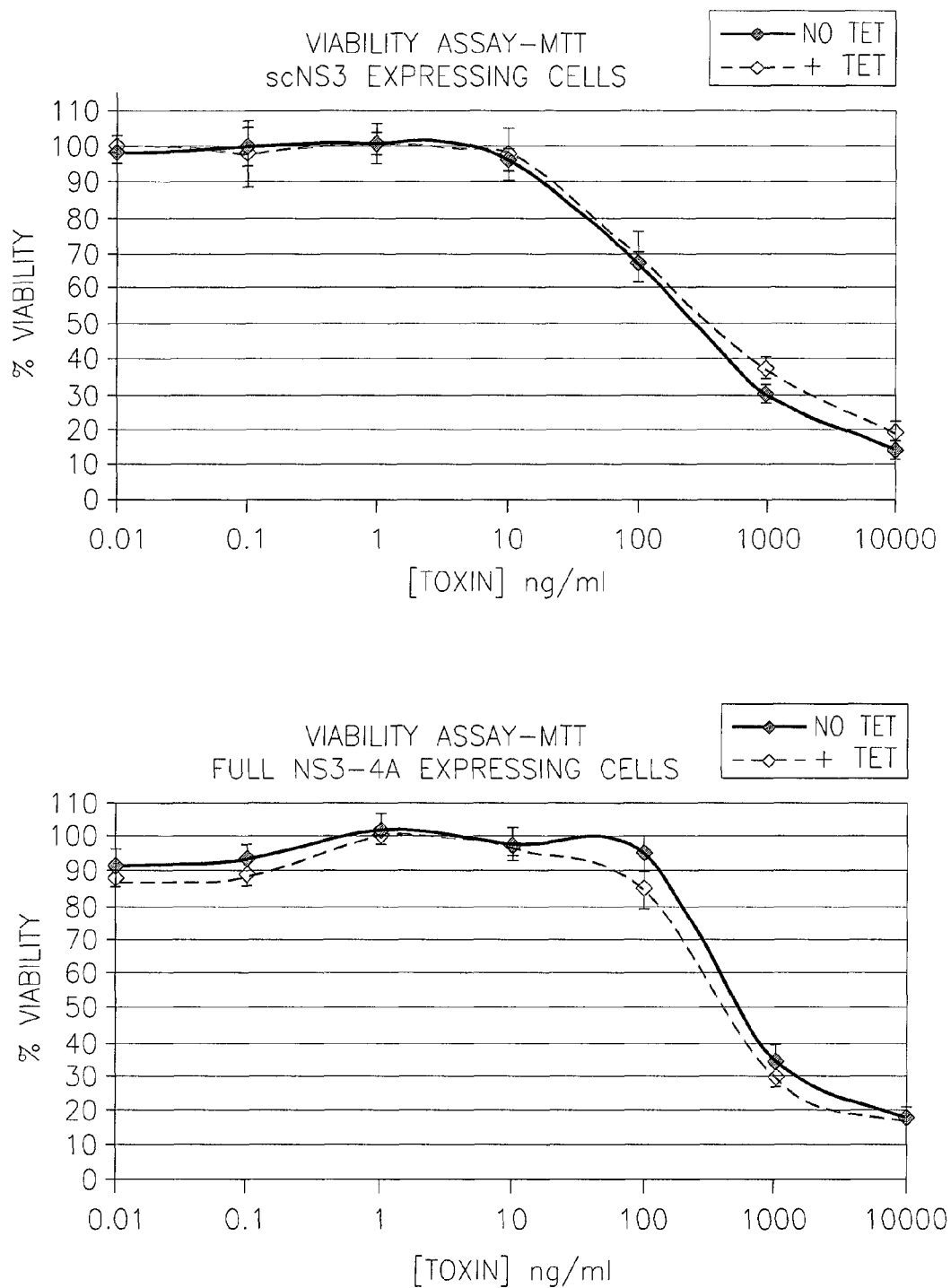

In contrast, the toxin with the mutated cleavage site was resistant to cleavage by NS3 (FIG. 2B right panel), and no significant increase in its ADP-ribosylation activity could be detected after incubation with the protease (FIG. 2D). The observed ADP-ribosylation activity of the uncleavable toxin (higher than the basal activity of the uncleaned-cleavable toxin but lower than the cleaved toxin), may be attributed to facilitation of the interaction with its substrate due to mutation at the NS3 cleavage site.

Example 4

DTA-Based Zymoxin Cytotoxicity is Elevated in NS3 Expressing Cells

In order to evaluate the toxin activation by HCV protease in vivo, our model cell lines, induced or uninduced for NS3 expression, were treated with "PE-DTA-cleavage site-defensin" or "PE-DTA-mutated cleavage site-defensin". As shown in FIG. 3, tetracycline induction for expression of scNS3 and full NS3-4A has led to considerable activation of the cleavable toxin with only a minor cytotoxic effect on uninduced cells. On the contrary, no enhancement in cytotoxic activity of the uncleavable toxin was evident, indicating that induction of NS3 expression does not a cause a general sensitization to DTA based toxins in these cells.

Example 5

Construction of a Ricin Toxin-Based Zymoxin

In order to provide chimeric toxins in which the toxicity of a ricin catalytic domain is "disarmed" prior to enzymatic cleavage of the chimeric protein, the present inventors have engineered a chimeric toxin comprising a fragment derived from the ribosomal stalk protein P1 (or P2) and RTA.

More specifically, we have cloned the coding sequence of the catalytic A chain of ricin (RTA) from a genomic DNA preparation of *Ricinus communis* into a bacterial expression plasmid. Subsequently, we constructed a chimeric toxin in which two repeats of the acidic 16 residue peptide (EESEES-DDDMGFGLFD) corresponding to the conserved C-terminus of the ribosomal stalk proteins were fused to the C-terminus of RTA. Similar to the approach taken for construction of the diphtheria chimeric toxins described herein, the cleavable toxin "PE-RTA-cleavage site-stalk peptide" was prepared, in which the NS3 protease minimal cleavage sequence (P6-P4') from genotype 1b/1a NS5A/B junction was inserted between RTA and the ribosome stalk peptide. In the uncleavable toxin "PE-RTA-mutated cleavage site-stalk peptide", a mutated cleavage site was positioned at the corresponding location. These constructs were then fused in their N-termini to the binding and translocation domain of PE. By fusing RTA to the bacterially derived binding and translocation domains of PE, chimeric PE-RTA toxins that are capable of penetrate into the mammalian cell cytoplasm may be produced in *E. coli* by standard methods.

Example 6

RTA-Based Zymoxin Enzymatic Activity is Elevated Following NS3 Protease Cleavage In order to assess the susceptibility of the constructs described in Example 5 to cleavage by NS3 and evaluate the influence of such cleavage on their ribosome depurination activity, an in vitro cleavage reaction was carried out (as previously described for the diphtheria toxin-based chimera), following by ribosome depurination assay using the acidic aniline method based on reticulocyte lysate derived ribosomes (May et al., 1989; Munishkin and Wool, 1995). In this method, the phosphodiester bond at the 3' site of the depurinated adenine in the ricin treated rRNA is cleaved by treatment with aniline under acidic conditions, and a small fragment of about 460 nucleotides ("R fragment") is released and can be detected by agarose or acrylamide gel electrophoresis and staining with ethidium bromide. A schematic representation of the PE-RTA chimeric toxins, the in vitro cleavage and the ribosome depurination assay results are represented in FIG. 4.

As shown, incubation of the toxin "PE-RTA-cleavage site-stalk peptide" with the recombinant NS3 protease resulted in complete cleavage of the chimeric toxin that appeared as a lower weight product (FIG. 4C upper panel). In contrast, the corresponding uncleavable toxin remained indifferent to the presence of the protease (FIG. 4C lower panel).

Moreover, cleavage of "PE-RTA-cleavage site-stalk peptide" led to an increase in ribosome depurination activity of the toxin, as indicated by the appearance of the "R fragment" (FIG. 4D left panel). This fragment was undetectable when ribosomes were treated with the same concentration of non-cleaved cleavable toxin (cleavable toxin without incubation with NS3; FIG. 4D left panel), or with the uncleavable toxin (FIG. 4D right panel).

Example 7

RTA-Based Zymoxin Cytotoxicity is Elevated in NS3 Expressing Cells

Figure 5C:
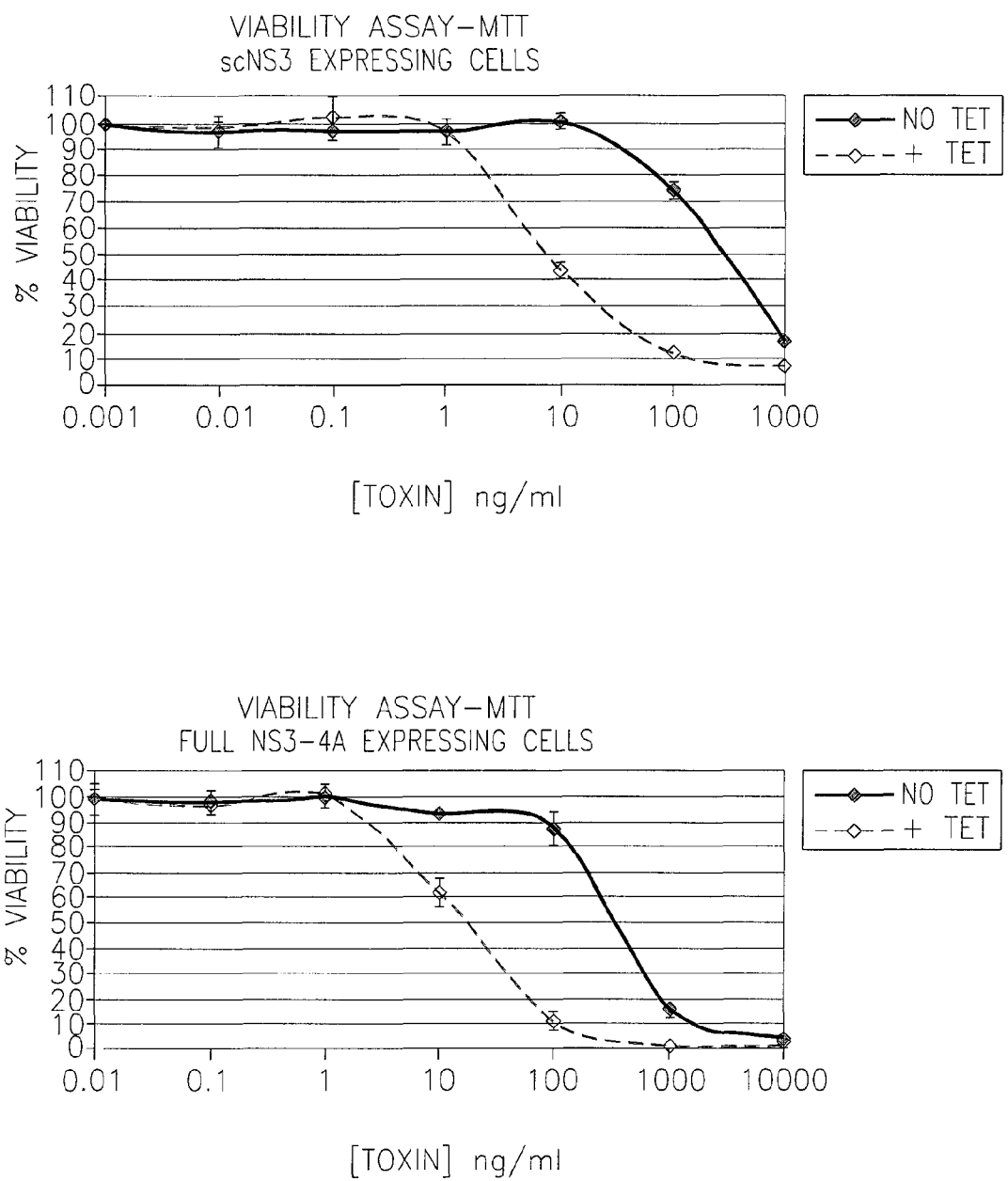
Figure 5C:
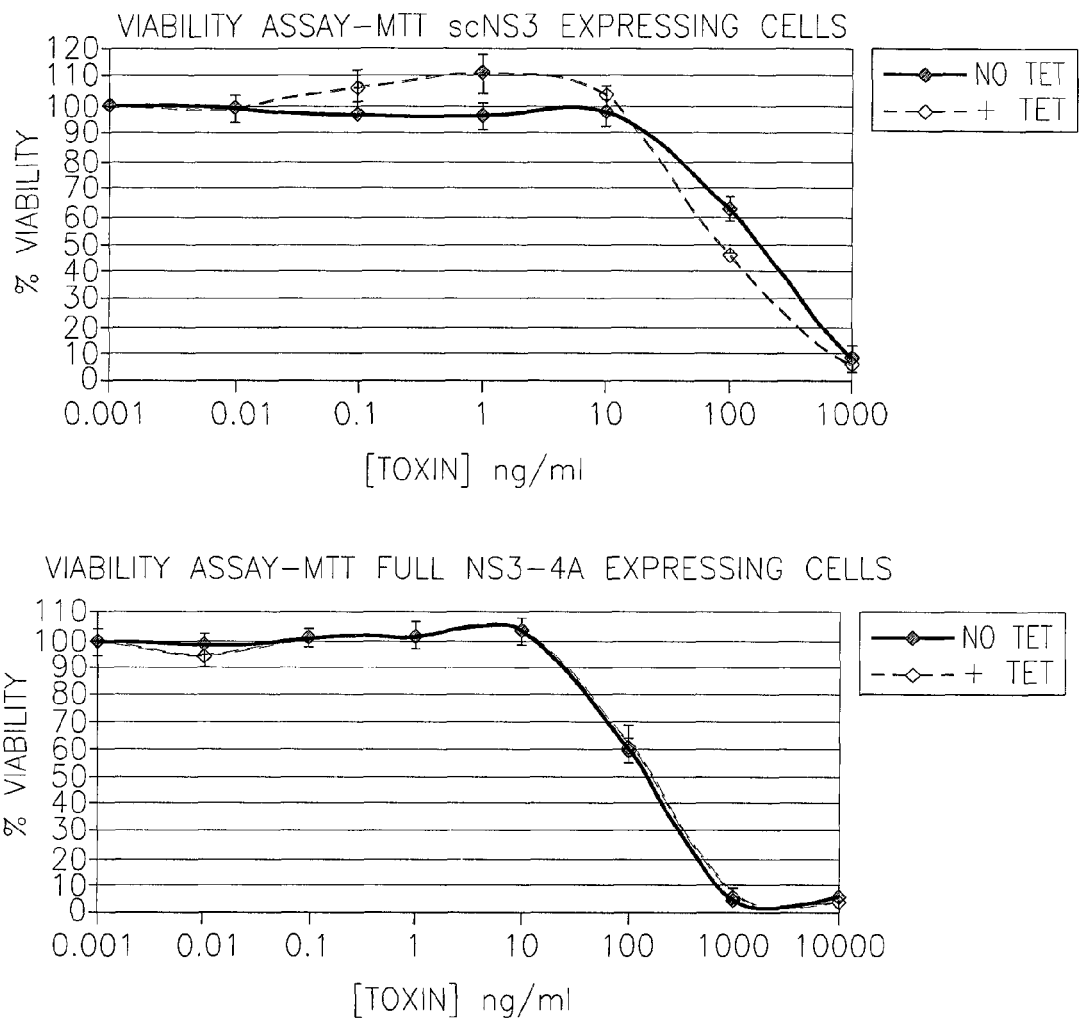
Figure 6A:
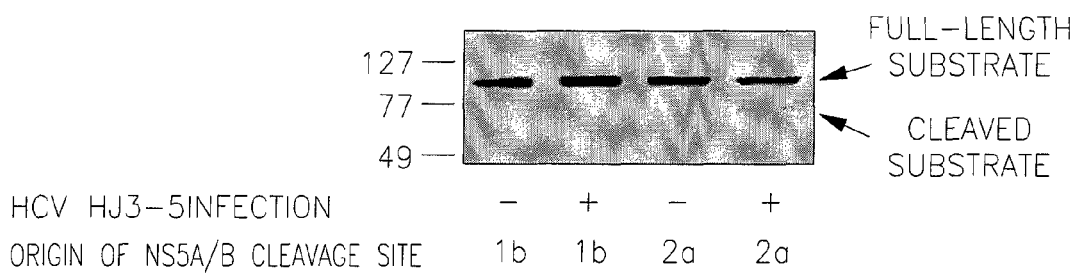
FIGS. 6B and 6C show the results of viability assays. HUH7.5 cells uninfected or infected with HJ3-5 chimeric virus were seeded (1×10⁴ cells per well) in 96 well plates. After 24 hours, cells were incubated for 96 hours with serial dilutions of the DTA based toxins "PE-DTA-cleavage site-defensin" and "PE-DTA-mutated cleavage site-defensin" (FIG. 6B), or the RTA based toxins "PE-RTA-cleavage site-stalk peptide" and "PE-RTA-mutated cleavage site-stalk peptide" (FIG. 6C) incorporating the P10-P10' NS3 cleavage sequence derived from 2a genotype NS5A/B junction. The relative fraction of viable cells was determined using an enzymatic MTT assay. A representative graph of three independent experiments is shown. Each point represents the mean±SD of a set of data determined in triplicate.
Figure 6B:
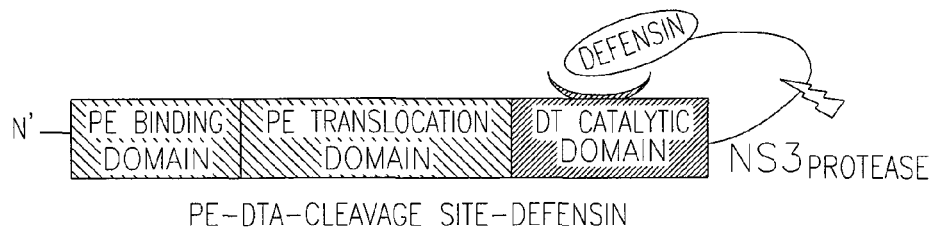
Figure 6B:
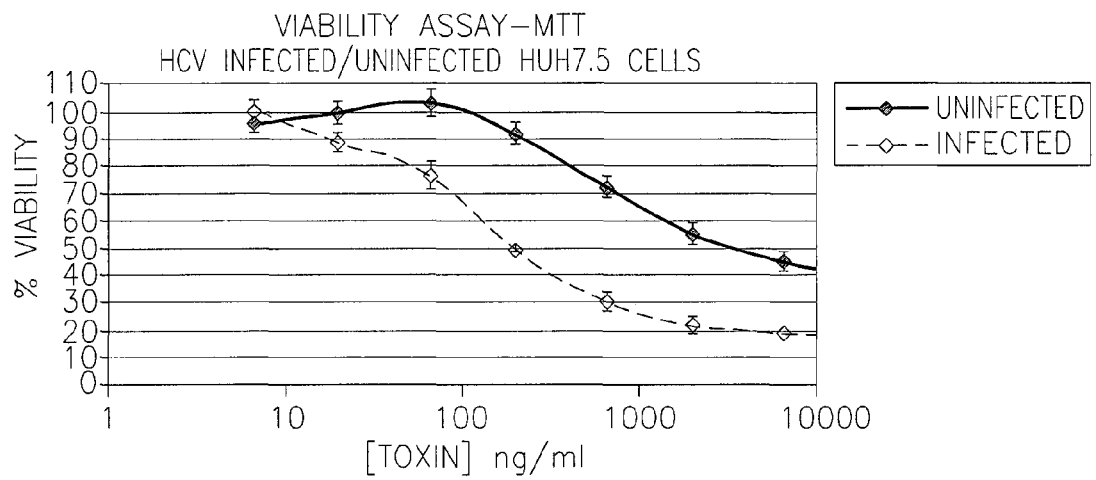
Figure 6B:
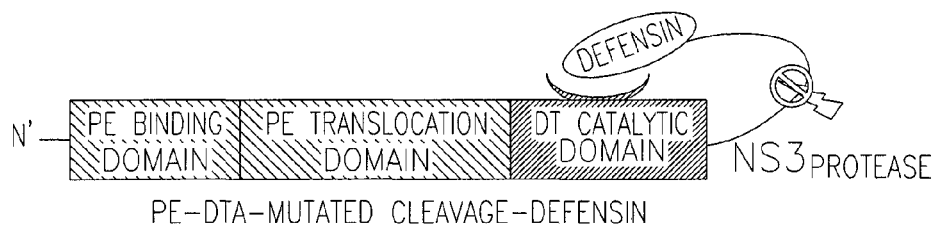
Figure 6B:
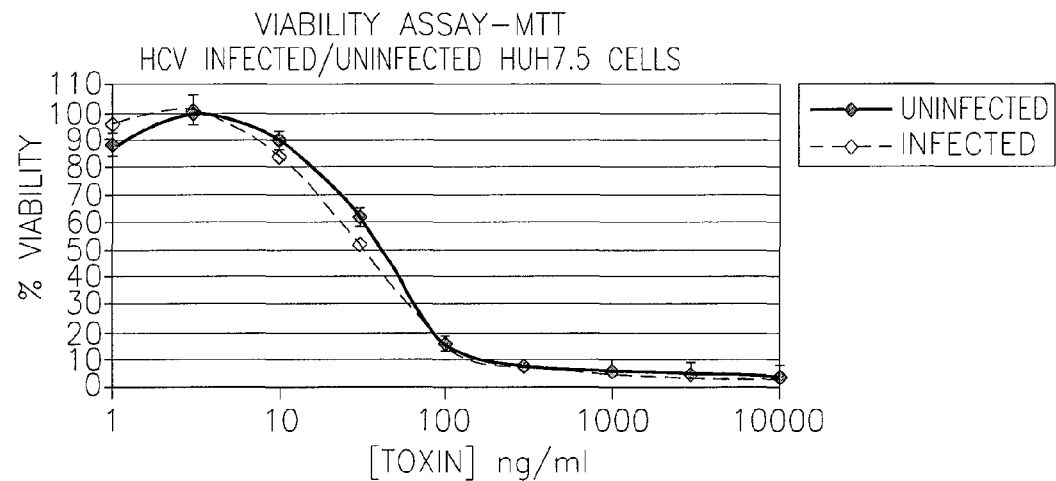
Figure 6C:
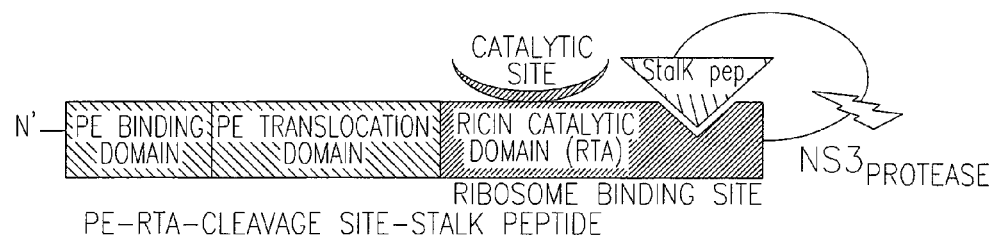
Figure 6C:
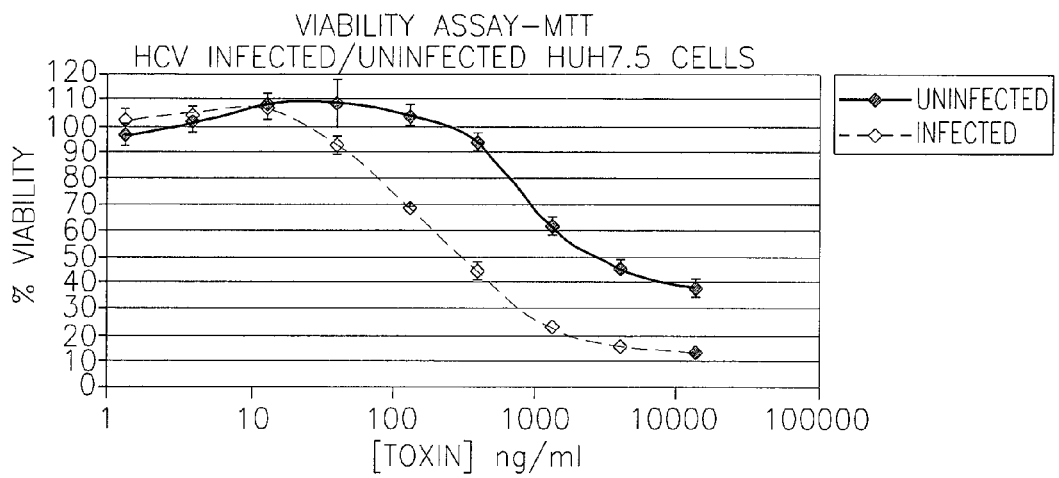
Figure 6C:
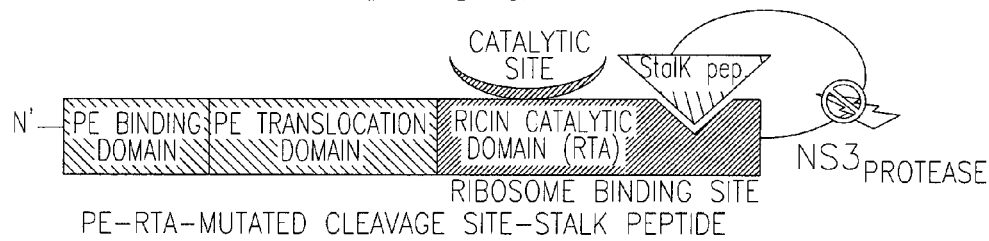
Figure 6C:
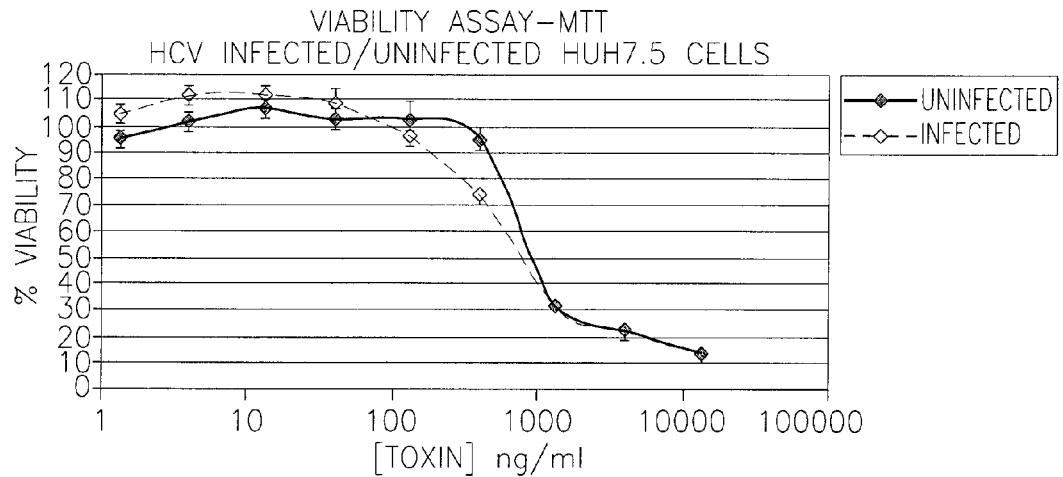

In order to verify toxin activation by HCV protease in vivo, our model cell lines, induced or uninduced for NS3 expression, were treated with the chimeric toxins "PE-RTA-cleavage site-stalk peptide" or "PE-RTA-mutated cleavage site-stalk peptide". As shown in FIG. 5, tetracycline induced expression of scNS3 and full NS3-4A led to considerable activation of the cleavable toxin, while no profound enhancement in cytotoxicity of control uncleavable toxin was observed. Another construct, in which only the 6×His-KDEL extension was fused to the C terminus of RTA, was also relatively inert to scNS3 protease expression exhibiting only minor enhancement in cytotoxicity toward Tet-induced scNS3 expressing cells (IC$_{50}$ values of 30 ng/ml vs. 20 ng/ml in uninduced and induced cells, respectively).

Example 8

Cytotoxicity of DTA- and RTA-Based Zymoxins is Elevated in HCV Infected Cells

Current models for study of hepatitis C virus enable production of recombinant infectious HCV particles (for example, genotype 2a strain JFH1 and other chimeric viruses generated in the JFH1 background) in Huh7 hepatoma-derived cell lines that are permissive for HCV replication, rendering all steps of the viral life cycle, including entry and release of viral particles, amenable to systematic analysis. (Lohmann et al., 1999; Blight et al., 2002; Lindenbach et al., 2005; Wakita et al., 2005; Zhong et al., 2005; Brass et al., 2006; Pietschmann et al., 2006; Rychlowska and Bienkowska-Szewczyk, 2007; Gottwein et al., 2009).

In order to evaluate the potential of the chimeric toxins disclosed herein to be cleaved and active in vivo, Huh7.5 cells uninfected or infected with the 1a/2a chimeric virus HJ3-5 (encoding the structural proteins of genotype 1a strain H77S within the background of JFH1; see (Yi et al., 2007; McGivern et al., 2009) were transfected with vectors encoding cleavage substrates. The vectors designated "pCMV/MBP-EGFP-full 1b NS5AB-CBD" and "pCMV/MBP-EGFP-full 2a NS5AB-CBD", encode the previously described NS3 cleavable substrate, modified in that the 10 amino acid minimal NS3 cleavage sequence from genotype 1b/1a NS5A/B junction was replaced by longer cleavage sequences of either 18 amino acids (P10-P8'), or 20 amino-acids (P10-P10'), from the 1b or 2a genotype NS5A/B junction sites, respectively.

Western blot analysis of lysate samples from uninfected and HJ3-5 infected cells indicated that the substrate incorporating the 2a NS5A/B site was cleaved in infected cells also expressing the NS3 protease (FIG. 6A). Accordingly, for subsequent experiments in HCV HJ3-5 infected cells, the 1b/1a genotype derived NS5A/B minimal cleavage site (P6-P4') was replaced by the longer 2a genotype NS5A/B junction sequence (P10-P10') in both DTA- and RTA-based cleavable zymoxins. As seen in FIGS. 6B and 6C, treatment of infected/uninfected Huh7.5 cells with both DTA- and RTA-based zymoxins resulted in enhanced cytotoxicity upon infected cells ($IC_{50}$ values of 3500 and 200 ng/ml for the cleavable DTA-based toxin in uninfected and infected cells, respectively; and 2500 and 300 ng/ml for the cleavable RTA based toxin in uninfected and infected cells, respectively). Treatment with the uncleavable controls resulted in a much less profound effect ($IC_{50}$ values of 40 and 30 ng/ml for the uncleavable DTA-based toxin in uninfected and infected cells, respectively, and 900 and 800 ng/ml for the uncleavable RTA-based toxin in uninfected and infected cells, respectively). No enhancement in cytotoxicity upon infected cells was observed following treatment with a different DTA-based uncleavable toxin, in which the whole NS3 cleavage site was deleted.

Based on the results disclosed herein, it is apparent that the chimeric toxins according to the invention may be used in the development of anti-viral agents for a large variety of disease causing viruses which encode a viral protease. Such viral targets include, but are not limited to flaviviruses such as hepatitis C virus (HCV), West Nile virus (WNV), dengue fever virus (DFV) and yellow fever virus (YFV); retroviruses such as HIV-1; picornaviruses such as coxsackievirus, poliovirus and hepatitis A virus, nidoviruses such as coronaviruses (CoV), including the severe acute respiratory syndrome (SARS) causative SARS-CoV; and herpesviruses such as varicella-zoster virus (VZV) and Epstein-Bar virus (EBV).

REFERENCES

1. Bartenschlager, R. (1999) The NS3/4A proteinase of the hepatitis C virus: unravelling structure and function of an unusual enzyme and a prime target for antiviral therapy. J Viral Hepat 6, 165-81.
2. Bass, H. W., Webster, C., G R, O. B., Roberts, J. K. and Boston, R. S. (1992) A maize ribosome-inactivating protein is controlled by the transcriptional activator Opaque-2. Plant Cell 4, 225-34.
3. Berdichevsky, Y., Zemel, R., Bachmatov, L., Abramovich, A., Koren, R., Sathiyamoorthy, P., Golan-Goldhirsh, A., Tur-Kaspa, R. and Benhar, I. (2003) A novel high throughput screening assay for HCV NS3 serine protease inhibitors. J Virol Methods 107, 245-55.
4. Blight, K. J., McKeating, J. A. and Rice, C. M. (2002) Highly permissive cell lines for subgenomic and genomic hepatitis C virus RNA replication. J Virol 76, 13001-14.
5. Brass, V., Moradpour, D. and Blum, H. E. (2006) Molecular virology of hepatitis C virus (HCV): 2006 update. Int J Med Sci 3, 29-34.
6. Chiou, J. C., Li, X. P., Remacha, M., Ballesta, J. P. and Turner, N. E. (2008) The ribosomal stalk is required for ribosome binding, depurination of the rRNA and cytotoxicity of ricin A chain in *Saccharomyces cerevisiae*. Mol Microbiol 70, 1441-52.
7. Collier, R. J. and Kandel, J. (1971) Structure and activity of diphtheria toxin. I. Thiol-dependent dissociation of a fraction of toxin into enzymically active and inactive fragments. J Biol Chem 246, 1496-503.
8. Debinski, W. and Pastan, I. (1994) An immunotoxin with increased activity and homogeneity produced by reducing the number of lysine residues in recombinant *Pseudomonas* exotoxin. Bioconjug Chem 5, 40-6.
9. Deng, Q. and Barbieri, J. T. (2008) Molecular mechanisms of the cytotoxicity of ADP-ribosylating toxins. Annu Rev Microbiol 62, 271-88.
10. Denkberg, G. and Reiter, Y. (2006) Recombinant antibodies with T-cell receptor-like specificity: novel tools to study MHC class I presentation. Autoimmun Rev 5, 252-7.
11. Dimasi, N., Pasquo, A., Martin, F., Di Marco, S., Steinkuhler, C., Cortese, R. and Sollazzo, M. (1998) Engineering, characterization and phage display of hepatitis C virus NS3 protease and NS4A cofactor peptide as a single-chain protein. Protein Eng 11, 1257-65.
12. Edwards, K., Johnstone, C. and Thompson, C. (1991) A simple and rapid method for the preparation of plant genomic DNA for PCR analysis. Nucleic Acids Res 19, 1349.
13. Falnes, P. O., Welker, R., Krausslich, H. G. and Olsnes, S. (1999) Toxins that are activated by HIV type-1 protease through removal of a signal for degradation by the N-end-rule pathway. Biochem J 343 Pt 1, 199-207.
14. FitzGerald, D. and Pastan, I. (1991) Redirecting *Pseudomonas* exotoxin. Semin Cell Biol 2, 31-7.
15. Frelin, L., Alheim, M., Chen, A., Soderholm, J., Rozell, B., Barnfield, C., Liljestrom, P. and Sallberg, M. (2003) Low dose and gene gun immunization with a hepatitis C virus nonstructural (NS) 3 DNA-based vaccine containing NS4A inhibit NS3/4A-expressing tumors in vivo. Gene Ther 10, 686-99.
16. Gal-Tanamy, M., Zemel, R., Berdichevsky, Y., Bachmatov, L., Tur-Kaspa, R. and Benhar, I. (2005) HCV NS3 serine protease-neutralizing single-chain antibodies isolated by a novel genetic screen. J Mol Biol 347, 991-1003.

17. Gottwein, J. M., Scheel, T. K., Jensen, T. B., Lademann, Prentoe, J. C., Knudsen, M. L., Hoegh, A. M. and Bukh, J. (2009) Development and characterization of hepatitis C virus genotype 1-7 cell culture systems: role of CD81 and scavenger receptor class B type I and effect of antiviral drugs. Hepatology 49, 364-77.

18. Gu, M., Gordon, V. M., Fitzgerald, D. J. and Leppla, S. H. (1996) Furin regulates both the activation of *Pseudomonas* exotoxin A and the Quantity of the toxin receptor expressed on target cells. Infect Immun 64, 524-7.

19. Gump, J. M. and Dowdy, S. F. (2007) TAT transduction: the molecular mechanism and therapeutic prospects. Trends in Molecular Medicine 13, 443-448.

20. Hwang, J., Fitzgerald, D. J., Adhya, S, and Pastan, I. (1987) Functional domains of *Pseudomonas* exotoxin identified by deletion analysis of the gene expressed in *E. coli*. Cell 48, 129-36.

21. Iglewski, B. H. and Kabat, D. (1975) NAD-dependent inhibition of protein synthesis by *Pseudomonas aeruginosa* toxin. Proc Natl Acad Sci USA 72, 2284-8.

22. Jackson, M. E., Simpson, J. C., Girod, A., Pepperkok, R., Roberts, L. M. and Lord, J. M. (1999) The KDEL retrieval system is exploited by *Pseudomonas* exotoxin A, but not by Shiga-like toxin-1, during retrograde transport from the Golgi complex to the endoplasmic reticulum. J Cell Sci 112 (Pt 4), 467-75.

23. Johnson, R. J., Lin, S. R. and Raines, R. T. (2006) A ribonuclease zymogen activated by the NS3 protease of the hepatitis C virus. Febs J 273, 5457-65.

24. Jorgensen, R., Merrill, A. R., Yates, S. P., Marquez, V. E., Schwan, A. L., Boesen, T. and Andersen, G. R. (2005) Exotoxin A-eEF2 complex structure indicates ADP ribosylation by ribosome mimicry. Nature 436, 979-84.

25. Jucovic, M., Walters, F. S., Warren, G. W., Palekar, N. V. and Chen, J. S. (2008) From enzyme to zymogen: engineering Vip2, an ADP-ribosyltransferase from *Bacillus cereus*, for conditional toxicity. Protein Eng Des Sel 21, 631-8.
26. Law, S. K., Wang, R. R., Mak, A. N., Wong, K. B., Zheng, Y. T. and Shaw, P. C. (2010) A switch-on mechanism to activate maize ribosome-inactivating protein for targeting HIV-infected cells. Nucleic Acids Res.
27. Lindenbach, B. D., Evans, M. J., Syder, A. J., Wolk, B., Tellinghuisen, T. L., Liu, C. C., Maruyama, T., Hynes, R. O., Burton, D. R., McKeating, J. A. and Rice, C. M. (2005) Complete replication of hepatitis C virus in cell culture. Science 309, 623-6.
28. Lohmann, V., Korner, F., Koch, J., Herian, U., Theilmann, L. and Bartenschlager, R. (1999) Replication of subgenomic hepatitis C virus RNAs in a hepatoma cell line. Science 285, 110-3.
29. Mansfield, E., Pastan, I. and FitzGerald, D. J. (1996) Characterization of RFB4-*Pseudomonas* exotoxin A immunotoxins targeted to CD22 on B-cell malignancies. Bioconjug Chem 7, 557-63.
30. May, M. J., Hartley, M. R., Roberts, L. M., Krieg, P. A., Osborn, R. W. and Lord, J. M. (1989) Ribosome inactivation by ricin A chain: a sensitive method to assess the activity of wild-type and mutant polypeptides. Embo J 8, 301-8.
31. McCluskey, A. J., Poon, G. M., Bolewska-Pedyczak, E., Srikumar, T., Jeram, S. M., Raught, B. and Gariepy, J. (2008) The catalytic subunit of shiga-like toxin 1 interacts with ribosomal stalk proteins and is inhibited by their conserved C-terminal domain. J Mol Biol 378, 375-86.
32. McGivern, D. R., Villanueva, R. A., Chinnaswamy, S., Kao, C. C. and Lemon, S. M. (2009) Impaired replication of hepatitis C virus containing mutations in a conserved NS5B retinoblastoma protein-binding motif. J Virol 83, 7422-33.
33. Moradpour, D., Gosert, R., Egger, D., Penin, F., Blum, H. E. and Bienz, K. (2003) Membrane association of hepatitis C virus nonstructural proteins and identification of the membrane alteration that harbors the viral replication complex. Antiviral Res 60, 103-9.
34. Moradpour, D., Penin, F. and Rice, C. M. (2007) Replication of hepatitis C virus. Nat Rev Microbiol 5, 453-63.
35. Munishkin, A. and Wool, I. G. (1995) Systematic deletion analysis of ricin A-chain function. Single amino acid deletions. J Biol Chem 270, 30581-7.
36. Olsnes, S. (2004) The history of ricin, abrin and related toxins. Toxicon 44, 361-70.
37. Pietschmann, T., Kaul, A., Koutsoudakis, G., Shavinskaya, A., Kallis, S., Steinmann, E., Abid, K., Negro, F., Dreux, M., Cosset, F. L. and Bartenschlager, R. (2006) Construction and characterization of infectious intragenotypic and intergenotypic hepatitis C virus chimeras. Proc Natl Acad Sci USA 103, 7408-13.
38. Plainkum, P., Fuchs, S. M., Wiyakrutta, S, and Raines, R. T. (2003) Creation of a zymogen. Nat Struct Biol 10, 115-9.
39. Ratts and Murphy. (2004) Diphtheria toxin, diphtheria-related fusion protein toxins, and the molecular mechanism of their action against eukaryotic cells. Topics in Current Genetics 11.
40. Rychlowska, M. and Bienkowska-Szewczyk, K. (2007) Hepatitis C—new developments in the studies of the viral life cycle. Acta Biochim Pol.
41. Shaki-Loewenstein, S., Zfania, R., Hyland, S., Wels, W. S, and Benhar, I. (2005) A universal strategy for stable intracellular antibodies. J Immunol Methods 303, 19-39.
42. Steinkuhler, C., Urbani, A., Tomei, L., Biasiol, G., Sardana, M., Bianchi, E., Pessi, A. and De Francesco, R. (1996) Activity of purified hepatitis C virus protease NS3 on peptide substrates. J Virol 70, 6694-700.
43. Stirpe, F. and Battelli, M. G. (2006) Ribosome-inactivating proteins: progress and problems. Cell Mol Life Sci 63, 1850-66.
44. Suzuki, T., Ishii, K., Aizaki, H. and Wakita, T. (2007) Hepatitis C viral life cycle. Adv Drug Deliv Rev.
45. Taremi, S. S., Beyer, B., Maher, M., Yao, N., Prosise, W., Weber, P. C. and Malcolm, B. A. (1998) Construction, expression, and characterization of a novel fully activated recombinant single-chain hepatitis C virus protease. Protein Sci 7, 2143-9.
46. Too, P. H., Ma, M. K., Mak, A. N., Wong, Y. T., Tung, C. K., Zhu, G., Au, S. W., Wong, K. B. and Shaw, P. C. (2009) The C-terminal fragment of the ribosomal P protein complexed to trichosanthin reveals the interaction between the ribosome-inactivating protein and the ribosome. Nucleic Acids Res 37, 602-10.
47. Turcotte, R. F. and Raines, R. T. (2008) Design and Characterization of an HIV-Specific Ribonuclease Zymogen. AIDS Res Hum Retroviruses.
48. Varshaysky, A. (1995) The N-end rule. Cold Spring Harb Symp Quant Biol 60, 461-78.
49. Vater, C. A., Bartle, L. M., Leszyk, J. D., Lambert, J. M. and Goldmacher, V. S. (1995) Ricin A chain can be chemically cross-linked to the mammalian ribosomal proteins L9 and L10e. J Biol Chem 270, 12933-40.
50. Wakita, T., Pietschmann, T., Kato, T., Date, T., Miyamoto, M., Zhao, Z., Murthy, K., Habermann, A., Krausslich, H. G., Mizokami, M., Bartenschlager, R. and Liang, T. J.

(2005) Production of infectious hepatitis C virus in tissue culture from a cloned viral genome. Nat Med 11, 791-6.
51. Walsh, T. A., Morgan, A. E. and Hey, T. D. (1991) Characterization and molecular cloning of a proenzyme form of a ribosome-inactivating protein from maize. Novel mechanism of proenzyme activation by proteolytic removal of a 2.8-kilodalton internal peptide segment. J Biol Chem 266, 23422-7.
52. Welsch, S., Muller, B. and Krausslich, H. G. (2007) More than one door—Budding of enveloped viruses through cellular membranes. FEBS Lett 581, 2089-97.
53. Wolk, B., Sansonno, D., Krausslich, H. G., Dammacco, F., Rice, C. M., Blum, H. E. and Moradpour, D. (2000) Subcellular localization, stability, and trans-cleavage competence of the hepatitis C virus NS3-NS4A complex expressed in tetracycline-regulated cell lines [In Process Citation]. J Virol 74, 2293-304.
54. Yi, M. and Lemon, S. M. (2004) Adaptive mutations producing efficient replication of genotype 1a hepatitis C virus RNA in normal Huh7 cells. J. Virol. 78, 7904-7915.
55. Yi, M., Ma, Y., Yates, J. and Lemon, S. M. (2007) Compensatory mutations in E1, p7, NS2, and NS3 enhance yields of cell culture-infectious intergenotypic chimeric hepatitis C virus. J Virol 81, 629-38.
56. Yi, M., Villanueva, R. A., Thomas, D. L., Wakita, T. and Lemon, S. M. (2006) Production of infectious genotype 1a hepatitis C virus (Hutchinson strain) in cultured human hepatoma cells. Proc. Natl. Acad. Sci. U.S.A 103, 2310-2315.
57. Zemel, R., Berdichevsky, Y., Bachmatov, L., Benhar, I. and Tur-Kaspa, R. (2004) Inhibition of Hepatitis C Virus NS3-mediated cell transformation by recombinant intracellular antibodies. J Hepatol 40, 1000-1007.
58. Zhong, J., Gastaminza, P., Cheng, G., Kapadia, S., Kato, T., Burton, D. R., Wieland, S. F., Uprichard, S. L., Wakita, T. and Chisari, F. V. (2005) Robust hepatitis C virus infection in vitro. Proc Natl Acad Sci USA 102, 9294-9.

The invention claimed is:

1. A multi-domain toxin protein conjugate comprising an amino acid sequence selected from the group consisting of SEQ ID NOs: 64-68.

2. A polynucleotide encoding the protein conjugate according to claim 1, comprising a nucleic acid sequence selected from the group consisting of SEQ ID NOs: 69-73.

3. A pharmaceutical composition comprising the protein conjugate of claim 1 and a pharmaceutically acceptable carrier.

4. A method of inducing killing of HCV infected cells, comprising administering to a subject in need thereof an effective amount of the pharmaceutical composition according to claim 3, thereby inducing killing of HCV infected cells.

5. The method according to claim 4, wherein the administering comprises a delivery route selected from the group consisting of infusion, bolus injection, direct injection to an organ or infection site, and oral.

* * * * *